(12) United States Patent
Brines et al.

(10) Patent No.: US 7,718,363 B2
(45) Date of Patent: May 18, 2010

(54) TISSUE PROTECTIVE CYTOKINE RECEPTOR COMPLEX AND ASSAYS FOR IDENTIFYING TISSUE PROTECTIVE COMPOUNDS

(75) Inventors: Michael Brines, Woodbridge, CT (US); Anthony Cerami, Somers, NY (US); Thomas Coleman, Mt. Kisco, NY (US)

(73) Assignee: The Kenneth S. Warren Institute, Inc., Ossining, NY (US)

( * ) Notice: Subject to any disclaimer, the term of this patent is extended or adjusted under 35 U.S.C. 154(b) by 1005 days.

(21) Appl. No.: 10/676,694

(22) Filed: Sep. 30, 2003

(65) Prior Publication Data

US 2004/0214236 A1 Oct. 28, 2004

Related U.S. Application Data

(60) Provisional application No. 60/465,891, filed on Apr. 25, 2003.

(51) Int. Cl.
C12Q 1/68 (2006.01)
C12Q 1/00 (2006.01)
G01N 33/53 (2006.01)

(52) U.S. Cl. .................. 435/6; 435/4; 435/7.2
(58) Field of Classification Search .......... None
See application file for complete search history.

(56) References Cited

U.S. PATENT DOCUMENTS

| | | | |
|---|---|---|---|
| 5,278,065 A | 1/1994 | D'Andrea et al. | |
| 5,292,654 A | 3/1994 | Yoshimura et al. | |
| 5,763,198 A | 6/1998 | Hirth et al. | |
| 5,997,865 A | 12/1999 | Bennett et al. | |
| 6,159,705 A * | 12/2000 | Trueheart et al. | 435/29 |
| 6,200,567 B1 | 3/2001 | Lopez et al. | |
| 6,475,717 B1 | 11/2002 | Enssle et al. | |
| 6,531,121 B2 | 3/2003 | Brines et al. | |
| 7,309,687 B1 | 12/2007 | Brines et al. | |
| 7,345,019 B1 | 3/2008 | Brines et al. | |
| 7,410,941 B1 | 8/2008 | Brines et al. | |
| 2002/0031806 A1 | 3/2002 | Lee | |
| 2002/0086816 A1 | 7/2002 | Brines et al. | |
| 2003/0072737 A1 | 4/2003 | Brines et al. | |
| 2003/0104988 A1 | 6/2003 | Brines et al. | |
| 2003/0134798 A1 | 7/2003 | Brines et al. | |
| 2004/0122216 A1 | 6/2004 | Nielsen et al. | |
| 2004/0214236 A1 | 10/2004 | Brines et al. | |
| 2005/0176627 A1 | 8/2005 | Cerami et al. | |
| 2006/0034799 A1 | 2/2006 | Brines et al. | |
| 2006/0216757 A1 | 9/2006 | Brines et al. | |
| 2007/0129293 A1 | 6/2007 | Coleman et al. | |
| 2007/0298031 A1 | 12/2007 | Brines et al. | |
| 2008/0014193 A1 | 1/2008 | Brines et al. | |
| 2008/0045412 A1 | 2/2008 | Buarque de Macedo | |
| 2008/0305990 A1 | 12/2008 | Brines et al. | |
| 2009/0004202 A1 | 1/2009 | Brines et al. | |
| 2009/0136519 A1 | 5/2009 | Brines et al. | |

FOREIGN PATENT DOCUMENTS

| | | |
|---|---|---|
| EP | 1622570 | 2/2006 |
| WO | WO 00/35475 | 6/2000 |
| WO | WO 00/61164 | 10/2000 |
| WO | WO 02/053580 | 7/2002 |
| WO | WO 2004/003176 | 1/2004 |
| WO | WO 2004/004656 | 1/2004 |
| WO | WO 2004/022577 | 3/2004 |
| WO | WO 2004/096148 | 11/2004 |
| WO | WO 2004/112693 | 12/2004 |
| WO | WO 2005/025606 | 3/2005 |
| WO | WO 2005/032467 | 4/2005 |
| WO | WO 2005/084364 | 9/2005 |
| WO | WO 2005/117927 | 12/2005 |
| WO | WO 2006/002646 | 1/2006 |
| WO | WO 2002/000721 | 2/2006 |
| WO | WO 2006/014349 | 2/2006 |
| WO | WO 2006/014466 | 2/2006 |

OTHER PUBLICATIONS

MercuryTM Pathway Profiling System User Manual, Clontech, Mar. 2, 2001.*
Barber et al.,1994, "Erythropoietin and interleukin-2 activate distinct JAK kinase family members," Mol. Cell. Biol. 14(10):6506-6514.
Barbone et al., 1997, "Mutagenesis studies of the human erythropoietin receptor. Establishment of structure-function relationships," J. Biol. Chem. 272(8):4985-4992.
Bazan, 1989, "A novel family of growth factor receptors: a common binding domain in the growth hormone, prolactin, erythropoietin and IL-6 receptors, and the p75 IL-2 receptor beta-chain," Biochem. Biophys. Res. Commun. 164(2):788-795.
Benit et al., 1993, "The 'WS motif' common to v-mpl and members of the cytokine receptor superfamily is dispensable for myeloproliferative leukemia virus pathogenicity," Oncogene 8(3):787-790.
Bonsi et al., 1997, "An erythroid and megakaryocytic common precursor cell line (B1647) expressing both c-mpl and erythropoietin receptor (Epo-R) proliferates and modifies globin chain synthesis in response to megakaryocyte growth and development factor (MGDF) but not to erythropoietin (Epo)," Br. J. Haematol. 98(3):549-559.

(Continued)

*Primary Examiner*—Ruixiang Li
(74) *Attorney, Agent, or Firm*—Jones Day

(57) ABSTRACT

The present invention is directed methods for identifying compounds that have a tissue protective activity using a heteromultimer receptor complex that mediates the tissue protective activities. The complex consists of at least one EPO-R in complex with at least one $\beta_c$ Receptor. These compounds used in the assays to identify tissue protective compounds include, but are not limited to, small molecules and biologics. The compounds identified using these assays can be used to treat various conditions of the central and peripheral nervous systems as well as those of other erythropoietin-responsive or excitable cells, tissues, and organs.

25 Claims, 12 Drawing Sheets

OTHER PUBLICATIONS

Boudot et al., 1999, "Erythropoietin induces glycosylphosphatidylinositol hydrolysis. Possible involvement of phospholipase c-gamma(2)," J. Biol. Chem. 274(48):33966-33972.

Brizzi et al., 1991, "Hematopoietic growth factor receptors," Int. J. Cell. Cloning 9(4):274-300.

Caravella et al., 1996, "A partial model of the erythropoietin receptor complex," Proteins 24(3):394-401.

D'Andrea et al., 2000, "A model for assembly and activation of the GM-CSF, IL-3 and IL-5 receptors: insights from activated mutants of the common beta subunit," Exp. Hematol. 28(3):231-243.

D'Andrea et al., 1998, "Dysregulated hematopoiesis and a progressive neurological disorder induced by expression of an activated form of the human common beta chain in transgenic mice," J. Clin. Invest. 102(11):1951-1960.

D'Andrea and Zon, 1990, "Erythropoietin receptor. Subunit structure and activation," J. Clin. Invest. 86(3):681-687.

Frank, 2002, "Receptor dimerization in GH and erythropoietin action—it takes two to tango, but how?" Endocrinology 143(1):2-10.

Fung et al., 1990, "The human interleukin-2 receptor: insights into subunit structure and growth signal transduction," Semin. Immunol. 2(2):119-128.

Grotzinger, 2002, "Molecular mechanisms of cytokine receptor activation," Biochim. Biophys. Acta. 1592(3):215-223.

Hanazono et al., 1995, "Erythropoietin induces tyrosine phosphorylation of the b chain of the GM-CSF receptor," Biochem. Biophys. Res. Comm. 208(3):1060-1066.

Harris et al. 1992, "Ligand binding properties of the human erythropoietin receptor extracellular domain expressed in *Escherichia coli*," J. Biol. Chem. 267(21):15205-15209.

Hassan et al., 1995, "Characteristic biological features of human megakaryoblastic leukaemia cell lines," Leuk. Res. 19(9):589-594.

Imada et al., 1992, "Interleukin-2 (IL-2) induces erythroid differentiation and tyrosine phosphorylation in ELM-I-I cells transfected with a human IL-2 receptor beta chain cDNA," Biochem. Biophys. Res. Commun. 188(1):352-357.

Itoh et al., 1990, "Cloning of an interleukin-3 receptor gene: a member of a distinct receptor gene family," Science 247(4940):324-327.

Jenkins et al., 1999, "A cell type-specific constitutive point mutant of the common beta-subunit of the human granulocyte-macrophage colony-stimulating factor (GM-CSF), interleukin (IL)-3, and IL-5 receptors requires the GM-CSF receptor alpha-subunit for activation," J. Biol. Chem. 274(13):8669-8677.

Jones et al., 1990, "Human erythropoietin receptor: cloning, expression, and biologic characterization," Blood 76(1):31-35.

Jubinsky et al., 1997, "The beta chain of the interleukin-3 receptor functionally associates with the erythropoietin receptor," Blood 90(5):1867-1873.

Jubinsky et al., 1996, "The beta c component of the granulocyte-macrophage colony-stimulating factor (GM-CSF)/interleukin 3 (IL-3)/IL-5 receptor interacts with a hybrid GM-CSF/erythropoietin receptor to influence proliferation and beta-globin mRNA expression," Mol. Med. 2(6):766-773.

Kirito et al., 2002, "Identification of the human erythropoietin receptor region required for Stat1 and Stat3 activation," Blood 99(1):102-110.

Lai et al., 1996, "The molecular role of the common gamma c subunit in signal transduction reveals functional asymmetry within multimeric cytokine receptor complexes." Proc. Natl. Acad. Sci. USA 93(1):231-235.

Lewis et al., 2004, "Opposing effects of PI3 kinase pathway activation on human myeloid and erythroid progenitor cell proliferation and differentiation in vitro," Exp. Hematol. 32(1):36-44.

Lewis et al., 1996, "Molecular characterization of the 7q deletion in myeloid disorders," Br. J. Haematol. 93(1):75-80.

Liu et al., 1994, "Multiple cytokines stimulate the binding of a common 145-kilodalton protein to Shc at the Grb2 recognition site of Shc," Mol. Cell. Biol. 14(10):6926-6935.

Livnah et al., 1999, "Crystallographic evidence for preformed dimers of erythropoietin receptor before ligand activation," Science 283(5404):987-990.

McClure et al., 2001, "GM-CSF binding to its receptor induces oligomerisation of the common beta-subunit," Cytokine 13(4):240-243.

Means et al., 1996, "Inhibition of human erythroid colony-forming units by interferons alpha and beta: differing mechanisms despite shared receptor," Exp. Hematol. 24(2):204-208.

Murakami et al., 1991, "Critical cytoplasmic region of the interleukin 6 signal transducer gp130 is conserved in the cytokine receptor family," Proc. Natl. Acad. Sci. USA 88(24):11349-11353.

Murray, 1996, Harpers Biochemistry 24th ed. pp. 524-526, Appilion & Lange, Ltd.

Naranda et al., 2002, "Activation of erythropoietin receptor through a novel extracellular binding site," Endocrinology 143(6):2293-2302.

Nathan, 1994, "Studies of hybrid hematopoietic growth factor receptors," Stem Cells 12 Suppl 1:27-33.

Noguchi et al., 1991, "Cloning of the human erythropoietin receptor gene," Blood 78(10):2548-2556.

Penny and Forget, 1991, "Genomic organization of the human erythropoietin receptor gene," Genomics 11(4):974-980.

Remy et al., 1999, "Erythropoietin receptor activation by a ligand-induced conformation change," Science 283(5404):990-993.

Scott et al., 2000, "Reassessment of interactions between hematopoietic receptors using common beta-chain and interleukin-3-specific receptor beta-chain-null cells: no evidence of functional interactions with receptors for erythropoietin, granulocyte colony-stimulating factor, or stem cell factor," Blood 96(4):1588-1590.

Shikama et al., 1996, "A constitutively activated chimeric cytokine receptor confers factor-independent growth in hematopoietic cell lines," Blood 88(2):455-464.

Tojo et al., 1987, "Identification of erythropoietin receptors on fetal liver erythroid cells," Biochem. Biophys. Res. Commun. 148(1):443-448.

Williamson et al., 1993, "Protein and lipid kinase activation cascades in interleukin-2 receptor signalling," Semin. Immunol. 5(5):337-344.

Winkelmann et al., 1990, "The gene for the human erythropoietin receptor: analysis of the coding sequence and assignment to chromosome 19p," Blood 76(1):24-30.

Yamamura et al., 1992, "Distinct downstream signaling mechanism between erythropoietin receptor and interleukin-2 receptor," EMBO J. 11(13):4909-4915.

Yet et al, 1993, "The extracytoplasmic domain of the erythropoietin receptor forms a monomeric complex with erythropoietin," Blood 82(6):1713-1719.

Yoshimura et al., 1996, "Mouse oncostatin M: an immediate early gene induced by multiple cytokines through the JAK-STAT5 pathway," EMBO J. 15(5):1055-1063.

Yoshimura et al., 1996, "Physician Education: The Erythropoietin Receptor and Signal Transduction," Oncologist 1(5):337-339.

Yoshimura et al., 1995, "A novel cytokine-inducible gene CIS encodes an SH2-containing protein that binds to tyrosine-phosphorylated interleukin 3 and erythropoietin receptors," EMBO J. 14(12):2816-2826.

Zhu et al., 2002, "Detecting and responding to hypoxia," Nephrol. Dial. Transplant. 17 Suppl 1:3-7.

Gorio et al., 2002, "Recombinant human erythropoietin counteracts secondary injury and markedly enhances neurological recovery from experimental spinal cord trauma, " Proc. Nat. Acad. Sci. USA 99:9450-5.

Calvillo et al., 2003, "Recombinant human erythropoietin protects the myocardium from ischemia-reperfusion injury and promotes beneficial remodeling," Proc. Nat. Acad. Sci. USA 100:4802-6.

U.S. Appl. No. 09/290,938, filed Apr. 13, 1999, Brines et al.

U.S. Appl. No. 09/547,220, filed Apr. 11, 2000, Brines et al.

U.S. Appl. No. 09/716,963, filed Nov. 21, 2000, Brines et al.

U.S. Appl. No. 09/718,829, filed Nov. 21, 2000, Brines et al.

U.S. Appl. No. 11/283,024, filed Nov. 18, 2005, Cerami et al.

U.S. Appl. No. 11/880,275, filed Jul. 19, 2007, Brines et al.

Patent Interference No. 105,500 *Ehrenreich* v. *Brines*: Judgment Paper 1, Declaration, Brines clean copy of claims, and Ehrenreich clean copy of claims (Oct. 2, 2006).

Office Action, U.S. Appl. No. 11/259,326, date mailed: Aug. 7, 2008.

Office Action, U.S. Appl. No. 11/259,326, date mailed: May 13, 2009.

Supplementary European Search Report, Application No. 04760431.9, date mailed: Jun. 8, 2009.

International Search Report, PCT/US04/13099; mailed Jan. 11, 2006.

International Preliminary Report of Patentability, PCT/US04/13099; mailed Jun. 12, 2006.

Written Opinion, PCT/US04/13099; mailed Jan. 11, 2006.

* cited by examiner

TISSUE PROTECTIVE CYTOKINE RECEPTOR COMPLEX AND ASSAYS FOR IDENTIFYING TISSUE PROTECTIVE COMPOUNDS

This application claims benefit of priority under 35 U.S.C. § 119(e) to U.S. provisional patent Application No. 60/465,891, filed Apr. 25, 2003, the entire contents of which is incorporated herein by reference in its entirety.

1. INTRODUCTION

The present invention is directed to methods for use of tissue protective cytokine receptor complexes having at least one beta common ($\beta_c$) receptor and at least one erythropoietin (EPO) receptor. In particular, the present invention is drawn to methods for identifying and screening for compounds that modulate the interaction of a tissue protective cytokine receptor complex and a tissue protective cytokine receptor complex ligand. The methods of the invention also encompass methods for detecting compounds with tissue protective activity.

2. BACKGROUND OF THE INVENTION

Several lines of evidence suggest that erythropoietin, as a member of the cytokine superfamily, performs important physiologic functions which are mediated through interaction with the erythropoietin receptor (EPO-R). These actions include production of red blood cells, mitogenesis, modulation of calcium influx into smooth muscles and neural cells, and effects on intermediary metabolism.

EPO-R is a 66 kDa protein, and is part of the Type-1 cytokine receptor family. This family includes receptors for interleukin (IL)-IL2, IL3, IL4, IL5, IL6, IL7, IL9, IL11, granulocyte macrophage—colony stimulating factor (GM-CSF), granulocyte colony stimulating factor (G-CSF), Leukaemia Inhibiting Factor (LIF), Ciliary Neurotrophic Factor (CNTF), Thrombopoietin, Growth Hormone and Prolactin. These receptors are grouped together because of the homology of their extracellular domains. The conserved extracellular domain of these receptors has a length of approximately 200 amino acids, which contains four positionally conserved cysteine residues in the amino-terminal region (Cys 294, Cys 283, Cys 248, Cys 238) and a Trp-Ser-X-Trp-Ser motif located proximal to the transmembrane domain. The four cysteines appear to be critical to the maintenance and the structural integrity of the receptors (Murray, 1996, Harpers Biochemistry $24^{th}$ ed. pp. 524-526, Appilion & Lange, Ltd.; Caravella et al., 1996, Protein: Struct. Funct. Gen. 24:394-401;).

Like many of the receptors within the Type-1 cytokine receptor family, the EPO-R appears to be activated when it is activated by its interaction with EPO. The first EPO-R in the dimer binds to EPO with a high affinity and the second EPO-R then binds to the complex with a low affinity. This dimerization of the EPO-R puts the Jak2 tyrosine kinases associated with EPO-R in close association, inducing their transphosphorylation. This activation leads to the tyrosine phosphorylation of several proteins that subsequently activate several different pathways, such as phosphatidylinositol (PI) 3-kinase pathway, the Ras/MAP kinase pathway, and the STAT pathway. These pathways trigger the physiological functions mediated by erythropoietin (Kirito et al., 2002, Blood 99:102-110; Livnah et al., 1999, Science 283:987-990; Naranda et al., 2002, Endocrinology 143:2293-2302; Remy et al., 1999, Science 283:990-993; and Yoshimura et al., 1996, The Oncol. 1:337-339).

In addition to forming multimers, many of the members of the type-1 family incorporate one of three different signal transducing receptor components—gp130, beta common ($\beta_c$ receptor), or the gamma subunit of the IL2 receptor ($\gamma_c$ receptor)—in to their receptor complexes. For example, the receptor complex for GM-CSF consists of GM-CSF receptor, two $\beta_c$ receptors, and the GM-CSF ligand. The EPO-R has been known to form a complex with the $\beta_c$ receptor (See Yutaka et al., 1995, Bioch. Biophys. Res. Com. 208:1060-1066; Jubinsky et al., 1997, Blood 90:1867-1873; D'Andrea et al., 1998, J. Clin, Invest. 102:1951-1960). However, it has been reported that these complexes failed to result in any physiologically relevant effect (Scott et al., 2000, Blood, 96:1588-1590).

Recently a class of tissue protective cytokines, chemical or genetically modified erythropoietin molecules that demonstrate an enhanced tissue protective activity without any therapeutic erythropoietic effect have been disclosed. (See PCT Application No. PCT/US01/49479, U.S. patent application Ser. Nos. 10/188,905, 10/185,841, and 10/612,665, which are incorporated herein by reference herein in their entirety). These tissue protective cytokines protect, maintain, enhance and/or restore the function and/or viability of erythropoietin-responsive mammalian cells, tissues and organs, which include, but are not limited to, neuronal, retinal, muscle, heart, kidney cells or tissues. For example, these tissue protective cytokines have proven to be particularly effective in protecting against injury resulting from trauma and resulting inflammation to the brain (ischemic stroke, blunt trauma, subarrachnoid hemorrhage), spinal cord (ischemia, blunt force trauma), peripheral nerves (sciatic nerve injury, diabetic neuropathy, carpal tunnel syndrome), retinal (macular edema), and heart (myocardial infarct, chronic heart failure).

Unlike EPO, which binds the classical EPO-R dimer and provides a protective effect, it appears some modified EPO may not modulate the tissue protective activity by the same pathway since some of these tissue protective cytokines do not bind to the EPO-R homodimer. For example, a tissue protective cytokine generated by carbamylating erythropoietin in accordance with the procedure outlined in Example 2(B) of U.S. patent application Ser. No. 10/188,905 does not bind to the dimer EPO-R. (FIG. 1). The failure of the carbamylated tissue protective cytokine to bind to the EPO-R homodimer suggests that an alternative receptor or receptor complex mediates the tissue protective activity of these molecules.

It is towards this alternative receptor or receptor complex and the use of such alternative receptor or receptor complex as a means of screening potential compounds for tissue protective activities, that the present invention is directed.

3. SUMMARY

In one aspect, the present invention is directed to the use of tissue protective cytokine receptor complexes, comprising an EPO receptor and a $\beta_c$, in screening assays to identify compounds that exhibit a tissue protective activity. In one particular aspect, the compounds identified by the screening methods of the invention increase the activity of the tissue protective cytokine receptor complex and exhibit a tissue protective activity. In another particular aspect, the compounds identified by the screening methods of the invention increase modulate the interaction of a tissue protective cytokine receptor complex and a ligand thereof and exhibit a tissue protective activity.

In one embodiment, the invention provides for a method for identifying a compound that modulates a tissue protective activity comprising contacting a test compound with a tissue protective cytokine receptor complex, measuring the level of tissue protective cytokine receptor complex activity, identifying a test compound which increases or decreases the level of tissue protective cytokine receptor complex activity as compared to the level of tissue protective cytokine receptor complex activity measured in the absence of the test compound, and assaying the identified test compound for tissue protective activity wherein the tissue protective cytokine receptor complex activity is measured by measuring the binding of the test compound to the tissue protective cytokine receptor complex. In certain embodiments, the test compound is labeled and binding of the labeled test compound to the tissue protective cytokine receptor complex is measured by detecting the label attached to the test compound. In certain embodiments, the tissue protective cytokine receptor complex activity is measured by measuring the binding of the test compound to the tissue protective cytokine receptor complex.

In another embodiment, the invention provides for a method for identifying a compound that modulates a tissue protective activity comprising contacting a test compound with a tissue protective cytokine receptor complex-expressing cell and measuring the level of tissue protective cytokine receptor complex activity in the cell, identifying a test compound which increases or decreases the tissue protective cytokine receptor complex activity as compared to the level of tissue protective cytokine receptor complex activity measured in the absence of the test compound, and assaying for the identified test compound for a tissue protective activity. In a related embodiment, the tissue protective cytokine receptor complex activity is measured by a cell proliferation assay. In one embodiment, the cell is recombinantly engineered to express at least one EPO or β common receptors. In certain embodiments, the tissue protective cytokine receptor complex activity is measured by a cell proliferation assay. In certain embodiments, the cell is recombinantly engineered to express at least one EPO or β common receptors. In certain embodiments, the cell endogenously expresses an EPO receptor and is transformed with a nucleic acid comprising a nucleotide sequence that (i) is operably linked to a promoter, and (ii) encodes a β common receptor polypeptide. In certain embodiments, the cell endogenously expresses a β common receptor and is transformed with a nucleic acid comprising a nucleotide sequence that (i) is operably linked to a promoter, and (ii) encodes an EPO receptor polypeptide. In certain embodiments, the nucleotide sequence is derived from the same species as the cell.

In certain embodiments of the screening methods of the invention described herein above, the cell endogenously expresses an EPO receptor and is transformed with a nucleic acid comprising a nucleotide sequence that (i) is operably linked to a promoter, and (ii) encodes a β common receptor polypeptide.

In certain other embodiments of the screening methods of the invention described herein above, the cell endogenously expresses a β common receptor and is transformed with a nucleic acid comprising a nucleotide sequence that (i) is operably linked to a promoter, and (ii) encodes an EPO receptor polypeptide.

In certain embodiments of the screening methods of the invention described herein above, wherein the cell is transformed with a nucleic acid, the nucleotide sequence is derived from the same species as the cell.

The invention also provides for a method for identifying a compound that modulates a tissue protective activity, comprising contacting a test compound with a cell which is recombinantly engineered to express an EPO receptor, wherein said cell is transformed with a nucleic acid comprising a nucleotide sequence that (i) is operably linked to a promoter, and (ii) encodes a β common receptor polypeptide, measuring the level of tissue protective cytokine receptor complex activity in the cell, identifying a test compound that increases or decreases the level of tissue protective cytokine receptor complex activity in the cell relative to the level of tissue protective cytokine receptor complex activity measured in a control cell, wherein the control cell is of the same cell type as the cell contacted with the test compound and is not transformed with a nucleic acid comprising a nucleotide sequence that (i) is operably linked to a promoter, and (ii) encodes a β common receptor polypeptide, and assaying the identified test compound for a tissue protective activity.

The invention further provides for a method for identifying a compound that modulates a tissue protective activity, comprising contacting a test compound with a recombinant cell that expresses a β common receptor, wherein said cell is transformed with a nucleic acid comprising a nucleotide sequence that (i) is operably linked to a promoter, and (ii) encodes a EPO receptor polypeptide measuring the level of tissue protective cytokine receptor complex activity in the cell, identifying a test compound that increases or decreases the level of tissue protective cytokine receptor complex activity in the cell relative to the level of tissue protective cytokine receptor complex activity measured in a control cell, wherein the control cell is of the same cell type as the cell contacted with the test compound and is not transformed with a nucleic acid comprising a nucleotide sequence that (i) is operably linked to a promoter, and (ii) encodes a β common receptor polypeptide, and assaying the identified test compound for a tissue protective activity.

The invention yet further provides for a method for identifying a compound that modulates a tissue protective activity, comprising contacting a test compound with a tissue protective cytokine receptor complex-expressing cell, wherein said cell is transformed with a nucleic acid comprising a nucleotide sequence that encodes a reporter gene operably linked to a regulatory element associated with a tissue protective cytokine receptor complex activity, identifying a test compound that increases or decreases the level of reporter gene expression relative to the level of reporter gene expression measured in the absence of the test compound, and assaying the identified test compound for a tissue protective activity. In certain embodiments of the methods of the invention, the regulatory element is a serum response element.

The invention still further provides for a method of identifying a compound that modulates a tissue protective activity, comprising contacting a test compound with a cell comprising, (i) a nucleic acid sequence comprising a reporter gene operably liked to a binding site specific for a DNA binding domain of a transcriptional activator, (ii) a first fusion protein comprising (A) the DNA binding domain of the transactiptional activator, and (B) a first tissue protective cytokine receptor polypeptide or a fragment thereof, and (iii) a second fusion protein comprising (A) an activation domain of the transactiptional activator and (B) a second tissue protective cytokine receptor, detecting reporter gene expression, such that if the reporter gene expression detected in the presence of the test compound differs relative to the reporter gene expression detected in the absence of the test compound, a compound that modulates a tissue protective activity is identified.

In certain embodiments of the methods of the invention described herein above where a cell is contacted with a test compound, the cell is a eukaryotic cell. In certain embodiments of the methods of the invention described herein above, the eukaryotic cell is a human cell. In one embodiment, the cell is a prokaryotic cell. In certain embodiments of the invention described herein above where a cell is contacted with a test compound, the cell endogenously expresses at least one receptor of the tissue protective cytokine receptor complex. In certain embodiments of the invention described herein above where a cell is contacted with a test compound, the cell is a BaF3 cell.

In one embodiment, the invention provides for a method of identifying a compound that modulates the activity of a tissue protective cytokine receptor complex, said method comprising contacting a test compound with a cell of a modified yeast strain containing (i) a nucleotide sequence encoding a reporter gene that is operably linked to a tissue protective cytokine receptor complex-responsive promoter and (ii) expresses a tissue protective cytokine receptor complex, and determining the level of activity of a tissue protective cytokine receptor complex by measuring the level of reporter gene expression, such that if the level of reporter gene activity in the presence of the compound increases or decreases relative to the level of reporter gene activity in the absence of the compound, then a compound that modulates the activity of a tissue protective cytokine receptor complex is identified.

In another embodiment, the invention provides for method for identifying a compound that binds to a tissue protective cytokine receptor complex, comprising contacting a tissue protective cytokine receptor complex with (i) a tissue protective cytokine receptor complex ligand attached to a first label and (ii) an equivalent amount of a test compound attached to a second label under conditions conducive to binding, removing unbound material from the tissue protective cytokine receptor complex, and detecting the level of the first and second labels wherein if the second label is present the compound binds the complex and if the level of the first label decreases relative to the level of the first label where the labeled ligand is contacted with a tissue protective cytokine receptor complex under conditions conducive to binding in the absence of a test compound after removal of unbound material, then a compound that binds to a tissue protective cytokine receptor complex y is identified.

In yet another embodiment, the invention provides for method for identifying a compound that modulates the binding of a tissue protective cytokine receptor complex ligand to a tissue protective cytokine receptor complex, comprising contacting a tissue protective cytokine receptor complex ligand with a tissue protective cytokine receptor complex in the presence of one or more test compounds under conditions conducive to binding, and measuring the amount of tissue protective cytokine receptor complex ligand bound to the tissue protective cytokine receptor complex, such that if the amount of bound tissue protective cytokine receptor complex ligand measured in the presence of the one or more test compounds differs from the amount of bound tissue protective cytokine receptor complex ligand measured in the absence of the one or more test compounds, then a compound that modulates the binding of a tissue protective cytokine receptor complex ligand to the tissue protective cytokine receptor complex is identified.

In certain embodiments of the methods of the invention described herein above where binding of a tissue protective cytokine receptor complex contacted with a tissue protective cytokine receptor complex ligand is measured, the amount of bound tissue protective cytokine receptor complex ligand is measured using a tissue protective cytokine receptor complex ligand-specific antibody.

In certain embodiments of the methods of the invention described herein above where binding of a tissue protective cytokine receptor complex contacted with a tissue protective cytokine receptor complex ligand is measured, the tissue protective cytokine receptor complex ligand is labeled and binding of the tissue protective cytokine receptor complex ligand to the tissue protective cytokine receptor complex is measured by detecting the label attached to the tissue protective cytokine receptor complex ligand.

In certain embodiments of the methods of the invention described herein above where binding of a tissue protective cytokine receptor complex contacted with a tissue protective cytokine receptor complex ligand is measured, the tissue protective cytokine receptor complex ligand is labeled and binding of the labeled ligand to the tissue protective cytokine receptor complex is measured by detecting the label attached to the tissue protective cytokine receptor complex ligand. In related embodiments, the label is fluorescent.

In one embodiment, the invention provides for a method for identifying a compound that modulates the interaction between a tissue protective cytokine receptor complex and a tissue protective cytokine receptor complex ligand, comprising contacting a tissue protective cytokine receptor complex with one or more test compounds, and measuring the tissue protective cytokine receptor complex activity, such that if the activity measured in the presence of the one or more test compounds differs from the tissue protective cytokine receptor complex activity in the absence of the one or more test compounds, then a compound that modulates the interaction between the tissue protective cytokine receptor complex and the tissue protective cytokine receptor complex ligand is identified.

In certain embodiments of the methods of the invention described herein above where tissue protective cytokine receptor complex activity is measured, such activity is measured by cell proliferation or cell differentiation.

In certain embodiments of the methods of the invention described herein above where tissue protective cytokine receptor complex activity is measured, such activity measured is the ability of the tissue protective cytokine receptor complex to interact with a tissue protective cytokine receptor complex ligand.

In certain embodiments of the methods of the invention described herein above where tissue protective activity is assayed, the step of assaying the identified compound for tissue protective activity comprises detecting the presence of nucleolin in the cell.

In certain embodiments of the methods of the invention described herein above where tissue protective activity is assayed, the step of assaying the identified compound for tissue protective activity comprises detecting or measuring an increased level of activity of neuroglobin or cytoglobin in a cell.

In certain embodiments of the methods of the invention described herein above where a test compound is contacted with a tissue protective cytokine receptor complex, the tissue protective cytokine receptor complex contacted to the test compound is on a cell surface. In one embodiment, the tissue protective cytokine receptor complex is immobilized to a solid surface. In certain embodiments of the methods of the invention described herein above the solid surface is a microtiter dish. In certain embodiments of the methods of the invention described herein above, the solid surface is a chip.

In one embodiment, the tissue protective cytokine receptor complex is in solution. In one embodiment, the tissue protective cytokine receptor complex is in a cell. In one embodiment, the tissue protective cytokine receptor complex is on an isolated cell membrane.

In certain embodiments of the methods of the invention described herein above, the compound inhibits the binding of a tissue protective cytokine receptor complex ligand to a tissue protective cytokine receptor complex. In another embodiment, the compound enhances the binding of a tissue protective cytokine receptor complex ligand to a tissue protective cytokine receptor complex.

The invention further provides for a method for identifying a compound that binds a tissue protective cytokine receptor complex, comprising contacting a test compound with a ligand-binding tissue protective receptor complex fragment comprising at least one EPO receptor extracellular domain and at least one β common receptor extracellular domain fused to an $F_c$ fragment attached to a solid support, and removing unbound test compounds from the solid support, identifying the compound attached to the tissue protective cytokine receptor complex fragment, such that a compound bound to the solid support is identified as a compound that binds to a tissue protective cytokine receptor complex.

In certain embodiments of the methods of the invention described herein above, the test compound is an antibody specific for the tissue protective cytokine receptor complex. In one embodiment, the test compound is an antibody is specific for a tissue protective cytokine receptor complex ligand. In one embodiment, the test compound is a small molecule. In one embodiment, the test compound is a peptide. In one embodiment, the test compound is a member of a library.

In certain embodiments of the methods of the invention described herein above, the tissue protective cytokine receptor complex ligand is an EPO.

In certain embodiments of the methods of the invention described herein above, the compound binds the tissue protective cytokine receptor complex. In certain embodiments of the methods of the invention described herein above, the compound binds the tissue protective cytokine receptor complex ligand.

3.1 Terminology

As used herein, the term "tissue protective activity" refers to the effect of inhibiting or delaying damage or death of a cell, tissue, or organ. The tissue protective activity can be against various conditions, diseases, and cellular, organ, and/or tissue damage, for example, those described in section 5.5. Tissue protective activity may be specific to excitable tissue, cells, and/or organs having a tissue protective cytokine receptor complex, such as tissues of the central nervous system.

The term "tissue protective cytokine receptor complex" as used herein means a complex comprising at least one erythropoietin receptor and at least one beta common receptor. The tissue protective cytokine receptor complex may contain multiple erythropoietin receptors and/or beta common receptors, as well as other types of receptors as described herein in section 5.1.3

The term "tissue protective cytokine receptor complex ligand" means any compound that binds a tissue protective cytokine receptor complex and activate the complex. A "tissue protective cytokine receptor complex ligand" can be any type of compound, such as, but not limited to, proteins, peptides, small molecules, organic molecules, or non-organic molecules. Non-limiting examples of tissue protective cytokine receptor complex ligands include EPO, including mutants, chemical modifications, or tissue protective cytokine receptor complex-binding fragments thereof. Another example of a tissue protective cytokine receptor complex ligand is an antibody specific for the complex.

4. BRIEF DESCRIPTION OF THE FIGURES

Figure 8:
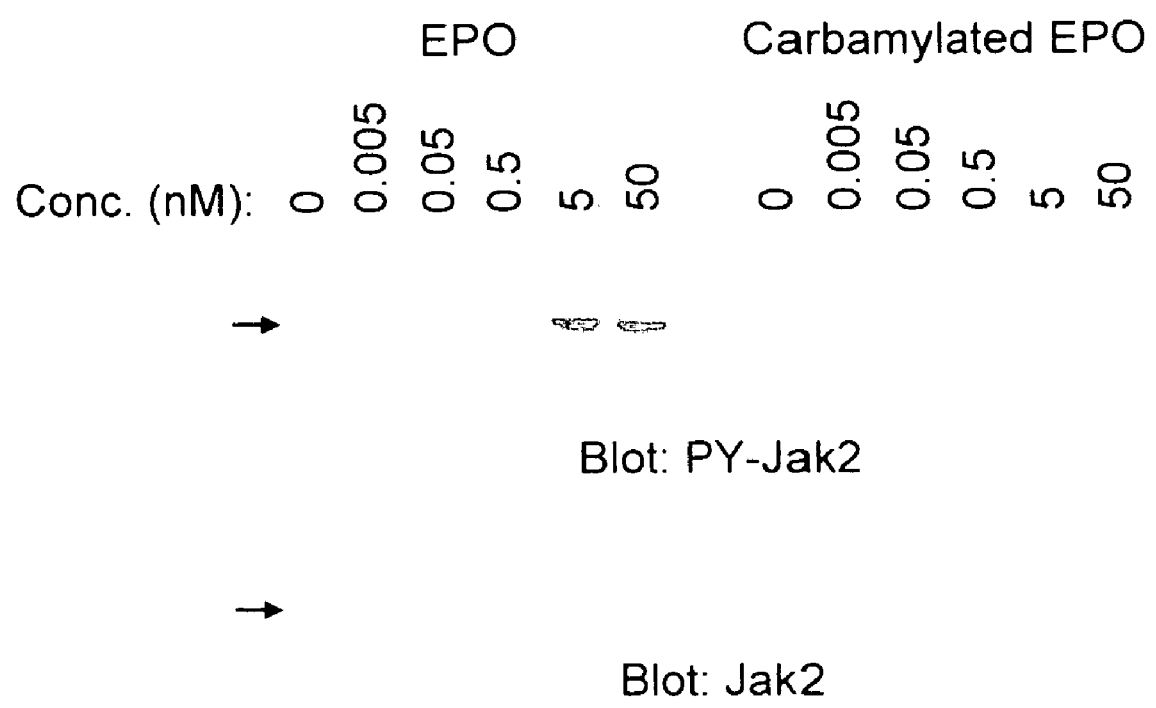

FIG. 8 shows photographs of Western blotting of the cell proteins separated by polyacrylamide gels using PY-Jak2 antibodies. The top gel shows that phosphorylated Jak2 was present in cells stimulated with EPO at 5 nM and 50 nM concentrations. The bottom gel shows a control performed where membranes were stripped and reprobed with an antibody against Jak2 to confirm equal loading.

Figure 9:
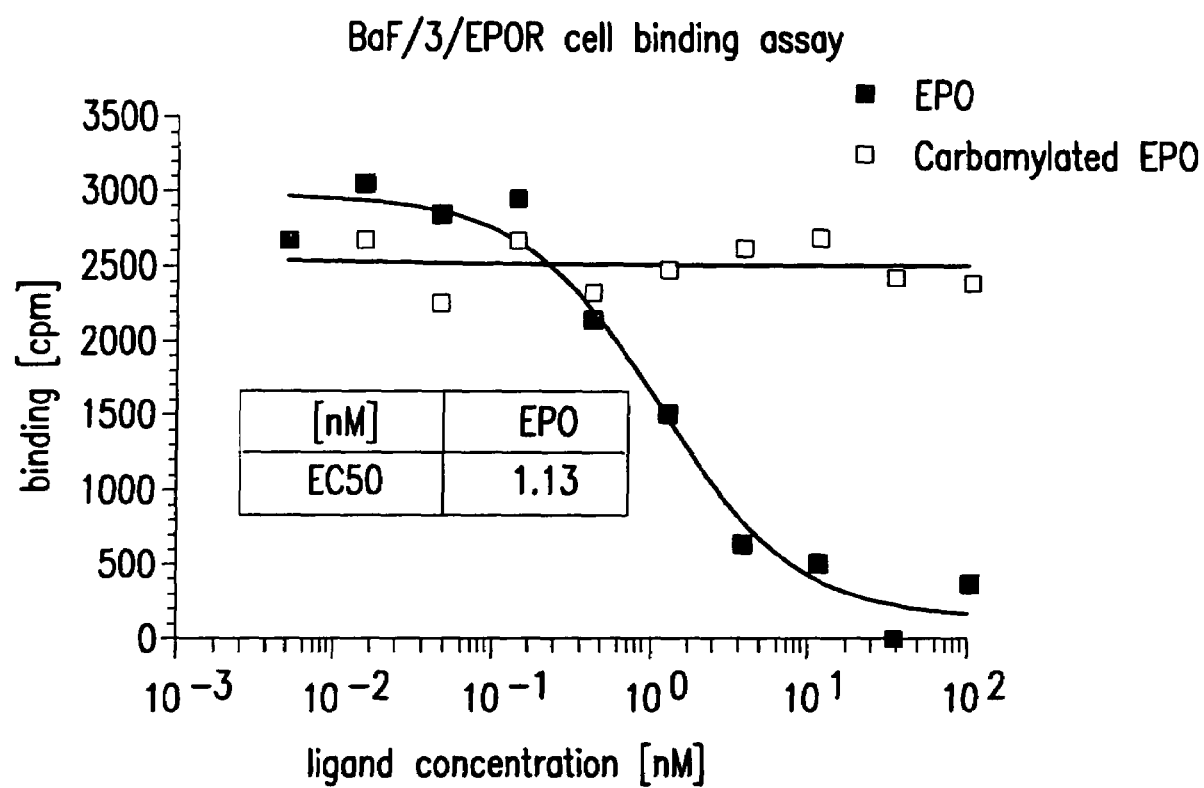

FIG. 9 shows a graph of ligand binding affinity for BaF3 cells expressing the EPO receptor. Ligand concentration in nM (x-axis) is plotted against binding (cpm) (y-axis) for BaF3 EPO receptor expressing cells contacted with EPO receptor ligands EPO and carbamylated EPO.

Figure 10:
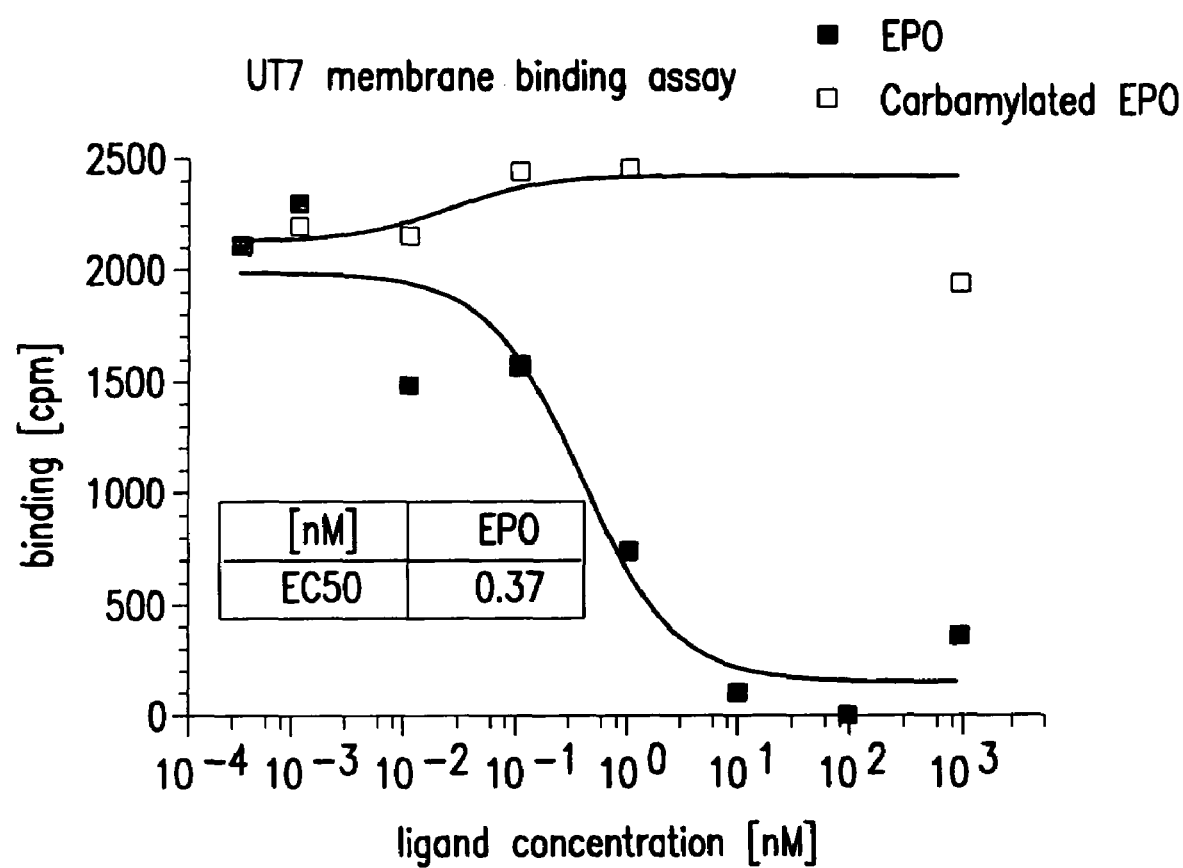

FIG. 10 shows a graph of ligand binding affinity for UT-7 cell membranes having the EPO receptor. Ligand concentration in nM (x-axis) is plotted against binding (cpm) (y-axis) for UT-7 EPO receptor expressing cell membranes contacted with EPO receptor ligands EPO and carbamylated EPO.

Figure 11B:
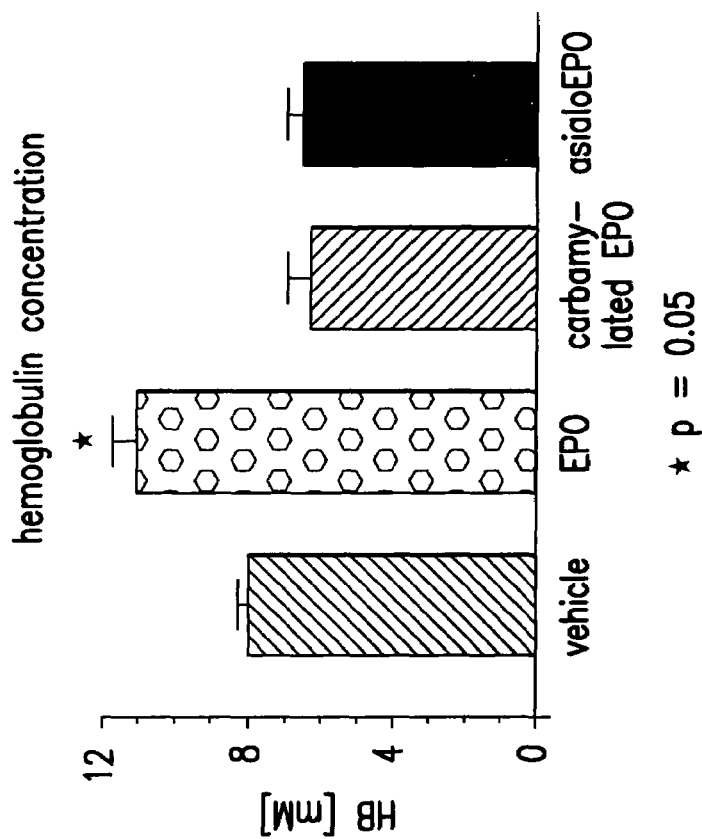
Figure 11A:
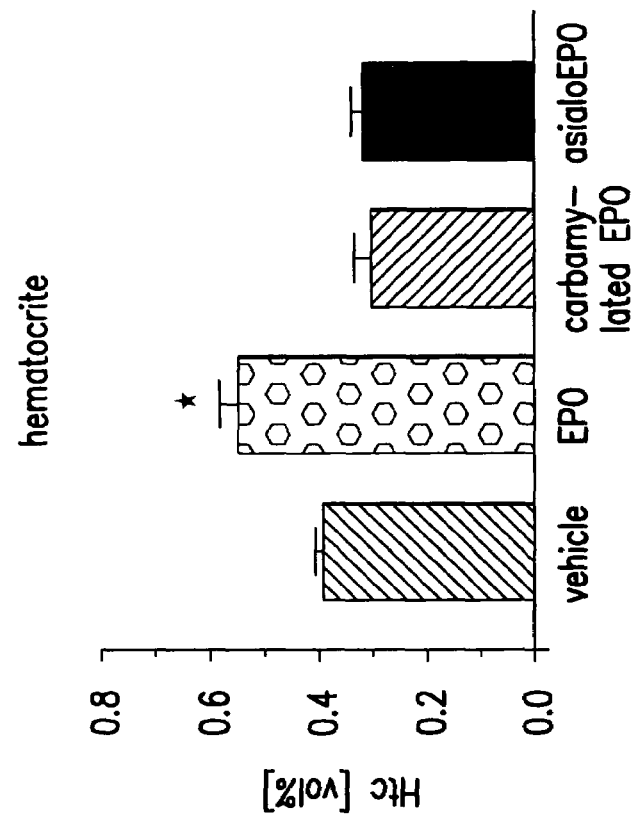

FIG. 11 shows histograms of, 11A, hematocrit levels as measured by the percent volume of hematocrit (y-axis), and, 11B, hemoglobin levels measured in concentration in mM (y-axis), in mice after administration of control (vehicle), EPO, carbamylated EPO, and asialoEPO (x-axis).

Figure 12:
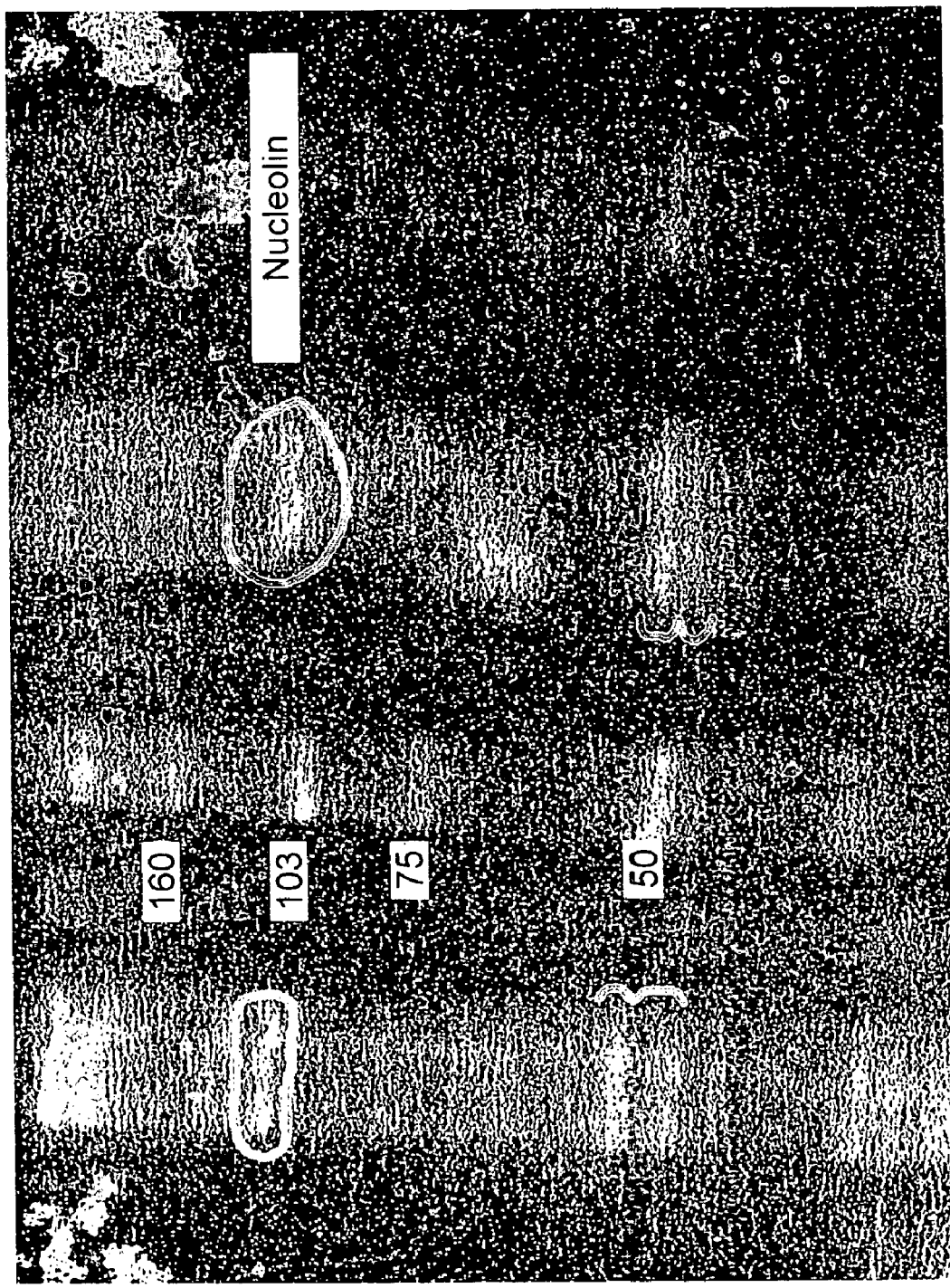

FIG. 12 shows a photograph of the SDS-PAGE gel with a 103 KD nucleolin protein circled.

5. DETAILED DESCRIPTION OF THE INVENTION

The present invention is directed to methods for use of a heteromultimer receptor complex that mediates the tissue protective activities of tissue protective compounds. The invention provides screening methods to identify such tissue protective compounds. The invention is based on the discovery by the inventors that EPO receptor forms a complex with $β_c$ receptor within excitable cells and tissues such as brain, spinal cord and heart. The complex consists of at least one EPO-R in a complex with at least one $β_c$ receptor. In addition to the $β_c$ receptor, other signal transducing receptors may be used including, but not limited to, the $γ_c$ receptor and GP130, segments and portions of other Type-1 cytokine receptors, including, but not limited to, GM-CSF, IL-3, IL-5, etc., and orphan receptors, including, but not limited to, ROR1, NR6, HM74, etc. The screening methods of the invention may use such tissue protective cytokine receptor complexes in assays for identifying compounds that modulate the activity of a tissue protective cytokine receptor complex. Such assays include binding assays to identify compounds that bind to a tissue protective cytokine receptor complex or a ligand thereof.

Activation of a tissue protective cytokine receptor complex may lead to the upregulation of the production of protective proteins, including, but not limited to, nucleolin and globins such as neuroglobins and cytoglobin (histoglobin). Accordingly, the screening methods for identifying compounds with tissue protective activity may utilize detection of such upregulated proteins.

This receptor complex and downstream regulators may be used in assays to identify tissue protective compounds, including, but not limited to, small molecules and biologics. The compounds identified using these assays can be used to treat various conditions of the central and peripheral nervous systems as well as those of other erythropoietin-responsive cells, tissues, and organs.

5.1 The Tissue Protective Cytokine Receptor Complex

The receptor complex for use in the methods of the invention comprises at least one EPO receptor and at least one $\beta_c$ receptor. Various types of naturally-occurring, modified, and/or mutant EPO receptors and $\beta_c$ receptors may be combined to form such complexes of varying numbers of receptors. Non-limiting examples of tissue protective cytokine receptor complexes are described below.

5.1.1 EPO-R

Mammalian EPO-R may be used in the present invention. EPO-R cDNA has been isolated from mouse liver, Tojo et al., 1987, Biochem. Biophys. Res. Comm. 148: 443-48 and from human fetal liver (Jones et al., 1990, Blood 76:31-35; Winkelmann et al., 1990, Blood 76:24-30). This human cDNA encodes a polypeptide chain of about 55 kDa MW and has about 508 amino acids. Other genomic clones of human EPO-R that have been isolated and sequenced are also contemplated by the present invention (Penny and Forget, 1991, Genomics 11:974-80; Noguchi et al., 1991, Blood 78:2548-2556). The common structure of these EPO-R consist of about 24 amino acid residues in a signal peptide, about 226 amino acids in an extracellular domain, about 23 amino acids in a membrane-spanning domain, and about 235 amino acids in a cytoplasmic domain (D'Andrea and Zon, 1990, J. Clin. Invest., 86:681-687; Jones et al., 1990, Blood, 76:31-35; Penny and Forget, 1991, Genomics, 11:974-80). The mature human EPO-R protein has about 484 amino acids. EPO-R is commercially available from BD Biosciences Clonetech (Palo Alto, Calif.) and has gene bank accession number M60459 and SwissProt accession number P19235.

The forms of EPO-R useful in the practice of the present invention encompass naturally occurring, synthetic and recombinant forms of human and other mammalian EPO-R related molecules. In addition, EPO-R forms useful in the practice of the present invention include proteins that represent functionally equivalent gene products. Such a functionally equivalent gene products include mutant EPO-R and chemically modified EPO-R. Mutant EPO-R may contain deletions, including internal deletions, additions, including additions yielding fusion proteins, or conservative substitutions of amino acid residues within and/or adjacent to the amino acid sequence, but that result in a "silent" change, in that the change produces a functionally equivalent EPO-R. Such amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids including glycine, serine, threonine, cysteine, tyrosine, asparagine, and glutamine; positively charged (basic) amino acids include arginine, lysine, and histidine; and negatively charged (acidic) amino acids include aspartic and glutamic acid. Other known EPO-R mutations such as those disclosed in U.S. Pat. No. 5,292,654 are encompassed by the present invention as well.

Further, soluble (truncated) forms of the EPO receptor containing only the extracellular domain are also contemplated for use in the present invention such as those disclosed in Harris et al. 1992, J. Biol. Chem. 267:15205; Yang & Jones, 1993, Blood 82:1713; and U.S. Patent Application Publication No. 20020031806.

5.1.2 $\beta_c$ Receptor

The $\beta_c$ receptor is typically identified as a signaling receptor subunit associated with human GM-CSF, IL-3 and IL-5. In addition to these cytokines, the $\beta_c$ receptor has been demonstrated to bind EPO-R in certain instances. The conserved region of the $\beta_c$ receptor constitutes all or part of the extracellular ligand-binding region and is about 200 amino acid residues long. The present invention is based, in part, on the demonstration by the Applicants that the EPO-R and $\beta_c$ receptor co-exist within several excitable cells, such as the brain (see FIG. 2) and spinal cord (see FIGS. 3 and 4).

The forms of $\beta_c$ receptor useful in the practice of the present invention encompass naturally occurring, synthetic and recombinant forms of human and other mammalian $\beta_c$ receptor related molecules. In addition, $\beta_c$ receptor forms useful in the practice of the present invention include proteins that represent functionally equivalent gene products. Such functionally equivalent gene products may include mutant $\beta_c$ receptor and chemically modified $\beta_c$ receptor. The mutant $\beta_c$ receptors may contain deletions, including internal deletions, additions, including additions yielding fusion proteins, or conservative substitutions of amino acid residues within and/or adjacent to the amino acid sequence, but that result in a "silent" change, resulting in a functionally equivalent $\beta_c$ receptor. Mutated $\beta_c$ receptors include, but are not limited to, I374N, FIΔ, ΔGA, H544R, V449, A459D, L445Q, CRD4 point mutations (I374N, L356P, W358N, Q375P, Y376N, W383R, and L399P), and extracellular truncations (1 GH7). (See R. J. D'Andrea and T. J. Gonda, 2000, Experimental Hematology 28:231-243; D'Andrea et al., 1998, J. Clin. Invest. 102:1951-1960; Jenkins et al., 1999, J. Biol. Chem. 274:8669-8677).

It is also contemplated that other known signaling receptor subunits including, but not limited to, $\gamma_c$ receptor and GP-130, and orphan receptors may be used with the present invention as well.

5.1.3 Structure of the Heteromultimer Receptor Complex

The $\beta_c$ receptor forms a multimer with many of the receptors it was previously known to bind with, i.e., GM-CSF, IL-3, and IL-5. For example, the receptor complex for GM-CSF consists of GM-CSF receptor, two $\beta_c$ receptors, and the GM-CSF ligand. The EPO-R has been known to form a complex with the $\beta_c$ Receptor. (See Yutaka et al., 1995, Biochem. Biophy. Res. Com. 208:1060-1066; Jubinsky et al., 1997, Blood, 90:1867-1873; D'Andrea et al., 1998, J. Clin, Invest. 102:1951-1960.) Similarly, according to the present invention, the $\beta_c$ receptor forms a heteromultimer with the EPO-R to form a tissue protective receptor complex. This is based on immunoprecipitation studies demonstrating that the $\beta_c$ receptor and EPO-R receptors coprecipitate (see FIG. 5).

Figure 6:
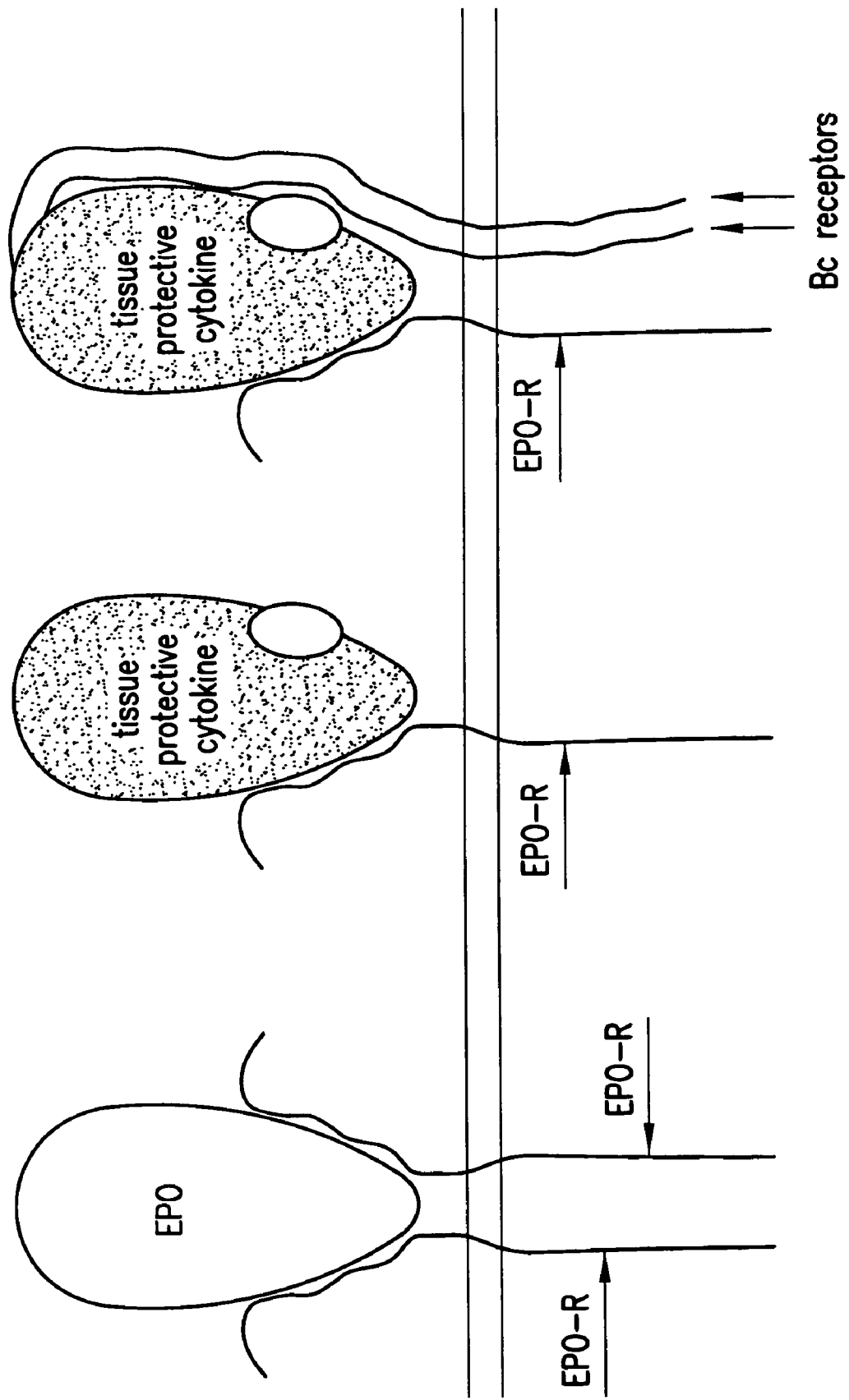
FIG. 6 shows the potential configuration of the tissue protective receptor complex.

This tissue protective receptor complex includes at least one EPO-R and at least one $\beta_c$ receptor. Preferably, as depicted in FIG. 6, the tissue protective receptor complex will include greater than one $\beta_c$ receptor. Tissue protective receptor complex configurations are also contemplated by the present invention that include greater that one EPO-R. Examples of tissue protective receptor complexes contemplated by the present invention include, but are not limited to, EPO-R$_2$/$\beta_c$ receptor$_2$, EPO-R/$\beta_c$ receptor$_2$, and EPO-R/$\beta_c$ receptor$_3$. The most suggested configuration of the tissue protective receptor complex is EPO-R/$\beta_c$ receptor$_2$ as depicted in FIG. 6. As shown therein, without being bound by any particular theory, a possible mechanism by which the tissue protective compound binds to the tissue protective receptor complex involves the tissue protective compound first binding with the EPO-R and then subsequently two $\beta_c$ receptors binding to the complex. This depiction is merely illustrative of one method by which a ligand may bind to the tissue protective receptor complex and those of ordinary skill in the art could reasonably envision other mechanisms by which binding can occur—the receptor complex may be preformed (EPO-R and two $\beta_c$ receptor) prior to binding the ligand, etc.

The receptor polypeptides of the present invention, including full-length receptors, receptor fragments (e.g. ligand-binding fragments), and fusion polypeptides can be produced in genetically engineered host cells according to conventional techniques. For example, Erythropoietin binding fragments of the EPO receptor have been identified (Barone et al., J. Biol. Chem. 272:4985-4992). Such fragments that also complex with a $\beta_c$ receptor may be used in the screening methods of the invention.

5.2 Screening Assays

Tissue protective cytokine receptor complexes, such as, but not limited to, those described above can be used in screening assays to identify compounds having a tissue protective activity. Compounds identified in these assays may bind to a tissue protective cytokine receptor complex, modulate the activity of a complex, or modulate the interaction of a tissue protective cytokine receptor complex ligand and the complex. In addition, the compounds identified may themselves have a tissue protective activity.

This invention is particularly useful for screening compounds by using an EPO receptor-$\beta_c$ receptor complex in any of a variety of drug screening techniques. The receptor complex employed in such a test may either be free in solution, affixed to a solid support, borne on a cell surface or located intracellularly. One method of drug screening utilizes eukaryotic cells which are stably transformed with recombinant nucleic acids expressing the polypeptide or fragment. Drugs are screened against such transformed cells in competitive binding assays. Such cells, either in viable or fixed form, can be used for standard binding assays. One may measure, for example, the formation of complexes between receptor and the agent being tested or examine the diminution in complex formation between the tissue protective cytokine receptor complex and an appropriate cell line, which are well known in the art. For example, see examples sections 6 and 7 below.

The tissue protective cytokine receptor complexes described above in section 5.1 can similarly be used in assays to determine biological activity, including in a panel of multiple receptors for high-throughput screening, as a reagent (including the labeled reagent) in assays designed to quantitatively determine levels of a tissue protective compound in biological fluids, as markers for tissues in which the corresponding tissue protective compound is preferentially expressed (either constitutively or at a particular stage of tissue differentiation or development or in a disease state), and, of course, to isolate correlative ligands.

Methods for performing the assays listed above are well known to those skilled in the art. References disclosing such methods include without limitation "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

In certain embodiments, the assays of the invention described herein may be used to identify a compound that interacts with a tissue protective cytokine receptor complex. Such assays may be carried out in the absence of a tissue protective cytokine receptor complex ligand. The interaction may be, for example, binding of the test compound to tissue protective cytokine receptor complex or activity of a tissue protective cytokine receptor complex. In such embodiments, the test compound is contacted with a tissue protective cytokine receptor complex. The compound identified is one that produces a readout, such as, but not limited to, activation of the tissue protective cytokine receptor complex, transcription of a reporter gene, cell proliferation, or a tissue protective activity. Such assays are typically performed with a control, wherein the compound is not contacted to the tissue protective cytokine receptor complex. Where there is a difference in the readout with and without the compound, a compound that interacts with the tissue protective cytokine receptor complex is identified. Alternatively, standard levels of readout, such as, but not limited to, activity of the tissue protective cytokine receptor complex, can be measured prior to contacting the tissue protective cytokine receptor complex with the test compound, and the difference in readout before and after addition of the compound can be used to identify compounds.

In certain other embodiments, the assays of the invention may be used to identify compounds that modulate, i.e., enhance or interfere with, the interaction between a tissue protective cytokine receptor complex ligand and a tissue protective cytokine receptor complex. Such assays may be carried out in the presence of a tissue protective cytokine receptor complex ligand, such as EPO or an antibody specific to the tissue protective cytokine receptor complex. In such embodiments, the difference in the level of readout in the presence and absence of the test compound may be detected. The level of readout can then be compared to that in the absence of EPO. If the difference in the level of readout detected with and without the compound is dependent on the presence of EPO, then a compound that modulates the interaction of a tissue protective cytokine receptor complex with its ligand is identified. For example, if the difference in level of readout detected results from an increase in readout in the presence of a compound, wherein the increase is dependent on the presence of EPO, an agonist of the interaction between a tissue protective cytokine receptor complex and its ligand is identified. Alternatively, if the difference in level of readout detected results from an decrease in readout in the presence of a compound, wherein the decrease is dependent on the presence of EPO, then an antagonist of the interaction between a tissue protective cytokine receptor complex and its ligand is identified. The situation is reversed in embodiments where the readout is a negative readout. For example, a readout may be present when a compound has no effect on the tissue protective cytokine receptor complex and is absent when a compound with such an effect is incorporated into the assay, then a negative readout may indicate that a compound with the desired effect has been identified.

Any or all of these assays that utilize a tissue protective cytokine receptor complex are capable of being developed into reagent grade or kit format for commercialization as research and/or clinical products.

5.2.1 Cell-Free Assays

The tissue protective cytokine receptor complexes described herein above may be used in cell-free assays to identify compounds having a tissue protective activity. In certain embodiments of cell-free assays, the tissue protective cytokine receptor complexes may be free in solution or attached to a solid support. The activity of a tissue protective cytokine receptor complex may be measured in a variety of ways. For example, activity may be the compound's ability to bind a tissue protective cytokine receptor complex or the binding affinity of a tissue protective cytokine receptor complex and a compound. In certain embodiments, the tissue protective cytokine receptor complex is added to binding assays in the form of isolated membranes containing the tissue protective cytokine receptor complex.

In a direct binding assay, either the ligand and/or the tissue protective cytokine receptor complex is contacted with a test compound under conditions that allow binding of the test compound to the ligand or the receptor. The binding may take place in solution or on a solid surface. Preferably, the test compound is previously labeled for detection. Any detectable compound may be used for labeling, such as but not limited to, a luminescent, fluorescent, or radioactive isotope or group containing same, or a nonisotopic label, such as an enzyme or dye. After a period of incubation sufficient for binding to take place, the reaction is exposed to conditions and manipulations that remove excess or non-specifically bound test compound. Typically, it involves washing with an appropriate buffer. Finally, the presence of a ligand bound to the test compound (e.g., EPO-test compound) or a the tissue protective cytokine receptor complex bound to the test compound is detected.

In a competition binding assay, test compounds are assayed for their ability to disrupt or enhance the binding of the ligand (e.g., EPO) to the tissue protective cytokine receptor complex. Labeled ligand (e.g., EPO or carbamylated EPO) may be mixed with the tissue protective cytokine receptor complex or a fragment thereof, and placed under conditions in which the interaction between them would normally occur, with and without the addition of the test compound. The amount of labeled ligand (e.g., EPO) that binds the tissue protective cytokine receptor complex may be compared to the amount bound in the presence or absence of test compound.

In a preferred embodiment, to facilitate complex formation and detection, the binding assay is carried out with one or more components immoblilized on a solid surface. In various embodiments, the solid support could be, but is not restricted to, polycarbonate, polystyrene, polypropylene, polyethlene, glass, nitrocellulose, dextran, nylon, polyacrylamide and agarose. The support configuration can include beads, membranes, microparticles, the interior surface of a reaction vessel such as a microtiter plate, test tube or other reaction vessel. The immobilization of the tissue protective cytokine receptor complex, or other component, can be achieved through covalent or non-covalent attachments. In one embodiment, the attachment may be indirect, i.e. through an attached antibody. In another embodiment, the tissue protective cytokine receptor complex and negative controls are tagged with an epitope, such as glutathione S-transferase (GST) so that the attachment to the solid surface can be mediated by a commercially available antibody such as anti-GST (Santa Cruz Biotechnology).

For example, such an affinity binding assay may be performed using a tissue protective cytokine receptor complex which is immobilized to a solid support. Typically, the non-mobilized component of the binding reaction, in this case either ligand (e.g., EPO or carbamylated EPO) or the test compound, is labeled to enable detection. A variety of labeling methods are available and may be used, such as luminescent, chromophore, fluorescent, or radioactive isotope or group containing same, and nonisotopic labels, such as enzymes or dyes. In a preferred embodiment, the test compound is labeled with a fluorophore such as fluorescein isothiocyanate (FITC, available from Sigma Chemicals, St. Louis).

The labeled test compounds, or ligand (e.g., EPO or carbamylated EPO) plus test compounds, are then allowed to contact with the solid support, under conditions that allow specific binding to occur. After the binding reaction has taken place, unbound and non-specifically bound test compounds are separated by means of washing the surface. Attachment of the binding partner to the solid phase can be accomplished in various ways known to those skilled in the art, including but not limited to chemical cross-linking, non-specific adhesion to a plastic surface, interaction with an antibody attached to the solid phase, interaction between a ligand attached to the binding partner (such as biotin) and a ligand-binding protein (such as avidin or streptavidin) attached to the solid phase, and so on.

Preferably, the tissue protective cytokine receptor complex is added to binding assays in the form of intact cells that express the tissue protective cytokine receptor complex (see assays described in the sections 5.2.2), or isolated membranes containing the tissue protective cytokine receptor complex. Thus, direct binding to the tissue protective cytokine receptor complex or the ability of a test compound to modulate a ligand-tissue protective cytokine receptor complex (e.g., EPO-tissue protective cytokine receptor complex) may be assayed in intact cells in culture or in animal models in the presence and absence of the test compound. A labeled ligand (e.g., EPO or carbamylated EPO) may be mixed with crude extracts obtained from such cells, and the test compound may be added. Isolated membranes may be used to identify compounds that interact with the tissue protective cytokine receptor complex. For example, in a typical experiment using isolated membranes, cells may be genetically engineered to express the tissue protective cytokine receptor complex. Membranes can be harvested by standard techniques and used in an in vitro binding assay. Labeled ligand (e.g., $^{125}$I-labeled EPO) is bound to the membranes and assayed for specific activity; specific binding is determined by comparison with binding assays performed in the presence of excess unlabeled (cold) ligand.

The soluble tissue protective cytokine receptor complex ligand may also be recombinantly expressed and utilized in non-cell based assays to identify compounds that bind to the tissue protective cytokine receptor complex ligand. Alternatively, a ligand binding domain of the recombinantly expressed tissue protective cytokine receptor complex, or a fragment of the tissue protective cytokine receptor complex, can be used in the non-cell based screening assays. In another alternative embodiment, peptides corresponding to one or more of the binding domains of the tissue protective cytokine receptor complex, or fusion proteins containing one or more of the binding domains of the tissue protective cytokine receptor complex can be used in non-cell based assay systems to identify compounds that bind to the cytoplasmic portion of the tissue protective cytokine receptor complex; such compounds may be useful to modulate a signal transduction pathway of the tissue protective cytokine receptor complex. In non-cell based assays the recombinantly expressed tissue protective cytokine receptor complex is attached to a solid substrate such as a test tube, microtiter well or a column, by means well known to those in the art (see Ausubel et al., 1998, Current Protocols in Molecular Biology, John Wiley & Sons, NY). The test compounds are then assayed for their ability to bind to the tissue protective cytokine receptor complex.

Alternatively, the binding reaction may be carried out in solution. In this assay, the labeled component is allowed to interact with its binding partner(s) in solution. If the size differences between the labeled component and its binding partner(s) permit such a separation, the separation can be achieved by passing the products of the binding reaction through an ultrafilter whose pores allow passage of unbound labeled component but not of its binding partner(s) or of labeled component bound to its partner(s). Separation can also be achieved using any reagent capable of capturing a binding partner of the labeled component from solution, such as an antibody against the binding partner, a ligand-binding protein which can interact with a ligand previously attached to the binding partner, and so on.

In one embodiment, for example, a phage library can be screened by passing phage from a continuous phage display library through a column containing purified tissue protective cytokine receptor complex, or a fragment, or domain, thereof, linked to a solid phase, such as plastic beads. By altering the stringency of the washing buffer, it is possible to enrich for phage that express peptides with high affinity for the tissue protective cytokine receptor complex. Phage isolated from the column can be cloned and the affinities of the short peptides can be measured directly. Sequences for more than one oligonucleotide can be combined to test for even higher affinity binding to the tissue protective cytokine receptor complex or its complex with its ligand. Knowing which amino acid sequences confer the strongest binding to the tissue protective cytokine receptor complex, computer models can be used to identify the molecular contacts between the tissue protective cytokine receptor complex and the test compound. This will allow the design of non-protein compounds which mimic those contacts. Such a compound may have the same activity of the peptide and can be used therapeutically, having the advantage of being efficient and less costly to produce.

In another specific embodiment of this aspect of the invention, the solid support is membranes containing the tissue protective cytokine receptor complex attached to a microtiter dish. Test compounds, for example, cells that express library members, are cultivated under conditions that allow expression of the library members in the microtiter dish. Library members that bind to the protein (or nucleic acid or derivative) are harvested. Such methods, are described by way of example in Parmley and Smith, 1988, Gene 73:305-318; Fowlkes et al., 1992, BioTechniques 13:422-427; PCT Publication No. WO 94/18318; and in references cited hereinabove.

Finally, the label remaining on the solid surface may be detected by any detection method known in the art. For example, if the test compound is labeled with a fluorophore, a fluorimeter may be used to detect complexes.

Various in vitro assays can be used to identify and verify the ability of a compound to bind a tissue protective cytokine receptor complex, to modulate the interaction of a tissue protective cytokine receptor complex and a tissue protective cytokine receptor complex ligand, or modulate the activity of a tissue protective cytokine receptor complex.

In another embodiment of the present invention, interactions between the tissue protective cytokine receptor complex or ligand (e.g., EPO or carbamylated EPO) and a test compound may be assayed in vitro. Known or unknown molecules are assayed for specific binding to the tissue protective cytokine receptor complex, or fragments thereof, under conditions conducive to binding, and then molecules that specifically bind to the tissue protective cytokine receptor complex are identified. The two components can be measured in a variety of ways. One approach is to label one of the components with an easily detectable label, place it together with a test component(s) under conditions that allow binding to occur, perform a separation step which separates bound labeled component from unbound labeled component, and then measure the amount of bound component. In one embodiment, the tissue protective cytokine receptor complex can be labeled and added to a test agent, using conditions that allow binding to occur. Binding of the test agent can be determined using polyacrylamide gel analysis to compare complexes formed in the presence and absence of the test agent.

Multiple in vitro assays can be performed simultaneously or sequentially to assess the effect of a compound on a tissue protective cytokine receptor complex-mediated process. The assessment can be made by measuring or detecting tissue protective cytokine receptor complex activity, for example, binding of a test compound to a tissue protective cytokine receptor complex, cell proliferation, cell differentiation, and upregulation of a protective protein, e.g., globin. In a preferred embodiment, the in vitro assays described herein are performed in a high throughput format (e.g., in microtiter plates).

5.2.2 Cell-Based Assays

A tissue protective cytokine receptor complex may be expressed in a cultured cell, and the cell can then be used to screen for ligands for the receptor complex, including the natural ligand, as well as agonists and antagonists of the natural ligand.

To summarize the approach to the cell-based assay, a cDNA or gene encoding the receptor is combined with other genetic elements required for its expression (e.g., a transcription promoter), and the resulting expression vector is inserted into a host cell. A vector encoding an EPO receptor or a β common receptor may be synthesized and used to transform or transfect a host cell with the vector of interest for use in the methods of the invention. The use of stable transformants is preferred.

Cells that express the DNA and produce functional receptor are selected and used with one of a variety of possible screening systems, as further disclosed below.

An example of a cell-based method for identifying a compound that modulates the interaction of a tissue protective cytokine receptor complex and a ligand thereof comprises the following steps: (a) contacting a test compound with the ligand and an tissue protective cytokine receptor complex-expressing cell; and (b) measuring the level of tissue protective cytokine receptor complex activity in the cell, such that if the level of activity measured in (b) differs from the level of tissue protective cytokine receptor complex activity in the absence of the test compound, then a compound that modulates the interaction of a tissue protective cytokine receptor complex and its ligand is identified.

Alternatively, cell-based assays may be used to identify compounds that interact with a tissue protective cytokine receptor complex. For example, a test compound can be contacted with a tissue protective cytokine receptor complex-expressing cell and the activity of the tissue protective cytokine receptor complex, as measured by binding affinity, cell proliferation, or the presence of a reporter gene transcript, can be determined. If the activity of the tissue protective cytokine receptor complex differs, e.g., is increased or decrease, in comparison to the activity of tissue protective cytokine receptor complex in the absence of the test compound, then a compound that interacts with a tissue protective cytokine receptor complex is identified.

Cell-based screening assays are useful for detecting both agonist and antagonist ligands. Agonists (including the natural ligand) and antagonists have enormous potential in both in vitro and in vivo applications. Compounds identified as receptor agonists are useful for stimulating proliferation and development of target cells in vitro and in vivo. For example, agonist compounds are useful as components of defined cell culture media, and may be used alone or in combination with other cytokines and hormones to replace serum that is commonly used in cell culture. Agonists may be useful in specifically promoting the growth and/or development of EPO-responsive cells (including, but not limited to, nervous, heart, and retinal derived cells) in culture. Antagonists are useful as research reagents for characterizing sites of ligand-receptor interaction. In vivo, receptor agonists or antagonists may find application in the treatment of neural, heart and/or retinal diseases. A variety of suitable assays are known in the art. These assays may be based on the detection of a biological response in a target cell.

In one embodiment, binding of ligand (e.g., EPO or carbamylated EPO) to the tissue protective cytokine receptor complex may be assayed in intact cells in animal models. A labeled ligand (e.g., EPO or carbamylated EPO) may be administered directly to an animal, with and without a test compound. A downstream effect of the ligand (e.g., EPO or carbamylated EPO) binding the tissue protective cytokine receptor complex, e.g., tissue protection or cell proliferation, may be measured in the presence and the absence of test compound. For these assays, host cells to which the test compound is added may be genetically engineered to express the tissue protective cytokine receptor complex and/or ligand (e.g., EPO or carbamylated EPO), which may be transient, induced or constitutive, or stable. For the purposes of the screening methods of the present invention, a wide variety of host cells may be used including, but not limited to, tissue culture cells, mammalian cells, and yeast cells. Mammalian cells such as brain cells or other cells that express the tissue protective cytokine receptor complex may be a preferred cell type in which to carry out the assays of the present invention.

5.2.2.1 Cells

In a preferred embodiment, the cell used in the methods of the invention is a mammalian cell. In a more preferred embodiment, the host cell is a human cell. In another embodiment, the host cells are primary cells isolated from a tissue or other biological sample of interest. One skilled in the art would realize that different cell types can be used in the methods of the invention for screening or identify compounds. Cell types used may endogenously express an EPO receptor, a β common receptor, both an EPO receptor and a β common receptor, or no EPO receptor or β common receptor. In a preferred embodiment the host cell is derived from an excitable tissue. In a preferred embodiment the host cell is derived from an excitable neuronal tissue.

By way of non-limiting examples, a responsive or excitable cells may be neuronal, retinal, muscle, heart, lung, liver, kidney, small intestine, adrenal cortex, adrenal medulla, capillary endothelial, testes, ovary, pancreas, bone, skin, or endometrial cells or tissue. Further, non-limiting examples of responsive or excitable cells include photoreceptor (rods and cones), ganglion, bipolar, horizontal, amacrine, Müller, Purkinje, myocardium, pace maker, sinoatrial node, sinus node, junction tissue, atrioventricular node, bundle of His, hepatocytes, stellate, Kupffer, mesangial, renal epithelial, tubular interstitial, goblet, intestinal gland (crypts), enteral endocrine, glomerulosa, fasciculate, reticularis, chromaffin, pericyte, Leydig, Sertoli, sperm, Graffian follicle, primordial follicle, islets of Langerhans, α-cells, β-cells, γ-cells, F-cells, osteoprogenitor, osteoclasts, osteoblasts, endometrial stroma, endometrial, stem and endothelial cells.

Mammalian cells suitable for use in expressing the tissue protective cytokine receptor complex and transducing a receptor-mediated signal include cells that express at least one of the receptor subunits used to form the functional tissue protective receptor complex. These subunits may include those of the class I cytokine receptors. In certain embodiments of the invention, it is also preferred to use a cell from the same species as the receptor to be expressed. Within a preferred embodiment, the cell is dependent upon an exogenously supplied hematopoietic growth factor for its proliferation. In certain preferred embodiments, cell lines of this type are the human TF-1 cell line (ATCC number CRL-2003) and the AML-193 cell line (ATCC number CRL-9589), which are GM-CSF-dependent human leukemic cell lines. In an alternative embodiment, suitable host cells can be engineered to produce the necessary receptor subunit or other cellular component needed for the desired cellular response. For example, the murine cell line BaF3 (Palacios and Steinmetz, 1985, Cell 41:727-734; Mathey-Prevot et al., 1986, Mol. Cell. Biol. 6:4133-4135) or a baby hamster kidney (BHK) cell line can be transfected to express the necessary EPO-R and $β_c$ receptor. The latter approach is advantageous because cell lines can be engineered to express receptor subunits from any species, thereby overcoming potential limitations arising from species specificity. In the alternative, species orthologs of the human receptor cDNA can be cloned and used within cell lines from the same species, such as a mouse cDNA in the BaF3 cell line. Cell lines that are dependent upon one hematopoietic growth factor, such as GM-CSF, can thus be engineered to become dependent upon a tissue protective receptor complex ligand.

Similarly, it will be appreciated by one of ordinary skill in the art that the above assay can be performed in other cell lines that may be transformed in a similar manner. Furthermore, cell proliferation assays may be performed in cells known to harbor both EPO and $β_c$ Receptor. Such cells would preferably include neuronal cell lines including, but not limited to, P-19, PC-12, and astrocytes or other cell lines known to be EPO-responsive including, but not limited to, retinal and heart cells. The presence of both EPO and $β_c$ Receptors in these cell lines can be confirmed using immunoprecipitation methods well known to those of ordinary skill in the art.

Other host cells that can be used to recombinantly produce tissue protective cytokine receptor complex or used in the screening methods of the present invention include, but are not limited to, hybridomas, pre-B cells, 293 cells, 293T cells, HeLa cells, HepG2 cells, K562 cells, 3T3 cells. In a preferred embodiment, the host cells are immortalized cell lines derived from a source, e.g., a tissue. Still other host cells that can be used in the present invention include, but are not limited to, yeast cells, virally-infected cells, bacteria cells, insect cells, or plant cells.

Preferred mammalian host cells include but are not limited to those derived from humans, monkeys and rodents (see, for example, Kriegler M. in "Gene Transfer and Expression: A Laboratory Manual", New York, Freeman & Co. 1990), such as monkey kidney cell line transformed by SV40 (COS-7, ATCC Accession No. CRL 1651); human embryonic kidney cell lines (293, 293-EBNA, or 293 cells subcloned for growth in suspension culture, Graham et al., 1977, J. Gen. Virol., 36:59; baby hamster kidney cells (BHK, ATCC Accession No. CCL 10; chinese hamster ovary-cells-DHFR (CHO, Urlaub and Chasin, 1980, Proc. Natl. Acad. Sci. 77; 4216); mouse sertoli cells (Mather, 1980, Biol. Reprod. 23:243-251); mouse fibroblast cells (NIH-3T3), monkey kidney cells (CVI ATCC Accession No. CCL 70); african green monkey kidney cells (VERO-76, ATCC Accession No. CRL-1587); human cervical carcinoma cells (HELA, ATCC Accession No. CCL 2); canine kidney cells (MDCK, ATCC Accession No. CCL 34); buffalo rat liver cells (BRL 3A, ATCC Accession No. CRL 1442); human lung cells (WI38, ATCC Accession No. CCL 75); human liver cells (Hep G2, HB 8065); and mouse mammary tumor cells (MMT 060562, ATCC Accession No. CCL51). Suitable cultured mammalian cells include the COS-1 (ATCC No. CRL 1650), BHK (ATCC No. CRL 1632), and BHK 570 (ATCC No. CRL 10314), 293 (ATCC No. CRL 1573; Graham et al., J. Gen. Virol. 36:59-72, 1977) cell lines. Additional suitable cell lines are known in the art and available from public depositories such as the American Type Culture Collection, Manassas, Va.

Other useful eukaryotic host-vector system may include yeast and insect systems. In yeast, a number of vectors containing constitutive or inducible promoters may be used with *Saccharomyces cerevisiae* (baker's yeast), *Schizosaccharomyces pombe* (fission yeast), *Pichia pastoris*, and *Hansenula polymorpha* (methylotropic yeasts). For a review see, Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 1987, Acad. Press, N.Y., Vol. 153, pp. 516-544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast *Saccharomyces*, 1982, Eds. Strathern et al., Cold Spring Harbor Press, Vols. I and II.

Fungal cells, including yeast cells, and particularly cells of the genus *Saccharomyces*, can also be used within the present invention, such as for producing receptor polypeptides, receptor fragments, polypeptide fusions, or complexes and for cell-based assays for identifying compounds which modulate tissue protective cytokine activity. Methods for transforming yeast cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in yeast is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha*, *Schizosaccharomyces pombe*, *Kluyveromyces lactis*, *Kluyveromyces fragilis*, *Ustilago maydis*, *Pichia pastoris*, *Pichia methanolica*, *Pichia guillermondii* and *Candida maltosa* are also available for use in the present invention (See, for example, Gleeson et al., 1986, J. Gen. Microbiol. 132:3459-3465, and Cregg, U.S. Pat. No. 4,882,279). *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533.

Standard methods of introducing a nucleic acid sequence of interest into host cells can be used. Transformation may be by any known method for introducing polynucleotides into a host cell, including, for example packaging the polynucleotide in a virus and transducing a host cell with the virus, and by direct uptake of the polynucleotide. The transformation procedure used depends upon the host to be transformed. Mammalian transformations (i.e., transfections) by direct uptake may be conducted using the calcium phosphate precipitation method of Graham & Van der Eb, 1978, Virol. 52:546, or the various known modifications thereof. Other methods for introducing recombinant polynucleotides into cells, particularly into mammalian cells, include dextran-mediated transfection, calcium phosphate mediated transfection, polybrene mediated transfection, protoplast fusion, electroporation, encapsulation of the polynucleotide(s) in liposomes, and direct microinjection of the polynucleotides into nuclei. Such methods are well-known to one of skill in the art.

Suitable host cells are those cell types that can be transformed or transfected with exogenous DNA grown in culture, and include fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., Molecular Cloning: A Laboratory Manual, 2 ed., Cold Spring Harbor Laboratory Press, Cold Spring Harbor, N.Y., 1989, and Ausubel et al., eds., Current Protocols in Molecular Biology, John Wiley and Sons, Inc., NY, 1987.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required.

Cultured mammalian cells are preferred hosts within the present invention. Methods for introducing exogenous DNA into mammalian host cells include calcium phosphate-mediated transfection (Wigler et al., 1978, Cell 14:725; Corsaro and Pearson, 1981, Somatic Cell Genetics 7:603: Graham and Van der Eb, 1973, Virology 52:456), electroporation (Neumann et al., 1982, EMBO J. 1:841-845,), DEAE-dextran mediated transfection (Ausubel et al., eds., Current Protocols in Molecular Biology, John Wiley and Sons, Inc., NY, 1987), and liposome-mediated transfection (Hawley-Nelson et al., 1993, Focus 15:73; Ciccarone et al., 1993, Focus 15:80). The production of recombinant polypeptides, including polypeptides which are components of the receptor complex of the invention, in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. In general, strong transcription promoters are preferred, such as promoters from SV-40 or cytomegalovirus. (See, e.g., U.S. Pat. No. 4,956,288). Other suitable promoters include those from metallothionein genes (U.S. Pat. Nos. 4,579,821 and 4,601,978) and the adenovirus major late promoter. The growth medium will generally select for cells containing the exogenously added DNA by, for example, drug selection or deficiency in an essential nutrient which is complemented by the selectable marker carried on the expression vector or co-transfected into the host cell.

In a preferred embodiment, stable cell lines containing the constructs of interest are generated for high throughput screening. Such stable cells lines may be generated by introducing a construct comprising a selectable marker, allowing the cells to grow for 1-2 days in an enriched medium, and then growing the cells on a selective medium. The selectable marker in the recombinant plasmid confers resistance to the selection and allows cells to stably integrate the plasmid into their chromosomes and grow to form foci which in turn can be cloned and expanded into cell lines.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A number of selection systems may be used, including but not limited to the herpes simplex virus thymidine kinase (Wigler et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy et al., 1980, Cell 22:817) genes can be employed in tk-, hgprt- or aprt- cells, respectively. Also, anti-metabolite resistance can be used as the basis of selection for dhfr, which confers resistance to methotrexate (Wigler et al., 1980, Natl. Acad. Sci. USA 77:3567; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30:147) genes. A preferred selectable marker is a gene encoding resistance to the antibiotic neomycin. Selection may be carried out in the presence of a neomycin-type drug, such as G-418 or the like. Selection systems may also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g., multi-drug resistance, puromycin acetyltransferase) can also be used.

In certain embodiments, Baf3, an interleukin-3 dependent pre-B cell line, which possesses the $\beta_c$ Receptor can be transfected with recombinant EPO-R. The presence of the EPO-R can then be selected by resistance to compounds such as zeocin (at 2 mg/ml) and puromycin (at 2 μg/ml).

5.2.2.2 BaFc Cell Assays

BaF3 cell assays may also be used to identify compounds that modulate the activity of a tissue protective cytokine receptor complex.

For example, an assay to test for proliferation of BaF3 cells via signaling through the receptor complex can be performed as follows. In a 96 well plate eight 1:2 serial dilutions of growth medium alone (RPMI 1640, 10% fetal bovine serum, 1 mM sodium pyruvate, 2 mM L-glutamine), and the small molecule, biologic or chemical compounds of interest. The final volume of each dilution should be about 100 μl.

The BaF3 parental cell line and BaF3 cells transfected with EPO-R can then be washed three times in growth media (see above), pellets resuspended in growth medium, and cells counted and diluted in growth media to 5,000 cells/100 μl. One hundred microliters of diluted cells can then be added to each dilution of samples. The assay plate can then be incubated in a 37° C. incubator for three to four days. A 20 μl aliquot of Alomar blue can be added to each well and the plate is incubated overnight at 37° C. The plates are read on the fluorescent plate reader at excitation wavelength of 544 and emission wavelength 590.

If the compound exhibits a tissue protective activity, the BaF3 cells should proliferate when exposed to the small molecule, biologic or chemical compound of interest.

A natural ligand for the tissue protective receptor complex can also be identified by mutagenizing a cell line expressing the receptor complex and culturing it under conditions that select for autocrine growth. (See WIPO publication WO 95/21930). Within a typical procedure, BaF3 cells expressing tissue protective receptor complex and the necessary additional subunits are mutagenized, such as with 2-ethyl-methanesulfonate (EMS). The cells are then allowed to recover in the presence of IL-3, then transferred to a culture medium lacking IL-3 and IL-4. Surviving cells are screened for the production of a tissue protective receptor complex ligand, such as by adding soluble receptor to the culture medium or by assaying conditioned media on wild-type BaF3 cells and BaF3 cells expressing the receptor.

5.2.2.3 Reporter Gene Assays

In certain embodiments of the invention, cells that are further engineered to express a reporter gene are used in assays to identify compounds with tissue protective activities. The reporter gene is linked to a promoter element that is responsive to the receptor-linked pathway, and the assay detects activation of transcription of the reporter gene.

For example, a reporter gene assay consistent with the methods of the invention may involve testing a compound for modulation of the activity of a tissue protective cytokine receptor complex, wherein the activated complex results in production of a transcription factor in the host cell. The host cell also comprises a SRE promoter element operably linked to a luciferase reporter gene the expression of which is regulated by the transcriptional activator, such that the luciferase gene product is either turned on or off (i.e. present or absent, or present in differing amounts) in the cell in response to the presence of a compound that activates the tissue protective cytokine receptor complex.

Any reporter gene well-known to one of skill in the art may be used in reporter gene constructs to ascertain the effect of a compound on tissue protective cytokine mediated processes or upregulation of protective globulins. A preferred promoter element in this regard is a serum response element, or SRE (see, e.g., Shaw et al., 1989, Cell 56:563-572,). A preferred form of such reporter gene is a luciferase gene (e.g., firefly luciferase, renilla luciferase, and click beetle luciferase) (de Wet et al., 1987, Mol. Cell. Biol. 7:725,). Expression of the luciferase gene is detected by luminescence using methods known in the art (e.g., Baumgartner et al., 1994, J. Biol. Chem. 269:29094-29101; Schenborn and Goiffin, 1993, Promega Notes 41:11). Luciferase activity assay kits are commercially available from, for example, Promega Corp., Madison, Wis. Target cell lines of this type can be used to screen libraries of chemicals, cell-conditioned culture media, fungal broths, soil samples, water samples, and the like. For example, a bank of cell-conditioned media samples can be assayed on a target cell to identify cells that produce ligand. Positive cells are then used to produce a cDNA library in a mammalian expression vector, which is divided into pools, transfected into host cells, and expressed. Media samples from the transfected cells are then assayed, with subsequent division of pools, re-transfection, subculturing, and re-assay of positive cells to isolate a cloned cDNA encoding the ligand.

Examples of reporter genes include, but are not limited to, green fluorescent protein ("GFP") (e.g., green fluorescent protein, yellow fluorescent protein, red fluorescent protein, cyan fluorescent protein, and blue fluorescent protein), beta-galactosidase ("beta-gal"), beta-glucoronidase, beta-lactamase, chloramphenicol acetyltransferase ("CAT"), secreted alkaline phosphatase ("SEAP"), horseradish peroxidase ("HRP") and alkaline phosphatase ("AP"). Alternatively, a reporter gene can also be a protein tag, such as, but not limited to, myc, His, FLAG, or GST, so that nonsense suppression will produce the peptide and the protein can be monitored by an ELISA, a western blot, or any other immunoassay to detect the protein tag. Such methods are well known to one of skill in the art.

The screening methods of the invention also encompass use of other reporter genes. Reporter genes may be obtained and the nucleotide sequence of the elements determined by any method well-known to one of skill in the art. The nucleotide sequence of a reporter gene can be obtained, e.g., from the literature or a database such as GenBank. Alternatively, a polynucleotide encoding a reporter gene may be generated from nucleic acid from a suitable source. If a clone containing a nucleic acid encoding a particular reporter gene is not available, but the sequence of the reporter gene is known, a nucleic acid encoding the reporter gene may be chemically synthesized or obtained from a suitable source (e.g., a cDNA library, or a cDNA library generated from, or nucleic acid, preferably poly A+ RNA, isolated from, any tissue or cells expressing the reporter gene) by PCR amplification. Once the nucleotide sequence of a reporter gene is determined, the nucleotide sequence of the reporter gene may be manipulated using methods well-known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate reporter genes having a different amino acid sequence, for example to create amino acid substitutions, deletions, and/or insertions.

In certain embodiments, the reporter gene assays described above may be carried out in the absence of a tissue protective cytokine receptor complex ligand. In such embodiments, the test compound identified is one that interacts with the tissue protective cytokine receptor complex. In certain other embodiments, the reporter gene assays described above may be carried out in the presence of a tissue protective cytokine receptor complex ligand, such as EPO. In such embodiments, difference in the level of transcription of the reporter gene in the presence and absence of the test compound may be detected. The level of transcript can then be compared to that in the absence of EPO. If the difference in the level of transcript detected with and without the compound is dependent on the presence of EPO, then a compound that modulates the interaction of a tissue protective cytokine receptor complex and EPO is identified. For example, if the difference in level of transcript detected increases in the presence of a compound, wherein the increase is dependent on the presence of EPO, then an agonist of the interaction between EPO and a tissue protective cytokine receptor complex is identified.

5.2.2.4 Yeast Two-Hybrid Assays

The "two-hybrid" system can be used to detect protein-protein interactions in the yeast *Saccharomyces cerevisiae* (Fields and Song, 1989, Nature 340:245-246; U.S. Pat. No. 5,283,173 by Fields and Song). Because the interactions are screened for in yeast, the inter-molecular protein interactions detected in this system occur under physiological conditions that mimic the conditions in mammalian cells (Chien et al., 1991, Proc. Natl. Acad. Sci. U.S.A. 88:9578-9581). This assay utilizes the reconstitution of a transcriptional activator like GAL4 (Johnston, 1987, Microbiol. Rev. 51:458-476) through the interaction of two protein domains that have been fused to the two functional units of a transcriptional activator, the DNA-binding domain and the activation domain. This is possible due to the bipartite nature of certain transcription factors like GAL4. Being characterized as bipartite signifies that the DNA-binding and activation functions reside in separate domains and can function in trans (Keegan et al., 1986, Science 231:699-704). The reconstitution of the transcriptional activator is monitored by the activation of a reporter gene such as the lacZ gene that is under the control of a promoter that contains a binding site (Upstream Activating Sequence or UAS) for the DNA-binding domain of the transcriptional activator. This method is most commonly used either to detect an interaction between two known proteins (Fields and Song, 1989, Nature 340:245-246) or to identify interacting proteins from a population that would bind to a known protein (Durfee et al., 1993, Genes Dev. 7:555-569; Gyuris et al., 1993, Cell 75:791-803; Harper et al., 1993, Cell 75:805-816; Vojtek et al., 1993, Cell 74:205-214). Variations on the methods described herein for yeast two-hybrid assays and other methods for yeast two-hybrid assays are well known to those of skill in the art and can be used in the screening methods of the invention.

Identification of interacting proteins by the improved yeast two hybrid system is based upon the detection of expression of a reporter gene, the transcription of which is dependent upon the reconstitution of a transcriptional regulator by the interaction of two proteins, each fused to one half of the transcriptional regulator. The "bait" (i.e., the tissue protective cytokine receptor complex of the present invention or derivatives or analogs thereof) and "prey" (proteins to be tested for ability to interact with the bait) proteins are expressed as fusion proteins to a DNA binding domain, and to a transcriptional regulatory domain, respectively, or vice versa.

In a specific embodiment, recombinant biological libraries expressing random peptides can be used as the source of prey nucleic acids.

In general, proteins of the bait and prey populations are provided as fusion (chimeric) proteins (preferably by recombinant expression of a chimeric coding sequence) comprising each protein contiguous to a pre-selected sequence. For one population, the pre-selected sequence is a DNA binding domain. The DNA binding domain can be any DNA binding domain, as long as it specifically recognizes a DNA sequence within a promoter. For example, the DNA binding domain is of a transcriptional activator or inhibitor. For the other population, the pre-selected sequence is an activator or inhibitor domain of a transcriptional activator or inhibitor, respectively. The regulatory domain alone (not as a fusion to a protein sequence) and the DNA-binding domain alone (not as a fusion to a protein sequence) preferably do not detectably interact (so as to avoid false positives in the assay). The assay system further includes a reporter gene operably linked to a promoter that contains a binding site for the DNA binding domain of the transcriptional activator (or inhibitor). Accordingly, in the present method of the present invention, binding of a tissue protective cytokine receptor complex fusion protein to a prey fusion protein leads to reconstitution of a transcriptional activator (or inhibitor) which activates (or inhibits) expression of the reporter gene. The activation (or inhibition) of transcription of the reporter gene occurs intracellularly, e.g., in prokaryotic or eukaryotic cells, preferably in cell culture.

The promoter that is operably linked to the reporter gene nucleotide sequence can be a native or non-native promoter of the nucleotide sequence, and the DNA binding site(s) that are recognized by the DNA binding domain portion of the fusion protein can be native to the promoter (if the promoter normally contains such binding site(s)) or non-native to the promoter. Alternatively, the transcriptional activation binding site of the desired gene(s) can be deleted and replaced with GAL4 binding sites (Bartel et al., 1993, BioTechniques 14:920-924, Chasman et al., 1989, Mol. Cell. Biol. 9:4746-4749).

The activation domain and DNA binding domain used in the assay can be from a wide variety of transcriptional activator proteins, as long as these transcriptional activators have separable binding and transcriptional activation domains. For example, the GAL4 protein of *S. cerevisiae* (Ma et al., 1987, Cell 48:847-853), the GCN4 protein of *S. cerevisiae* (Hope & Struhl, 1986, Cell 46:885-894), the ARD1 protein of *S. cerevisiae* (Thukral et al., 1989, Mol. Cell. Biol. 9:2360-2369), and the human estrogen receptor (Kumar et al., 1987, Cell 51:941-951), have separable DNA binding and activation domains. The DNA binding domain and activation domain that are employed in the fusion proteins need not be from the same transcriptional activator. In a specific embodiment, a GAL4 or LEXA DNA binding domain is employed. In another specific embodiment, a GAL4 or herpes simplex virus VP16 (Triezenberg et al., 1988, Genes Dev. 2:730-742) activation domain is employed. In a specific embodiment, amino acids 1-147 of GAL4 (Ma et al., 1987, Cell 48:847-853; Ptashne et al., 1990, Nature 346:329-331) is the DNA binding domain, and amino acids 411-455 of VP16 (Triezenberg et al., 1988, Genes Dev. 2:730-742; Cress et al., 1991, Science 251:87-90) comprise the activation domain.

In a specific embodiment, plasmids encoding the different fusion protein populations can be introduced simultaneously into a single host cell (e.g., a haploid yeast cell) containing one or more reporter genes, by co-transformation, to conduct the assay for protein-protein interactions. Or, preferably, the two fusion protein populations are introduced into a single cell either by mating (e.g., for yeast cells) or cell fusions (e.g., of mammalian cells). In a mating type assay, conjugation of haploid yeast cells of opposite mating type that have been transformed with a binding domain fusion expression construct (preferably a plasmid) and an activation (or inhibitor) domain fusion expression construct (preferably a plasmid), respectively, will deliver both constructs into the same diploid cell. The mating type of a yeast strain may be manipulated by transformation with the HO gene (Herskowitz and Jensen, 1991, Meth. Enzymol. 194:132-146).

In a preferred embodiment, a yeast interaction mating assay is employed using two different types of host cells, strain-type a and alpha of the yeast *Saccharomyces cerevisiae*. The host cell preferably contains at least two reporter genes, each with one or more binding sites for the DNA-binding domain (e.g., of a transcriptional activator). The activator domain and DNA binding domain are each parts of chimeric proteins formed from the two respective populations of proteins. One strain of host cells, for example the a strain, contains fusions of the library of nucleotide sequences with the DNA-binding domain of a transcriptional activator, such as GAL4. The hybrid proteins expressed in this set of host cells are capable of recognizing the DNA-binding site in the promoter or enhancer region in the reporter gene construct. The second set of yeast host cells, for example, the alpha strain, contains nucleotide sequences encoding fusions of a library of DNA sequences fused to the activation domain of a transcriptional activator.

In a specific embodiment, the present invention provides a method of detecting one or more protein-protein interactions comprising (a) recombinantly expressing in a first population of yeast cells being of a first mating type a first fusion protein containing the sequence of a tissue protective cytokine receptor complex or a fragment thereof and a DNA binding domain, wherein said first population of yeast cells contains a first nucleotide sequence operably linked to a promoter driven by one or more DNA binding sites recognized by said DNA binding domain such that an interaction of said first fusion protein with a second fusion protein, said second fusion protein comprising a transcriptional activation domain, results in increased transcription of said first nucleotide sequence; (b) negatively selecting to eliminate those yeast cells in said first population in which said increased transcription of said first nucleotide sequence occurs in the absence of said second fusion protein; (c) recombinantly expressing in a second population of yeast cells of a second mating type different from said first mating type, a plurality of said second fusion proteins, each second fusion protein comprising a sequence of a fragment, derivative or analog of a protein and an activation domain of a transcriptional activator, in which the activation domain is the same in each said second fusion protein; (d) mating said first population of yeast cells with said second population of yeast cells to form a third population of diploid yeast cells, wherein said third population of diploid yeast cells contains a second nucleotide sequence operably linked to a promoter driven by a DNA binding site recognized by said DNA binding domain such that an interaction of said first fusion protein with said second fusion protein results in increased transcription of said second nucleotide sequence, in which the first and second nucleotide sequences can be the same or different; and (e) detecting said increased transcription of said first and/or second nucleotide sequence, thereby detecting an interaction between said first fusion protein and said second fusion protein.

The receptor complexes can be used in interaction trap assays (such as, for example, that described in Gyuris et al., 1993, Cell 75:791-803) to identify proteins which bind to a known protein to identify inhibitors of a binding interaction. This system is a modified two-hybrid system, as described above which uses a LEU2 reporter gene as the first nucleotide sequence and a lacZ reporter gene as the second nucleotide sequence, so that protein-protein interactions that result in the reconstitution of the transcriptional activator system can be selected for in cells lacking leucine and to expression of β-galactosidase. The DNA-binding domain may be the LexA DNA-binding domain, while the activator sequence may be obtained from the B42 transcriptional activation domain (Ma and Ptashne, 1987, Cell 51:113-119). The promoters of the reporter genes contain LexA binding sequences and are activated by the reconstitution of a functional transcriptional activator. Another feature of this system is that the gene encoding the DNA-binding domain fusion protein is under the influence of an inducible promoter, such as a GAL promoter, so that confirmatory tests can be performed under inducing and non-inducing conditions.

In a specific embodiment, the present invention provides a method of detecting a compound that modulates the interaction of EPO and a tissue protective cytokine receptor complex. A first population of yeast cells comprising the first fusion protein contain the sequence of a first tissue protective cytokine receptor such as an EPO receptor, and LexA DNA-binding domain. A second population of yeast cells comprise the second fusion protein comprising a B42 transcriptional activation domain fused to the sequence of a second tissue protective cytokine receptor, such as β common. The LEU2 reporter gene and a lacZ reporter gene are operably linked to promoters contain LexA binding sequences, such that an interaction of said first fusion protein with a second fusion protein, results in increased transcription of said reporter genes. The populations of cell comprising the fusion proteins are grown in media lacking leucine, to select. The media contains EPO and the assay is performed in the presence and absence of a test compound. Where the level of transcription differs in the presence of a test compound, then a compound that modulates the interaction of an EPO and a tissue protective cytokine receptor complex is identified.

Still other versions of the two-hybrid approach exist, for example, a "Contingent Replication Assay" has been reported (Nallur et al., 1993, Nucleic Acids Res. 21:3867-3873; Vasavada et al., 1991, Proc. Natl. Acad. Sci. USA 88:10686-10690). In this case, the reconstitution of the transcription factor in mammalian cells due to the interaction of the two fusion proteins leads to the activation of transcription of the SV40 T antigen. This antigen allows the replication of the activation domain fusion plasmids. Another modification of the two-hybrid approach using mammalian cells is the "Karyoplasmic Interaction Selection Strategy" that also uses the reconstitution of a transcriptional activator (Fearon et al., 1992, Proc. Natl. Acad. Sci. USA 89:7958-7962). Reporter genes used in this case have included the gene encoding the bacterial chloramphenicol acetyl transferase, the gene for cell-surface antigen CD4, and the gene encoding resistance to Hygromycin B. In both of the mammalian systems, the transcription factor that is reconstituted is a hybrid transcriptional activator in which the DNA-binding domain is from GAL4 and the activation domain is from VP16. A transcriptional activation system has been described to isolate and catalog possible protein-protein interactions within a population, and allow the comparison of such interactions between two populations (see PCT Publication WO 97/47763 published Dec. 18, 1997).

5.2.3 High Throughput Screening Assays

The cell-based and non-cell based assays described herein can be utilized in a high throughput format to screen libraries of compounds to identify those compounds that modulate a tissue protective cytokine receptor complex activity or modulate the interaction between a tissue protective cytokine receptor complex ligand and a tissue protective cytokine receptor complex. Examples of libraries of compounds that can be used in high throughput screening assays are disclosed in section 5.4 below.

High throughput screening using labeled probes can be used to identify compounds that affect the formation of specific functional sites. Functional site profiles may be compared between cells treated with a drug and untreated or control cells to identify drugs and drug candidates. Furthermore, where a specific functional site has been associated with a tissue protective activity, probes specific for such a site may be used to determine the status of the site before and after drug treatment to identify a drug that alters the status of the functional site and would, therefore, be useful in cell, tissue, or organ protective therapy. In certain embodiments, treatment with the drug restores the status of the functional site to that observed in a control sample.

The screening assays of the present invention also encompass high throughput screens and assays to identify modulators tissue protective cytokine receptor complex activity. In accordance with this embodiment, the systems described below may be formulated into kits. To this end, cells expressing tissue protective cytokine receptor complex, or lysates thereof, can be packaged in a variety of containers, e.g., vials, tubes, microtitre well plates, bottles, and the like. Other reagents can be included in separate containers and provided with the kit; e.g., positive control samples, negative control samples, buffers, cell culture media, etc. The assays of the present invention may be first optimized on a small scale (i.e., in test tubes), and then scaled up for high throughput assays.

5.3 Assays for Identifying Compounds or Testing Compounds Identified in Screening Assays 5.3.1 Biological Screens or Assays Compounds identified to have an effect on tissue protective cytokine receptor complex activity or compounds found to modulate the interaction between a tissue protective cytokine complex and a ligand may be tested for tissue protective activity, e.g., protecting cells, tissues or organs. A protective activities may be further tested using in vitro and in vivo assays. In vitro tests that are indicative of tissue protective activity include, for example, cell proliferation assays, cell differentiation assays, or detecting the presence of proteins or nucleic acids upregulated by tissue protective cytokine receptor complex activity, e.g., nucleolin, neuroglobin, and cytoglobin. Neuroglobin, for example, may be involved in facilitating the transport or the short-term storage of oxygen. Therefore, oxygen transport or storage assays may be used as an assay to identify or screen for compounds which modulate tissue protective cytokine activity.

Neuroglobin is expressed in cells and tissues of the central nervous system in response to hypoxia or ischemia and may provide protection from injury (Sun et al. 2001, PNAS 98:15306-15311; Schmid et al., 2003, J. Biol. Chem. 276: 1932-1935). Cytoglobin may play a similar role in protection, but is expressed in a variety of tissues at varying levels (Pesce et al., 2002, EMBO 3:1146-1151). In one embodiment of the invention, the levels of an upregulated protein in a cell may be measured before and after contacting the identified test compound to a cell. In certain embodiments, the presence of a upregulated protein associated with tissue protective activity in a cell, may be used to confirm the tissue protective activities of a compound.

Nucleolin may protect cells from damage. It plays numerous roles in cells including modulation of transcription processes, sequence specific RNA-binding protein, cytokinesis, nucleogensis, signal transduction, apoptosis induced by T-cells, chromatin remodelling, or replication. It can also function as a cell surface receptor DNA/RNA helicase, DNA-dependent ATPase, protein shuttle, transcription factor component, or transcriptional repressor (Srivastava and Pollard, 1999, FASEB J., 13:1911-1922; and Ginisty et al., 1999, J. Cell Sci., 112:761-772).

Expression of an upregulated protein may be detected by detecting mRNA levels corresponding to the protein in a cell. The mRNA can be hybridize to a probe that specifically binds a nucleic acid encoding the upregulated protein. Hybridization may consist of, for example, Northern blot, Southern blot, array hybridization, affinity chromatography, or in situ hybridization.

Animal model systems can be used to demonstrate the tissue protective activity of a compound or to demonstrate the safety and efficacy of the compounds identified by the screening methods of the invention described above. The compounds identified in the assays can then be tested for biological activity using animal models for a type of tissue damage, disease, condition, or syndrome of interest. These include animals engineered to contain the tissue protective cytokine receptor complex coupled to a functional readout system, such as a transgenic mouse.

Animal models that can be used to test the efficacy of the cell or tissue protective activity of an identified compound include, for example, protection against the onset of Acute Experimental Allergic Encephalomyelitis (EAE) in Lewis rats, restoration or protection from diminished cognitive function in mice after receiving brain trauma (Brines et al., 2000, PNAS, 97:10295-10672), and protection from induced retinal ischemia (Rosenbaum et al., 1997, *Vis. Res.* 37:3443-51). Such assays are described in further detail in PCT publication no. WO02/053580, which is incorporated by reference herein in its entirety. The in vivo described therein are directed towards administration of EPO, however, a test compound that has been identified to have an effect on the activity of a tissue protective cytokine receptor complex could be administered in place of EPO to test for tissue protective activity. Other assays for determining tissue protective activity of a compound are well known to those of skill in the art.

The assays designed to determine the tissue protective activity of a compound identified can be performed in the presence or absence of a tissue protective cytokine receptor complex ligand depending on whether the compound identified is one that interacts with the tissue protective cytokine receptor complex or modulates the interaction of a tissue protective cytokine receptor complex ligand and a tissue protective cytokine receptor complex.

In certain embodiments additional tissue protective cytokine receptor complex ligand is added to the assay to further confirm the modulation activity of a compound on the interaction of a tissue protective cytokine receptor complex ligand and a tissue protective cytokine receptor complex.

5.3.2 Cell Binding Assays

Alternatively, cell binding assays utilizing the cells disclosed above in section 5.2.2.1 can be utilized as well. For example, BaF3 cells could be transfected with EPO and $\beta_c$ receptor as discussed above. Additionally, the small molecule, biologic or chemical compound of interest should be bound to a biological marker such as a fluorescent or radiolabled marker.

In a 96 well plate eight 1:2 serial dilutions of growth medium alone (RPMI 1640, 10% fetal bovine serum, 1 mM sodium pyruvate, 2 mM L-glutamine), and the small molecule, biologic or chemical compounds of interest. The final volume of each dilution should be about 100 µl.

The BaF3 parental cell line and BaF3 cells transfected with EPO-R can then be washed three times in growth media (see above), pellets resuspended in growth medium, and cells counted and diluted in growth media to 5,000 cells/100 µl. One hundred microliters of diluted cells can then be added to each dilution of samples. The assay plate can then be incubated in a 37° C. incubator for three to four days. The cells are then washed and the plate can then be read on a fluorescent plate reader or by other suitable method to detect the biomarker attached to the compound of interest.

Similarly, a competitive assay can be utilized to determine if a compound is tissue protective. In the competitive assay, a compound known to be tissue protective including, but not limited to, tissue protective cytokines such as those disclosed in U.S. patent application Ser. Nos. 10/188,905 and 10/185,841, can be attached to a suitable bio marker.

In a 96 well plate eight 1:2 serial dilutions of growth medium alone (RPMI 1640, 10% fetal bovine serum, 1 mM sodium pyruvate, 2 mM L-glutamine), and the remaining wells have the tissue protective compound/biomarker, the tissue protective compound/biomarker and an excess of the small molecule, biologic, or chemical compound of interest in them. The final volume of each dilution should be about 100 µl. Once again, the BaF3 cells are seeded into the plates as disclosed above and allowed to incubate. After an appropriate amount of time, the cells are washed and the plate can then be read on a fluorescent plate reader or by other suitable method to detect the biomarker. If the readout of the plates containing tissue protective compound/biomarker and compound of interest is less than the readout of the plates containing only the tissue protective compound/biomarker then the compound of interest is tissue protective.

5.3.3 Cytokine and Cell Proliferation/Differentiation Activity

A receptor complex of the present invention may be helpful in identifying tissue protective compounds (small molecule, protein, chemical agents) in cytokine, cell proliferation (either inducing or inhibiting) or cell differentiation (either inducing or inhibiting) assays. Many protein factors discovered to date, including all known cytokines, have exhibited activity in one or more factor-dependent cell proliferation assays, and hence these assays serve as a convenient confirmation of cytokine activity. The activity of a compound can be evidenced by any one of a number of routine factor dependent cell proliferation assays for cell lines including, without limitation, 32D, DA2, DA1G, T10, B9, B9/11, BaF3, MC9/G, M+(preB M+), 2E8, RB5, DA1, 123, T1165, HT2, CTLL2, TF-1, Mo7e and CMK. These cells are cultured in the presence or absence of a test compound, and cell proliferation is detected by, for example, measuring incorporation of tritiated thymidine or by colorimetric assay based on the metabolic breakdown of 3-(4,5-dimethylthiazol-2-yl)-2,5-diphenyl tetrazolium bromide (MTT) (Mosman, 1983, *J. Immunol. Meth.* 65:55-63). The activity of a tissue protective cytokine receptor complex may, among other means, be measured by binding of a compound or ligand to the tissue protective cytokine receptor complex, cell proliferation, cell differentiation, upregulation of proteins that have a tissue protective effect, or a tissue protective activity.

5.3.4 Fusion Proteins

A receptor extracellular domain can be expressed as a fusion with immunoglobulin heavy chain constant regions, typically an $F_c$ fragment, which contains two constant region domains and a hinge region but lacks the variable region. Such fusions are typically secreted as multimeric molecules wherein the Fc portions are disulfide bonded to each other and two receptor polypeptides are arrayed in closed proximity to each other. In accordance with the present invention, the receptor polypeptides on the fusion should include at least one EPO-R extracellular domain and one $\beta_c$ Receptor extracellular domain. Fusions of this type can be used to purify the cognate ligand from solution, as an in vitro assay tool, to block signals in vitro by specifically titrating out ligand, and as antagonists in vivo by administering them parenterally to bind circulating ligand and clear it from the circulation. To purify ligand, a tissue protective receptor complex chimera is added to a sample containing the ligand (e.g., cell-conditioned culture media or tissue extracts) under conditions that facilitate receptor-ligand binding (typically near-physiological temperature, pH, and ionic strength). The chimera-ligand complex is then separated from the mixture using protein A, which is immobilized on a solid support (e.g., insoluble resin beads). The ligand is then eluted using conventional chemical techniques, such as with a salt or pH gradient. In the alternative, the chimera itself can be bound to a solid support, with binding and elution carried out as above. Chimeras with high binding affinity are administered parenterally (e.g., by intramuscular, subcutaneous or intravenous injection). Circulating molecules bind ligand and are cleared from circulation by normal physiological processes. For use in assays, the chimeras may be bound to a support via the $F_c$ region and used in an ELISA format.

A preferred assay system employing a ligand-binding receptor complex fusion protein or ligand-binding receptor complex fragment uses a commercially available biosensor instrument (BIAcore™, Pharmacia Biosensor, Piscataway, N.J.), wherein the fusion protein is immobilized onto the surface of a receptor chip. Use of this instrument is disclosed by Karlsson, 1991, J. Immunol. Methods 145:229-240, and Cunningham and Wells, 1993, J. Mol. Biol. 234:554-563. A fusion protein is covalently attached, using amine or sulfhydryl chemistry, to dextran fibers that are attached to gold film within the flow cell. A test sample is passed through the cell. If ligand is present in the sample, it will bind to the immobilized fusion protein, causing a change in the refractive index of the medium, which is detected as a change in surface plasmon resonance of the gold film. This system allows the determination of on- and off-rates, from which binding affinity can be calculated, and assessment of stoichiometry of binding.

Ligand-binding fusion proteins may also be used within other assay systems known in the art. Such systems include Scatchard analysis for determination of binding affinity (see, Scatchard, 1949, Ann. NY Acad. Sci. 51:660-672) and calorimetric assays (Cunningham et al., 1991, Science 253:545-548; Cunningham et al., 1991, Science 254:821-825).

A receptor ligand-binding fusion protein can also be used for purification of ligand. The fusion protein is immobilized on a solid support, such as beads of agarose, cross-linked agarose, glass, cellulosic resins, silica-based resins, polystyrene, cross-linked polyacrylamide, or like materials that are stable under the conditions of use. Methods for linking polypeptides to solid supports are known in the art, and include amine chemistry, cyanogen bromide activation, N-hydroxysuccinimide activation, epoxide activation, sulfhydryl activation, and hydrazide activation. The resulting media will generally be configured in the form of a column, and fluids containing ligand are passed through the column one or more times to allow ligand to bind to the receptor polypeptide. The ligand is then eluted using changes in salt concentration or pH to disrupt ligand-receptor binding.

5.3.5 Other Assays

One of ordinary skill in the art will recognize that the receptor complex of the present invention has utility in several well known assays including but not limited to the Ligand-Receptor Assays disclosed in Current Protocols In Immunology, vol. 4, vol. 4, Chapter 18, 2001, John E. Coligan Ed. John Wiley and Sons.

If the compound exhibits a tissue protective activity, one of ordinary skill in the art would recognize that it would be beneficial to verify the result using one of the neuroprotective and tissue protective assays known to those skilled in the art, such as, but not limited to, P-19, PC-12, TF-1, and UT-7 cell assays. Additionally, various in vivo models such as animal models related to spinal cord injury, ischemic stroke, peripheral nerve damage, and the heart and eyes would be helpful in further characterizing the tissue protective compound isolated. Suitable in vitro and in vivo assays are disclosed in U.S. patent application Ser. Nos. 10/188,905 and 10/185,841.

5.3.5.1 Assays Using $\beta_c$ (−/−) Knock-out Animals

The invention also relates to the use of host cells and animals genetically engineered to inhibit or "knock-out" expression of the animal's endogenous $\beta_c$ receptor and/or express the human $\beta_c$ receptor (or mutants thereof). Such transgenic animals may be used in methods for identifying neuroprotective pathways and compounds which activate neuroprotective pathways.

Endogenous target gene expression can also be reduced by inactivating or "knocking out" the target gene or its promoter using targeted homologous recombination (e.g., see Smithies et al., 1985, Nature 317, 230-234; Thomas & Capecchi, 1987, Cell 51, 503-512; Thompson et al., 1989, Cell 5, 313-321; each of which is incorporated by reference herein in its entirety). For example, a mutant, non-functional target gene (or a completely unrelated DNA sequence) flanked by DNA homologous to the endogenous target gene (either the coding regions or regulatory regions of the target gene) can be used, with or without a selectable marker and/or a negative selectable marker, to transfect cells that express the target gene in vivo. Insertion of the DNA construct, via targeted homologous recombination, results in inactivation of the target gene. Such approaches are particularly suited modifications to ES (embryonic stem) cells can be used to generate animal offspring with an inactive target gene (e.g., see Thomas & Capecchi, 1987 and Thompson, 1989, supra). However this approach can be adapted for use in humans provided the recombinant DNA constructs are directly administered or targeted to the required site in vivo using appropriate viral vectors.

Once $\beta_c$ receptor (−/−) knock-out animals have been generated, the expression of the recombinant $\beta_c$ receptor gene may be assayed utilizing standard techniques. Initial screening may be accomplished by Southern blot analysis or PCR techniques to analyze animal tissues to assay whether knock-out of the endogenous gene has taken place. The level of mRNA expression of the transgene in the tissues of the transgenic animals may also be assessed using techniques that include but are not limited to Northern blot analysis of tissue samples obtained from the animal, in situ hybridization analysis, and RT-PCR (reverse transcriptase PCR). Samples of $\beta_c$ receptor gene-expressing tissue, may also be evaluated immunocytochemically using antibodies specific for the $\beta_c$ receptor transgene product.

In one embodiment of the invention, βc receptor (−/−) knock-out animals are used in assays to identify pathways and/or compounds that involved in a tissue protective activity. For example, normal and βc receptor (−/−) knock-out animals may both be administered an agent or force known to cause tissue damage, e.g., ischemia. Both animals may then be administered a compound and the tissue protective activity of the compound can be determined. Methods for determining a tissue protective activity are well known to those in the art and examples of such methods are disclosed in PCT publication no. WO02/053580, which is incorporated by reference herein in its entirety. If a tissue protective activity is observed in the normal animals but not in the βc receptor (−/−) knock-out animals administered the same compound, then a compound with tissue protective activities dependent on the βc receptor is identified. Further investigation into the identified βc receptor dependent tissue protective pathway may consist of determining if the compound binds to the βc receptor or complexes thereof, or identifying proteins or mRNA transcripts present only in the animals exhibiting the tissue protective activity. Applicants hypothesize that secondary or redundant pathways for tissue protection may be present and that βc receptor (−/−) knock-out animals could be used to investigate such pathways.

5.4 Compounds

The methods of the invention for screening and identifying compounds may utilize numerous types of compounds including, but are not limited to, small molecules, organic molecules, non-organic molecules, peptides, polypeptides, peptide analogs including peptides comprising non-naturally occurring amino acids, e.g., D-amino acids, phosphorous analogs of amino acids, such as D-amino phosphoric acids and D-amino phosphoric acids, or amino acids having non-peptide linkages, nucleic acid analogs such as phosphorothioates and PNAs.

Compounds that can be tested and identified methods described herein can include, but are not limited to, compounds obtained from any commercial source, including Aldrich (Milwaukee, Wis. 53233), Sigma Chemical (St. Louis, Mo.), Fluka Chemie AG (Buchs, Switzerland) Fluka Chemical Corp. (Ronkonkoma, N.Y.), Eastman Chemical Company, Fine Chemicals (Kingsport, Tenn.), Boehringer Mannheim GmbH (Mannheim, Germany), Takasago (Rockleigh, N.J.), SST Corporation (Clifton, N.J.), Ferro (Zachary, La. 70791), Riedel-deHaen Aktiengesellschaft (Seelze, Germany), PPG Industries Inc., Fine Chemicals (Pittsburgh, Pa. 15272). Further any kind of natural products may be screened using the methods of the invention, including microbial, fungal, plant or animal extracts.

Libraries of polypeptides or proteins can also be used in the assays of the invention. For example, the test compound may be a small molecule, an organic molecule, a non-organic molecule, or a peptide. Examples of libraries of such compounds that can be screened in accordance with the methods of the invention include, but are not limited to, peptoids; random biooligomers; diversomers such as hydantoins, benzodiazepines and dipeptides; vinylogous polypeptides; non-peptidal peptidomimetics; oligocarbamates; peptidyl phosphonates; peptide nucleic acid libraries; antibody libraries; carbohydrate libraries; and small molecule libraries (small organic or non-organic molecule libraries). Examples of such libraries include, but are not limited to, random peptide libraries; (see, e.g., Lam et al., 1991, Nature 354:82-84; Houghten et al., 1991, Nature 354:84-86), and combinatorial chemistry-derived molecular library made of D- and/or L-configuration amino acids, phosphopeptides (including, but not limited to, members of random or partially degenerate, directed phosphopeptide libraries; see, e.g., Songyang et al., 1993, Cell 72:767-778), antibodies (including, but not limited to, polyclonal, monoclonal, humanized, anti-idiotypic, chimeric or single chain antibodies, and FAb, F(ab')$_2$ and FAb expression library fragments, and epitope-binding fragments thereof), and small organic or inorganic molecules.

In one embodiment of the present invention, peptide libraries may be used as a source of test compounds that can be used to screen for modulators of tissue protective cytokine receptor complex interactions, such as EPO-tissue protective cytokine receptor complex. Diversity libraries, such as random or combinatorial peptide or nonpeptide libraries can be screened for molecules that specifically bind to the tissue protective cytokine receptor complex. Many libraries are known in the art that can be used, e.g., chemically synthesized libraries, recombinant (e.g., phage display libraries), and in vitro translation-based libraries.

Examples of chemically synthesized libraries are described in Fodor et al., 1991, Science 251:767-773; Houghten et al., 1991, Nature 354:84-86; Lam et al., 1991, Nature 354:82-84; Medynski, 1994, Bio/Technology 12:709-710; Gallop et al., 1994, J. Medicinal Chemistry 37(9):1233-1251; Ohlmeyer et al., 1993, Proc. Natl. Acad. Sci. USA 90:10922-10926; Erb et al., 1994, Proc. Natl. Acad. Sci. USA 91:11422-11426; Houghten et al., 1992, Biotechniques 13:412; Jayawickreme et al., 1994, Proc. Natl. Acad. Sci. USA 91:1614-1618; Salmon et al., 1993, Proc. Natl. Acad. Sci. USA 90:11708-11712; PCT Publication No. WO 93/20242; and Brenner and Lerner, 1992, Proc. Natl. Acad. Sci. USA 89:5381-5383.

Examples of phage display libraries are described in Scott & Smith, 1990, Science 249:386-390; Devlin et al., 1990, Science, 249:404-406; Christian et al., 1992, J. Mol. Biol. 227:711-718; Lenstra, 1992, J. Immunol. Meth. 152:149-157; Kay et al., 1993, Gene 128:59-65; and PCT Publication No. WO 94/18318 dated Aug. 18, 1994.

By way of examples of nonpeptide libraries, a benzodiazepine library (see e.g., Bunin et al., 1994, Proc. Natl. Acad. Sci. USA 91:4708-4712) can be adapted for use. Peptoid libraries (Simon et al., 1992, Proc. Natl. Acad. Sci. USA 89:9367-9371) can also be used. Another example of a library that can be used, in which the amide functionalities in peptides have been permethylated to generate a chemically transformed combinatorial library, is described by Ostresh et al. (1994, Proc. Natl. Acad. Sci. USA 91:11138-11142).

Screening the libraries can be accomplished by any of a variety of commonly known methods. See, e.g., the following references, which disclose screening of peptide libraries: Parmley & Smith, 1989, Adv. Exp. Med. Biol. 251:215-218; Scott & Smith, 1990, Science 249:386-390; Fowlkes et al., 1992; BioTechniques 13:422-427; Oldenburg et al., 1992, Proc. Natl. Acad. Sci. USA 89:5393-5397; Yu et al., 1994, Cell 76:933-945; Staudt et al., 1988, Science 241:577-580; Bock et al., 1992, Nature 355:564-566; Tuerk et al., 1992, Proc. Natl. Acad. Sci. USA 89:6988-6992; Ellington et al., 1992, Nature 355:850-852; U.S. Pat. Nos. 5,096,815, 5,223,409, and 5,198,346, all to Ladner et al.; Rebar & Pabo, 1993, Science 263:671-673; and PCT Publication No. WO 94/18318.

In a preferred embodiment, the combinatorial libraries are small organic molecule libraries, such as, but not limited to, benzodiazepines, isoprenoids, thiazolidinones, metathiazanones, pyrrolidines, morpholino compounds, and benzodiazepines. In another embodiment, the combinatorial libraries comprise peptoids; random bio-oligomers; benzodiazepines; diversomers such as hydantoins, benzodiazepines and dipeptides; vinylogous polypeptides; nonpeptidal peptidomimetics; oligocarbamates; peptidyl phosphonates; peptide nucleic acid libraries; antibody libraries; or carbohydrate libraries. Combinatorial libraries are themselves commercially available (see, e.g., ComGenex, Princeton, N.J.; Asinex, Moscow, Ru, Tripos, Inc., St. Louis, Mo.; ChemStar, Ltd, Moscow, Russia; 3D Pharmaceuticals, Exton, Pa.; Martek Biosciences, Columbia, Md.; etc.).

In a preferred embodiment, the library is preselected so that the compounds of the library are more amenable for cellular uptake. For example, compounds are selected based on specific parameters such as, but not limited to, size, lipophilicity, hydrophilicity, and hydrogen bonding, which enhance the likelihood of compounds getting into the cells. In another embodiment, the compounds are analyzed by three-dimensional or four-dimensional computer computation programs.

In one embodiment, the combinatorial compound library for the methods of the present invention may be synthesized. There is a great interest in synthetic methods directed toward the creation of large collections of small organic compounds, or libraries, which could be screened for pharmacological, biological or other activity. The synthetic methods applied to create vast combinatorial libraries are performed in solution or in the solid phase, i.e., on a solid support. Solid-phase synthesis makes it easier to conduct multi-step reactions and to drive reactions to completion with high yields because excess reagents can be easily added and washed away after each reaction step. Solid-phase combinatorial synthesis also tends to improve isolation, purification and screening. However, the more traditional solution phase chemistry supports a wider variety of organic reactions than solid-phase chemistry.

Combinatorial compound libraries of the present invention may be synthesized using the apparatus described in U.S. Pat. No. 6,190,619 to Kilcoin et al., which is hereby incorporated by reference in its entirety. U.S. Pat. No. 6,190,619 discloses a synthesis apparatus capable of holding a plurality of reaction vessels for parallel synthesis of multiple discrete compounds or for combinatorial libraries of compounds.

In one embodiment, the combinatorial compound library can be synthesized in solution. The method disclosed in U.S. Pat. No. 6,194,612 to Boger et al., which is hereby incorporated by reference in its entirety, features compounds useful as templates for solution phase synthesis of combinatorial libraries. The template is designed to permit reaction products to be easily purified from unreacted reactants using liquid/liquid or solid/liquid extractions. The compounds produced by combinatorial synthesis using the template will preferably be small organic molecules. Some compounds in the library may mimic the effects of non-peptides or peptides. In contrast to solid phase synthesize of combinatorial compound libraries, liquid phase synthesis does not require the use of specialized protocols for monitoring the individual steps of a multi-step solid phase synthesis (Egner et al., 1995, J. Org. Chem. 60:2652; Anderson et al., 1995, J. Org. Chem. 60:2650; Fitch et al., 1994, J. Org. Chem. 59:7955; Look et al., 1994, J. Org. Chem. 49:7588; Metzger et al., 1993, Angew. Chem., Int. Ed. Engl. 32:894; Youngquist et al., 1994, Rapid Commun. Mass Spect. 8:77; Chu et al., 1995, J. Am. Chem. Soc. 117:5419; Brummel et al., 1994, Science 264:399; Stevanovic et al., 1993, Bioorg. Med. Chem. Lett. 3:431).

Combinatorial compound libraries useful for the methods of the present invention can be synthesized on solid supports. In one embodiment, a split synthesis method, a protocol of separating and mixing solid supports during the synthesis, is used to synthesize a library of compounds on solid supports (see e.g., Lam et al., 1997, Chem. Rev. 97:41-448; Ohlmeyer et al., 1993, Proc. Natl. Acad. Sci. USA 90:10922-10926 and references cited therein). Each solid support in the final library has substantially one type of compound attached to its surface. Other methods for synthesizing combinatorial libraries on solid supports, wherein one product is attached to each support, will be known to those of skill in the art (see, e.g., Nefzi et al., 1997, Chem. Rev. 97:449-472).

As used herein, the term "solid support" is not limited to a specific type of solid support. Rather a large number of supports are available and are known to one skilled in the art. Solid supports include silica gels, resins, derivatized plastic films, glass beads, cotton, plastic beads, polystyrene beads, alumina gels, and polysaccharides. A suitable solid support may be selected on the basis of desired end use and suitability for various synthetic protocols. For example, for peptide synthesis, a solid support can be a resin such as p-methylbenzhydrylamine (PMBHA) resin (Peptides International, Louisville, Ky.), polystyrenes (e.g., PAM-resin obtained from Bachem Inc., Peninsula Laboratories, etc.), including chloromethylpolystyrene, hydroxymethylpolystyrene and aminomethylpolystyrene, poly (dimethylacrylamide)-grafted styrene co-divinyl-benzene (e.g., POLYHIPE resin, obtained from Aminotech, Canada), polyamide resin (obtained from Peninsula Laboratories), polystyrene resin grafted with polyethylene glycol (e.g., TENTAGEL or ARGOGEL, Bayer, Tubingen, Germany) polydimethylacrylamide resin (obtained from Milligen/Biosearch, California), or Sepharose (Pharmacia, Sweden).

In some embodiments of the present invention, compounds can be attached to solid supports via linkers. Linkers can be integral and part of the solid support, or they may be nonintegral that are either synthesized on the solid support or attached thereto after synthesis. Linkers are useful not only for providing points of compound attachment to the solid support, but also for allowing different groups of molecules to be cleaved from the solid support under different conditions, depending on the nature of the linker. For example, linkers can be, inter alia, electrophilically cleaved, nucleophilically cleaved, photocleavable, enzymatically cleaved, cleaved by metals, cleaved under reductive conditions or cleaved under oxidative conditions. In a preferred embodiment, the compounds are cleaved from the solid support prior to high throughput screening of the compounds.

5.4.1.1 Modified EPO and EPO Mutants

In certain embodiments of the invention, the test compound used in the assay and/or the tissue protective cytokine receptor complex ligand used in assays for identifying compounds that modulate the interaction of a tissue protective cytokine receptor complex and a ligand thereof is a chemically modified EPO, a mutant EPO, or a combination thereof. For example, U.S. patent application Ser. No. 10/188,905, which published as 20030072737-A1 on Apr. 17, 2003, discloses chemically modified EPO and U.S. patent application Ser. No. 10/612,665 which are incorporated by reference herein in their entirety. Such chemically modified and/or mutant molecules may be used in the screening assays of the invention described herein.

Chemically modified EPO molecules that may be used in the screening methods of the invention include, for example, erythropoietins that have been altered by at least one modification as compared to a native erythropoietin, and preferably as compared to native human erythropoietin. The at least one modification may be a modification of at least one amino acid of the erythropoietin molecule, or a modification of at least one carbohydrate of the erythropoietin molecule. Of course, chemically modified EPO useful for the purposes herein may have a plurality of modifications compared to a native molecule, such as multiple modifications of the amino acid portion of the molecule, multiple modifications of the carbohydrate portion of the molecule, or at least one modification of the amino acid portion of the molecule and at least one modification of the carbohydrate portion of the molecule. The chemically modified EPO molecule retains its ability of protecting, maintaining, enhancing or restoring the function or viability of responsive mammalian cells, yet one or more properties of the erythropoietin molecule unrelated to the aforementioned, desirable feature may be absent as compared to the native molecule. In a preferred embodiment, the chemically modified EPO lacks erythropoietin's affects on the bone marrow, i.e., increased hematocrit (erythropoiesis), vasoconstriction (high blood pressure), increased blood pressure, hyperactivation of platelets, pro-coagulant activities, and increased production of thrombocytes. More preferably, the chemically modified EPO lack erythropoiesis; most preferably the chemically modified EPO are devoid of all of erythropoietin's effects on the bone marrow.

By way of example, the chemically modified EPO of the invention may be asialoerythropoietin. In another example, the chemically modified EPO of the invention may be erythropoietin or asialoerythropoietin that has been reacted with one or more reagents that modify one or more amino groups of amino acid residues of native erythropoietin or asialoerythropoietin. In a preferred embodiment, the chemically modified EPO is nonerythropoietic.

In one embodiment, the chemically modified EPO is an erythropoietin that has no sialic acid moieties. In a preferred embodiment, the chemically modified EPO is asialoerythropoietin, and most preferably, human asialoerythropoietin. In another embodiment, the chemically modified EPO has 1, 2, 3, 4, 5, 6, 7, 8, 9, 10, 11, 12, or 13 sialic acid moieties. Such partially desialylated erythropoietins are referred to herein as hyposialoerythropoietins. They may be prepared by chemical or enzymatic modification of native erythropoietin, or may be obtained by expression in a system which either does not sialylate the molecule at all or only partially sialylates the erythropoietin. The asialoerythropoietin and hyposialoerythropoietin of the invention are embraced regardless of the means by which the molecules are prepared.

In another preferred embodiment, the chemically modified EPO comprises at least one or more modified lysine residues or a modification of the N-terminal amino group of the erythropoietin molecule, such modifications as those resulting from reaction of the lysine epsilon amino group or the N-terminal amino group with an amino-group-modifying agent or agents. The modified lysine residue or modified N-terminal amino group further may be chemically reduced. In one preferred embodiment, an erythropoietin is biotinylated, carbamylated, succinylated or acetylated at one or more lysine groups or at the N-terminus. In another preferred embodiment, the lysine is reacted with an aldehyde or reducing sugar to form an imine, which optionally is then stabilized by chemical reduction such as by using sodium cyanoborohydride to form an N-alkylated lysine residue such as glucitolyl lysine, or which in the case of reducing sugars may be stabilized by Amadori or Heyns rearrangement to form an alpha-deoxy alpha-amino sugar such as alpha-deoxy-alpha-fructo-syllysine. In another preferred embodiment, the lysine or N-terminal amino group is carbamylated (carbamoylated), such as by virtue of reaction with cyanate ion, alkyl-carbamylated, aryl-carbamylated, or aryl-thiocarbamylated with an alkyl-isocyanate, aryl-isocyanate, or aryl-isothiocyanate, respectively, or it may be acylated by a reactive alkylcarboxylic or arylcarboxylic acid derivative, such as by reaction with acetic anhydride, succinic anhydride or phthalic anhydride. At least one lysine group or the N-terminal amino group may also be trinitrophenyl modified by reaction with a trinitrobenzenesulfonic acid, or preferably with one of its salts. In another embodiment, lysine residues may be modified by reaction with a glyoxal, such as reaction with glyoxal, methylglyoxal or 3-deoxyglucosone to form the corresponding alpha-carboxyalkyl derivatives.

In another embodiment, a chemically modified EPO can be generated by modifying at least one tyrosine residue of erythropoietin by using an electrophilic reagent, such as but not limited to modification by nitration or iodination, to modify an aromatic ring position.

As noted above, a tissue protective agent useful for the purposes herein may have at least one of the aforementioned modifications, but may have more than one of the above modifications. By way of example of chemically modified EPOs with one modification to the amino acid portion of the molecule and optional modification to the carbohydrate portion of the molecule, a chemically modified EPO is carbamylerythropoietin, carbamylasialoerythropoietin, carbamylhyposialoerythropoietin, acetylerythropoietin, acetylasialoerythropoietin, acetylhypoasialoerythropoietin, succinylerythropoietin, succinylasialoerythropoietin, succinylhyposialoerythropoietin, biotinylerythropoietin, biotinylasialoerythropoietin, biotinylhypsialoerythropoietin, iodoerythropoietin, iodoasialoerythropoietin, iodohyposialoerythropoietin, N-epsilon-carboxymethylerythropoietin, N-epsilon-carboxymethylerythropoietin, N-epsilon-carboxymethylhyposialoerythropoietin, and glucitolylerythropoietin, glucitolylasialoerythropoietin, glucitolylasialohypoerythropoietin. These compounds are merely exemplary of the modified erythropoietins of the invention. The foregoing trivial names are merely representative of the modifications of the native erythropoietin molecule, and as hereinbefore described, the modification of the amino group may be on one or more epsilon amino groups of lysine residues, or the N-terminal amino group, or, in the instance of nitro- or iodo-modified erythropoietins, of one or more tyrosine residues. Any combination of the foregoing is embraced herein. The present invention also embraces chemically modified EPO, comprising one or more of the aforementioned chemical modifications.

In another aspect of the invention, a method is provided for the protecting, maintaining, enhancing or restoring the function or viability of responsive mammalian cells and their associated cells, tissues and organs, by administering an effective amount of any one or more of the aforementioned chemically modified EPOs. In one particular aspect of the method, the responsive mammalian cells and their associated cells, tissues or organs are distal to the vasculature by virtue of a tight endothelial cell barrier. In another particular aspect, the cells, tissues, organs or other bodily parts are isolated from a mammalian body, such as those intended for transplant or reattachment. By way of non-limiting examples, the responsive cell or tissue may be neuronal, retinal, muscle, heart, lung, liver, kidney, small intestine, adrenal cortex, adrenal medulla, capillary endothelial, testes, ovary, pancreas, skin, bones, or endometrial cells or tissue. These examples of responsive cells are merely illustrative. In a particular embodiment, the responsive cell or its associated cells, tissues, or organs are not excitable cells, tissues, or organs, or do not predominantly comprise excitable cells or tissues. In another particular embodiment, the mammalian cell, tissue or organ for which an aforementioned chemically modified EPO may be administered are those that have expended or will expend a period of time under at least one condition adverse to the viability of the cell, tissue or organ. Such conditions may include traumatic in-situ hypoxia or metabolic dysfunction, surgically-induced in-situ hypoxia or metabolic dysfunction, or in-situ toxin exposure; the latter may be associated with chemotherapy or radiation therapy. In one embodiment, the invention protects against the adverse conditions resulting from cardio-pulmonary bypass.

The invention also provides for a screening method that uses a chemically modified EPO that is i) an erythropoietin that lacks sialic acid moieties; ii) an erythropoietin that lacks N-linked or lacks O-linked carbohydrates; iii) an erythropoietin having a reduced carbohydrate content by treatment of native erythropoietin with at least one glycosidase; iv) an erythropoietin having at least one or more oxidized carbohydrates; v) an erythropoietin comprising at least one or more oxidized carbohydrates which is chemically reduced; vi) an erythropoietin comprising at least one or more modified arginine residues; vii) an erythropoietin comprising at least one or more modified lysine residues or a modification of the N-terminal amino group of the erythropoietin molecule; viii) an erythropoietin comprising at least a modified tyrosine residue; ix) an erythropoietin comprising at least a modified aspartic acid or a glutamic acid residue; x) an erythropoietin comprising at least a modified tryptophan residue; xi) an erythropoietin having at least one amino group removed; xii) an erythropoietin comprising at least an opening of at least one of the cystine linkages in the erythropoietin molecule; or xiii) a truncated erythropoietin.

In one embodiment, the chemically modified EPO for use in the screening methods of the invention is asialoerythropoietin or phenylglyoxal-erythropoietin. In another embodiment, the chemically modified EPO is capable of traversing an endothelial cell barrier. The endothelial cell barrier can be selected from the group consisting of blood-brain barrier, blood-eye barrier, blood-testis barrier, blood-ovary barrier, and blood-uterus barrier.

The invention also provides for a chemically modified EPO for use in the screening methods of invention that is an erythropoietin. In preferred embodiments, the asialoerythropoietin is human asialoerythropoietin. The chemically modified EPO is preferably an erythropoietin with no N-linked carbohydrates. The chemically modified EPO is preferably an erythropoietin with no O-linked carbohydrates. In one embodiment, the chemically modified EPO is an erythropoietin treated with at least one glycosidase. In another embodiment, the chemically modified EPO is periodate-oxidized erythropoietin. The periodate-oxidized erythropoietin is preferably chemically reduced with sodium cyanoborohydride. In one embodiment, the chemically modified EPO is an erythropoietin comprising a R-glyoxal moiety on the one or more arginine residues, wherein R is aryl or alkyl moiety. The erythropoietin is preferably phenylglyoxal-erythropoietin. In another embodiment, the chemically modified EPO is an erythropoietin in which at least one arginine residue is modified by reaction with a vicinal diketone selected from the group consisting of 2,3-butanedione and cyclohexanedione. In yet another embodiment, the chemically modified EPO of the invention is an erythropoietin in which at least one arginine residue is reacted with 3-deoxyglucosone. In still another embodiment, the chemically modified EPO is an erythropoietin molecule comprising at least one biotinylated lysine or N-terminal amino group. The erythropoietin molecule can be a biotinylated erythropoietin.

The invention also provides for a chemically modified EPO that is a glucitolyl lysine erythropoietin or a fructosyl lysine erythropoietin.

In one embodiment, the chemically modified EPO of the screening methods of invention is an erythropoietin having at least one carbamylated lysine residue. In another embodiment, the carbamylated erythropoietin is selected from the group consisting of alpha-N-carbamoylerythropoietin; N-epsilon-carbamoylerythropoietin; alpha-N-carbamoyl, N-epsilon-carbamoylerythropoietin; alpha-N-carbamoylasialoerythropoietin; N-epsilon-carbamoylasialoerythropoietin; alpha-N-carbamoyl, N-epsilon-carbamoylasialoerythropoietin; alpha-N-carbamoylhyposialoerythropoietin; N-epsilon-carbamoylhyposialoerythropoietin; and alpha-N-carbamoyl, N-epsilon-carbamoylhyposialoerythropoietin.

In one embodiment, the chemically modified EPO of the screening methods of invention is an erythropoietin in which at least one lysine residue is acylated. In another embodiment, a lysine residue of said erythropoietin is acetylated. In yet another embodiment, the acetylated erythropoietin is selected from the group consisting of alpha-N-acetylerythropoietin; N-epsilon-acetylerythropoietin; alpha-N-acetyl, N-epsilon-acetylerythropoietin; alpha-N-acetylasialoerythropoietin; N-epsilon-acetylasialoerythropoietin; alpha-N-acetyl, N-epsilon-acetylasialoerythropoietin; alpha-N-acetylhyposialoerythropoietin; N-epsilon-acetylhyposialoerythropoietin; and alpha-N-acetyl, N-epsilon-acetylhyposialoerythropoietin.

In one embodiment, the chemically modified EPO of the invention is an erythropoietin comprising a succinylated lysine residue. In one embodiment, the erythropoietin is selected from the group consisting of alpha-N-succinylerythropoietin; N-epsilon-succinylerythropoietin; alpha-N-succinyl, N-epsilon-succinylerythropoietin; alpha-N-succinylasialoerythropoietin; N-epsilon-succinylasialoerythropoietin; alpha-N-succinyl, N-epsilon-succinylasialoerythropoietin; alpha-N-succinylhyposialoerythropoietin; N-epsilon-succinylhyposialoerythropoietin; and alpha-N-succinyl, N-epsilon-succinylhyposialoerythropoietin.

In one embodiment, the chemically modified EPO of the screening methods of invention is an erythropoietin with at least one lysine residue modified by a 2, 4, 6-trinitrobenzenesulfonic acid salt. In one aspect of the invention, the salt is 2, 4, 6-trinitrobenzenesulfonate sodium.

In another embodiment, the chemically modified EPO of the screening methods of invention is an erythropoietin in which at least one tyrosine residue is nitrated and/or iodinated.

In yet another embodiment, the chemically modified EPO of the screening methods of invention is an erythropoietin in which an aspartic acid and/or glutamic acid residue is reacted with a carbodiimide followed by reaction with an amine. In one aspect of the invention the amine is glycinamide.

Mutant EPO molecules can also be used, for example, the tissue protective cytokine receptor complex ligand may be a mutant EPO, which may be recombinantly produced, comprising one or more altered amino acid residue between position 11 to 15 of SEQ ID NO:10 [SEQ ID NO:1], position 44 to 51 of SEQ ID NO 10 [SEQ ID NO:2], position 100-108 of SEQ ID NO [SEQ ID NO:3], or position 146-151 of SEQ ID NO 10 [SEQ ID NO:4].

In another embodiment, the tissue protective cytokine receptor complex ligand is a mutant EPO comprising an altered amino acid residue at one or more of the following positions of SEQ ID NO: 10: 7, 20, 21, 29, 33, 38, 42, 59, 63, 67, 70, 83, 96, 126, 142, 143, 152, 153, 155, 156, or 161.

In yet another embodiment, the tissue protective cytokine receptor complex ligand is a mutant EPO comprising the amino acid sequence of SEQ ID NO: 10 with one or more of the following changes (each altered sequence has been assigned a separate sequence identification number): an alanine at residue 6 of SEQ ID NO: 10 (SEQ ID NO: 15); an alanine at residue 7 of SEQ ID NO: 10 (SEQ ID NO: 16); a serine at residue 7 of SEQ ID NO: 10 (SEQ ID NO: 17); an isoleucine at residue 10 of SEQ ID NO: 10 (SEQ ID NO: 18); a serine at residue 11 of SEQ ID NO: 10 (SEQ ID NO: 19); an alanine at residue 12 of SEQ ID NO: 10 (SEQ ID NO: 20); an alanine at residue 13 of SEQ ID NO: 10 (SEQ ID NO: 21); an alanine residue 14 of SEQ ID NO: 10 (SEQ ID NO: 22); a glutamic acid at residue 14 of SEQ ID NO: 10 (SEQ ID NO: 23); a glutamine at residue 14 of SEQ ID NO: 10 (SEQ ID NO: 24); an alanine at residue 15 of SEQ ID NO: 10 (SEQ ID NO: 25); a phenylalanine at residue 15 of SEQ ID NO: 10 (SEQ ID NO: 26); an isoleucine at residue 15 of SEQ ID NO: 10 (SEQ ID NO: 27); a glutamic acid at residue 20 of SEQ ID NO: 10 (SEQ ID NO: 28); an alanine at residue 20 of SEQ ID NO: 10 (SEQ ID NO: 29); an alanine at residue 21 of SEQ ID NO: 10 (SEQ ID NO: 30); a lysine at residue 24 of SEQ ID NO: 10 (SEQ ID NO: 31); a serine at residue 29 of SEQ ID NO: 10 (SEQ ID NO: 32); a tyrosine at residue 29 of SEQ ID NO: 10 (SEQ ID NO: 33); an asparagine at residue 30 of SEQ ID NO: 10 (SEQ ID NO: 34); a threonine at residue 32 of SEQ ID NO: 10 (SEQ ID NO: 35); a serine at residue 33 of SEQ ID NO: 10 (SEQ ID NO: 36); a tyrosine at residue 33 of SEQ ID NO: 10 (SEQ ID NO: 37); a lysine at residue 38 of SEQ ID NO: 10 (SEQ ID NO: 38); a lysine at residue 83 of SEQ ID NO: 10 (SEQ ID NO: 39); an asparagine at residue 42 of SEQ ID NO: 10 (SEQ ID NO: 40); an alanine at residue 42 of SEQ ID NO: 10 (SEQ ID NO: 41); an alanine at residue 43 of SEQ ID NO: 10 (SEQ ID NO: 42); an isoleucine at residue 44 of SEQ ID NO: 10 (SEQ ID NO: 43); an aspartic acid at residue 45 of SEQ ID NO: 10 (SEQ ID NO: 44); an alanine at residue 45 of SEQ ID NO: 10 (SEQ ID NO: 45); an alanine at residue 46 of SEQ ID NO: 10 (SEQ ID NO: 46); an alanine at residue 47 of SEQ ID NO: 10 (SEQ ID NO: 47); an isoleucine at residue 48 of SEQ ID NO: 10 (SEQ ID NO: 48); an alanine at residue 48 of SEQ ID NO: 10 (SEQ ID NO: 49); an alanine at residue 49 of SEQ ID NO: 10 (SEQ ID NO: 50); a serine at residue 49 of SEQ ID NO: 10 (SEQ ID NO: 51); a phenylalanine at residue 51 of SEQ ID NO: 10 (SEQ ID NO: 52); an asparagine at residue 51 of SEQ ID NO: 10 (SEQ ID NO: 53); an alanine at residue 52 of SEQ ID NO: 10 (SEQ ID NO: 54); an asparagine at residue 59 of SEQ ID NO: 10 (SEQ ID NO: 55); a threonine at residue 62 of SEQ ID NO: 10 (SEQ ID NO: 56); a serine at residue 67 of SEQ ID NO: 10 (SEQ ID NO: 57); an alanine at residue 70 of SEQ ID NO: 10 (SEQ ID NO: 58); an arginine at residue 96 of SEQ ID NO: 10 (SEQ ID NO: 59); an alanine at residue 97 of SEQ ID NO: 10 (SEQ ID NO: 60); an arginine at residue 100 of SEQ ID NO: 10 (SEQ ID NO: 61); a glutamic acid at residue 100 of SEQ ID NO: 10 (SEQ ID NO: 62); an alanine at residue 100 of SEQ ID NO: 10 (SEQ ID NO: 63); a threonine at residue 100 of SEQ ID NO: 10 (SEQ ID NO: 64); an alanine at residue 101 of SEQ ID NO: 10 (SEQ ID NO: 65); an isoleucine at residue 101 of SEQ ID NO: 10 (SEQ ID NO: 66); an alanine at residue 102 of SEQ ID NO: 10 (SEQ ID NO: 67); an alanine at residue 103 of SEQ ID NO: 10 (SEQ ID NO: 68); a glutamic acid at residue 103 of SEQ ID NO: 10 (SEQ ID NO: 69); an alanine at residue 104 of SEQ ID NO: 10 (SEQ ID NO: 70); an isoleucine at residue 104 of SEQ ID NO: 10 (SEQ ID NO: 71); an alanine at residue 105 of SEQ ID NO: 10 (SEQ ID NO: 72); an alanine at residue 106 of SEQ ID NO: 10 (SEQ ID NO: 73); an isoleucine at residue 106 of SEQ ID NO: 10 (SEQ ID NO: 74); an alanine at residue 107 of SEQ ID NO: 10 (SEQ ID NO: 75); a leucine at residue 107 of SEQ ID NO: 10 (SEQ ID NO: 76); a lysine at residue 108 of SEQ ID NO: 10 (SEQ ID NO: 77); an alanine at residue 108 of SEQ ID NO: 10 (SEQ ID NO: 78); a serine at residue 108 of SEQ ID NO: 10 (SEQ ID NO: 79); an alanine at residue 116 of SEQ ID NO: 10 (SEQ ID NO: 80); an alanine at residue 126 of SEQ ID NO: 10 (SEQ ID NO: 81); an alanine at residue 132 of SEQ ID NO: 10 (SEQ ID NO: 82); an alanine at residue 133 of SEQ ID NO: 10 (SEQ ID NO: 83); an alanine at residue 134 of SEQ ID NO: 10 (SEQ ID NO: 84); an alanine at residue 140 of SEQ ID NO: 10 (SEQ ID NO: 85); an isoleucine at residue 142 of SEQ ID NO: 10 (SEQ ID NO: 86); an alanine at residue 143 of SEQ ID NO: 10 (SEQ ID NO: 87); an alanine at residue 146 of SEQ ID NO: 10 (SEQ ID NO: 88); a lysine at residue 147 of SEQ ID NO: 10 (SEQ ID NO: 89); an alanine at residue 147 of SEQ ID NO: 10 (SEQ ID NO: 90); a tyrosine at residue 148 of SEQ ID NO: 10 (SEQ ID NO: 91); an alanine at residue 148 of SEQ ID NO: 10 (SEQ ID NO: 92); an alanine at residue 149 of SEQ ID NO: 10 (SEQ ID NO: 93); an alanine at residue 150 of SEQ ID NO: 10 (SEQ ID NO: 94); a glutamic acid at residue 150 of SEQ ID NO: 10 (SEQ ID NO: 95); an alanine at residue 151 of SEQ ID NO: 10 (SEQ ID NO: 96); an alanine at residue 152 of SEQ ID NO: 10 (SEQ ID NO: 97); a tryptophan at residue 152 of SEQ ID NO: 10 (SEQ ID NO: 98); an alanine at residue 153 of SEQ ID NO: 10 (SEQ ID NO: 99); an alanine at residue 154 of SEQ ID NO: 10 (SEQ ID NO: 100); an alanine at residue 155 of SEQ ID NO: 10 (SEQ ID NO: 101); an alanine at residue 158 of SEQ ID NO: 10 (SEQ ID NO: 102); a serine at residue 160 of SEQ ID NO: 10 (SEQ ID NO: 103); an alanine at residue 161 of SEQ ID NO: 10 (SEQ ID NO: 104); or an alanine at residue 162 of SEQ ID NO: 10 (SEQ ID NO: 105). In one embodiment, the tissue protective cytokine receptor complex ligand is a mutant EPO that comprises the amino acid sequence of SEQ ID NO: 10 with one or more of the amino acid residue substitutions of SEQ ID NOs: 15-105 and 119.

In yet another embodiment, the tissue protective cytokine receptor complex ligand is a mutant EPO that comprises the amino acid sequence of SEQ ID NO: 10 with a deletion of amino acid residues 44-49 of SEQ ID NO: 10.

In still another embodiment, the tissue protective cytokine receptor complex ligand is a mutant EPO that comprises the amino acid sequence of SEQ ID NO: 10 with at least one of the following changes (each altered sequence has been assigned a separate sequence identification number): i) an aspartic acid at residue 45, and a glutamic acid at residue 100 of SEQ ID NO: 10 (SEQ ID NO: 106); ii) an asparagine at residue 30, a threonine at residue 32 of SEQ ID NO: 10 (SEQ ID NO: 107); iii) an aspartic acid at residue 45, a glutamic acid at residue 150 SEQ ID NO: 10 (SEQ ID NO: 108); iv) a glutamic acid at residue 103, and a serine at residue 108 of SEQ ID NO: 10 (SEQ ID NO: 109); v) an alanine at residue 140 and an alanine at residue 52 of SEQ ID NO: 10 (SEQ ID NO: 110); vi) an alanine at residue 140, an alanine at residue 52, an alanine at residue 45 of SEQ ID NO: 10 (SEQ ID NO: 111); vii) an alanine at residue 97, and an alanine at residue 152 of SEQ ID NO: 10 (SEQ ID NO: 112); xiii) an alanine at residue 97, an alanine at residue 152, an alanine at residue 45 of SEQ ID NO: 10 (SEQ ID NO: 113); ix) an alanine at residue 97, an alanine at residue 152, an alanine at residue 45, and an alanine at residue 52 of SEQ ID NO: 10 (SEQ ID NO: 114); x) an alanine at residue 97, an alanine at residue 152, an alanine at residue 45, an alanine at residue 52, and an alanine at residue 140 of SEQ ID NO: 10 (SEQ ID NO: 115); xi) an alanine at residue 97, an alanine at residue 152, an alanine at residue 45, an alanine at residue 52, an alanine at residue 140, an alanine at residue 154, a lysine at residue 24, a lysine at residue 38, a lysine at residue 83, a lysine at residue 24 and an alanine at residue 15 of SEQ ID NO: 10 (SEQ ID NO: 116); xii) a lysine at residue 24, a lysine at residue 38, and a lysine at residue 83 SEQ ID NO: 10 (SEQ ID NO: 117); or xiii) a lysine at residue 24 and an alanine at residue 15 SEQ ID NO: 10 (SEQ ID NO: 118). In one embodiment, the tissue protective cytokine receptor complex ligand is a mutant EPO that comprises the amino acid sequence of SEQ ID NO: 10 with at least one of the following amino acid residue substitutions of SEQ ID NOs: 106-118.

The tissue protective cytokine receptor complex ligand is a mutant EPO and may comprise the amino acid sequence of SEQ ID NO: 10 with at least one of the following changes, i.e. substitutions, (each change or combination of changes listed has been assigned a separate sequence identification number): i) an aspartic acid at residue 45, and a glutamic acid at residue 100 of SEQ ID NO: 10 (SEQ ID NO: 106); ii) an asparagine at residue 30, a threonine at residue 32 of SEQ ID NO: 10 (SEQ ID NO: 107); iii) an aspartic acid at residue 45, a glutamic acid at residue 150 SEQ ID NO: 10 (SEQ ID NO:

108); iv) a glutamic acid at residue 103, and a serine at residue 108 of SEQ ID NO: 10 (SEQ ID NO: 109); v) an alanine at residue 140 and an alanine at residue 52 of SEQ ID NO: 10 (SEQ ID NO: 110); vi) an alanine at residue 140, an alanine at residue 52, an alanine at residue 45 of SEQ ID NO: 10 (SEQ ID NO: 111); vii) an alanine at residue 97, and an alanine at residue 152 of SEQ ID NO: 10 (SEQ ID NO: 112); xiii) an alanine at residue 97, an alanine at residue 152, an alanine at residue 45 of SEQ ID NO: 10 (SEQ ID NO: 113); ix) an alanine at residue 97, an alanine at residue 152, an alanine at residue 45, and an alanine at residue 52 of SEQ ID NO: 10 (SEQ ID NO: 114); x) an alanine at residue 97, an alanine at residue 152, an alanine at residue 45, an alanine at residue 52, and an alanine at residue 140 of SEQ ID NO: 10 (SEQ ID NO: 115); xi) an alanine at residue 97, an alanine at residue 152, an alanine at residue 45, an alanine at residue 52, an alanine at residue 140, an alanine at residue 154, a lysine at residue 24, a lysine at residue 38, a lysine at residue 83, a lysine at residue 24 and an alanine at residue 15 of SEQ ID NO: 10 (SEQ ID NO: 116); xii) a lysine at residue 24, a lysine at residue 38, and a lysine at residue 83 SEQ ID NO: 10 (SEQ ID NO: 117); or xiii) a lysine at residue 24 and an alanine at residue 15 SEQ ID NO: 10 (SEQ ID NO: 118).

According to another aspect of the invention, the tissue protective cytokine receptor complex ligand is a mutant EPO comprising at least one of the following amino acid residue substitutions: (each change or combination of changes listed has been assigned a separate sequence identification number): a tryptophan at residue 152 of SEQ ID NO: 10 (SEQ ID NO: 98); an alanine at residue 14 and an alanine at residue 15 of SEQ ID NO: 10 (SEQ ID NO: 119); an alanine at residue 6 of SEQ ID NO: 10 (SEQ ID NO: 15); an alanine at residue 7 of SEQ ID NO: 10 (SEQ ID NO: 16); an alanine at residue 43 of SEQ ID NO: 10 (SEQ ID NO: 42); an alanine at residue 42 of SEQ ID NO: 10 (SEQ ID NO: 41); an alanine at residue 48 of SEQ ID NO: 10 (SEQ ID NO: 49); an alanine at residue 49 of SEQ ID NO: 10 (SEQ ID NO: 50); an threonine at residue 32 of SEQ ID NO: 10 (SEQ ID NO: 35); an alanine at residue 133 of SEQ ID NO: 10 (SEQ ID NO: 83); an alanine at residue 134 of SEQ ID NO: 10 (SEQ ID NO: 84); an alanine at residue 147 of SEQ ID NO: 10 (SEQ ID NO: 90); an alanine at residue 148 of SEQ ID NO: 10 (SEQ ID NO: 92); an alanine at residue 150 of SEQ ID NO: 10 (SEQ ID NO: 94); an alanine at residue 151 of SEQ ID NO: 10 (SEQ ID NO: 96); an alanine at residue 158 of SEQ ID NO: 10 (SEQ ID NO: 102); an alanine at residue 161 of SEQ ID NO: 10 (SEQ ID NO: 104); or an alanine at residue 162 of SEQ ID NO: 10 (SEQ ID NO: 105).

5.4.1.2 Antibodies

In certain embodiments of the invention the compound tested in the screening assays above is an antibody. The ligand may also be an antibody specific for a tissue protective receptor cytokine receptor complex in screening assays designed to identify compounds that modulate the interaction of a known ligand with the tissue protective receptor cytokine receptor complex. Described herein are methods for the production of such antibodies. The antibodies identified may also be useful for tissue protection.

Such antibodies may include, but are not limited to, polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above. Such antibodies may be utilized in conjunction with, for example, compound screening schemes, as described above, for the evaluation of the effect of test compounds on activity of a tissue protective receptor cytokine receptor complex or a tissue protective activity.

For the production of antibodies specific to a tissue protective receptor cytokine receptor complex, various host animals may be immunized by injection with an tissue protective receptor cytokine receptor complex, or a portion thereof. An antigenic portion of tissue protective receptor cytokine receptor complex can be readily predicted by algorithms known in the art.

Host animals may include, but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Polyclonal antibodies are heterogeneous populations of antibody molecules derived from the sera of animals immunized with an antigen, such as a tissue protective receptor cytokine receptor complex, or an antigenic functional derivative thereof. For the production of polyclonal antibodies, host animals such as those described above, may be immunized by injection with tissue protective receptor cytokine receptor complex, or portion thereof, supplemented with adjuvants as also described above.

Monoclonal antibodies, which are homogeneous populations of antibodies to a particular antigen, may be obtained by any technique that provides for the production of antibody molecules by continuous cell lines in culture. These include, but are not limited to, the hybridoma technique of Kohler and Milstein, (1975, Nature 256, 495-497; and U.S. Pat. No. 4,376,110), the human B-cell hybridoma technique (Kosbor et al., 1983, Immunology Today 4: 72; Cole et al., 1983, Proc. Natl. Acad. Sci. USA 80, 2026-2030), and the EBV-hybridoma technique (Cole et al., 1985, Monoclonal Antibodies And Cancer Therapy, Alan R. Liss, Inc., pp. 77-96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81: 6851-6855; Neuberger et al., 1984, Nature 312: 604-608; Takeda et al., 1985, Nature, 314: 452-454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region (see, e.g., Cabilly et al., U.S. Pat. No. 4,816,567; and Boss et al., U.S. Pat. No. 4,816,397, which are incorporated herein by reference in their entirety).

In an additional embodiment of the invention, monoclonal antibodies can be produced in germ-free animals (see PCT International Publication No. WO 89/12690, published Dec. 12, 1989). According to the invention, human antibodies may be used and can be obtained by using human hybridomas (Cote et al., 1983, Proc. Natl. Acad. Sci. U.S.A. 80:2026-2030) or by transforming human B cells with EBV virus in vitro (Cole et al., 1985, in Monoclonal Antibodies and Cancer Therapy, Alan R. Liss, pp. 77-96). Techniques developed for the production of "chimeric antibodies" (Morrison et al., 1984, Proc. Natl. Acad. Sci. U.S.A. 81:6851-6855; Neuberger et al., 1984, Nature 312:604-608; Takeda et al., 1985, Nature 314:452-454) by splicing the genes from a mouse antibody molecule specific for a tissue protective receptor cytokine receptor complex together with genes from a human antibody molecule of appropriate biological activity can also be used; such antibodies are within the scope of this invention.

Humanized antibodies are also provided (see U.S. Pat. No. 5,225,539 by Winter). An immunoglobulin light or heavy chain variable region consists of a "framework" region interrupted by three hypervariable regions, referred to as complementarity determining regions (CDRs). The extent of the framework region and CDRs have been precisely defined (see, "Sequences of Proteins of Immunological Interest", Kabat, E. et al., U.S. Department of Health and Human Services (1983). Briefly, humanized antibodies are antibody molecules from non-human species having one or more CDRs from the non-human species and a framework region from a human immunoglobulin molecule. Such CDRS-grafted antibodies have been successfully constructed against various antigens, for example, antibodies against IL-2 receptor as described in Queen et al., 1989, Proc. Natl. Acad. Sci. USA 86:10029; antibodies against the cell surface receptor CAMPATH as described in Riechmann et al., 1988, Nature 332:323; antibodies against hepatitis B in Co et al., 1991, Proc. Natl. Acad. Sci. USA 88:2869; as well as against viral antigens of the respiratory syncytial virus in Tempest et al., 1991, Bio-Technology 9:267. Humanized antibodies are most preferred for therapeutic use in humans.

Alternatively, techniques described for the production of single chain antibodies (U.S. Pat. No. 4,946,778; Bird, 1988, Science 242: 423-426; Huston et al., 1988, Proc. Natl. Acad. Sci. USA 85: 5879-5883; and Ward et al., 1989, Nature 334: 544-546) can be adapted to produce single chain antibodies specific for a tissue protective receptor cytokine receptor complex, or portions thereof. Single chain antibodies are formed by linking the heavy and light chain fragments of the Fv region via an amino acid bridge, resulting in a single chain polypeptide.

Antibody fragments that recognize specific epitopes may be generated by known techniques. For example, such fragments include but are not limited to: the F(ab')$_2$ fragments, which can be produced by pepsin digestion of the antibody molecule and the Fab fragments, which can be generated by reducing the disulfide bridges of the F(ab')$_2$ fragments. Alternatively, Fab expression libraries may be constructed (Huse et al., 1989, Science, 246: 1275-1281) to allow rapid and easy identification of monoclonal Fab fragments with the desired specificity.

Antibodies to a tissue protective receptor cytokine receptor complex can, in turn, be utilized to generate anti-idiotype antibodies that "mimic" the tissue protective receptor cytokine receptor complex, using techniques well known to those skilled in the art (see, e.g., Greenspan & Bona, 1993, FASEB J 7(5):437-444; and Nissinoff, 1991, J. Immunol. 147(8): 2429-2438). For example antibodies which bind to the tissue protective receptor cytokine receptor complex and competitively inhibit the binding of EPO or other known ligands to the tissue protective receptor cytokine receptor complex can be used to generate anti-idiotypes that "mimic" the binding domain of the tissue protective receptor cytokine receptor complex and, therefore, bind and neutralize tissue protective receptor cytokine receptor complex ligands. Such neutralizing anti-idiotypes or Fab fragments of such anti-idiotypes can be used in therapeutic regimens to neutralize the native ligand, which can be followed by administration of a compound identified by the methods of the invention that provides tissue protection, which may be superior in comparison to the protection provided by a native ligand. Alternatively, antibodies to the tissue protective receptor cytokine receptor complex that can act as agonists of the tissue protective receptor cytokine receptor complex activity can be generated. Such antibodies will bind to the tissue protective receptor cytokine receptor complex and activate the signal transducing activity of the receptor complex. In addition, antibodies that act as antagonist of the tissue protective receptor cytokine receptor complex activity, i.e. inhibit the activation of the tissue protective receptor cytokine receptor complex would be useful as a negative control in assays for identifying compounds that modulate the activity of a tissue protective receptor cytokine receptor complex. Methods for assaying for such agonists and antagonists are described in detail in the sections above.

5.4.2 Characterization of the Structure of Compounds

The structure of a test compound identified by the screening methods of the invention can be determined various methods by known to those of skill in the art. For example, X-ray crystallography can be used to elucidate the structure of a compound. For a review of x-ray crystallography see, e.g., Blundell et al. 2002, Nat Rev Drug Discov 1(1):45-54.

In certain embodiments, vibrational spectroscopy (e.g., but not limited to, infrared (1R) spectroscopy or Raman spectroscopy) can be used for elucidating the structure of a compound. An improved Raman spectrometer is described in U.S. Pat. No. 5,786,893 to Fink et al., which is hereby incorporated by reference. Vibrational microscopy can be measured in a spatially resolved fashion to address single beads by integration of a visible microscope and spectrometer. A microscopic infrared spectrometer is described in U.S. Pat. No. 5,581,085 to Reffler et al., which is hereby incorporated by reference in its entirety. An instrument that simultaneously performs a microscopic infrared and microscopic Raman analysis on a sample is described in U.S. Pat. No. 5,841,139 to Sostek et al., which is hereby incorporated by reference in its entirety. In one embodiment of the method, compounds are synthesized on polystyrene beads doped with chemically modified styrene monomers such that each resulting bead has a characteristic pattern of absorption lines in the vibrational (IR or Raman) spectrum, by methods including but not limited to those described by Fenniri et al., 2000, J. Am. Chem. Soc. 123:8151-8152. Using methods of split-pool synthesis familiar to one of skill in the art, the library of compounds is prepared so that the spectroscopic pattern of the bead identifies one of the components of the compound on the bead. Beads that have been separated according to their ability to bind a tissue protective cytokine receptor complex can be identified by their vibrational spectrum.

Mass spectrometry (e.g., electrospray ionization ("ESI") and matrix-assisted laser desorption-ionization ("MALDI"), Fourier-transform ion cyclotron resonance ("FT-ICR") can be used both for high-throughput screening of compounds that bind to a tissue protective cytokine receptor complex and elucidating the structure of the compound.

MALDI uses a pulsed laser for desorption of the ions and a time-of-flight analyzer, and has been used for the detection of noncovalent tRNA:amino-acyl-tRNA synthetase complexes (Gruic-Sovulj et al., 1997, J. Biol. Chem. 272:32084-32091). However, covalent cross-linking between the target nucleic acid and the compound is usually required for detection, since a non-covalently bound complex may dissociate during the MALDI process.

ESI mass spectrometry ("ESI-MS") has been of greater utility for studying non-covalent molecular interactions because, unlike the MALDI process, ESI-MS generates molecular ions with little to no fragmentation (Xavier et al., 2000, Trends Biotechnol. 18(8):349-356). ESI-MS has been used to study the complexes formed by HIV Tat peptide and protein with the TAR RNA (Sannes-Lowery et al., 1997, Anal. Chem. 69:5130-5135).

Fourier-transform ion cyclotron resonance ("FT-ICR") mass spectrometry provides high-resolution spectra, isotope-resolved precursor ion selection, and accurate mass assignments (Xavier et al., 2000, Trends Biotechnol. 18(8):349-356). FT-ICR has been used to study the interaction of aminoglycoside antibiotics with cognate and non-cognate RNAs (Hofstadler et al., 1999, Anal. Chem. 71:3436-3440; Griffey et al., 1999, Proc. Natl. Acad. Sci. USA 96:10129-10133). As true for all of the mass spectrometry methods discussed herein, FT-ICR does not require labeling of the tissue protective cytokine receptor complex or a compound.

An advantage of mass spectroscopy is not only the elucidation of the structure of a compound, but also the determination of the structure of the compound bound to a tissue protective cytokine receptor complex. Such information can enable the discovery of a consensus structure of a compound that specifically binds to a tissue protective cytokine receptor complex.

NMR spectroscopy methods can also be used to characterize compounds that are associated with a tissue protective cytokine receptor complex. For example, complexed molecules can be examined by qualitatively determining changes in chemical shift, specifically from distances measured using relaxation effects, and NMR-based approaches have been used in the identification of small molecule binders of protein drug targets (Xavier et al., 2000, Trends Biotechnol. 18(8): 349-356). The determination of structure-activity relationships ("SAR") by NMR is the first method for NMR described in which small molecules that bind adjacent subsites are identified by two-dimensional $^1$H-$^{15}$N spectra of the target protein (Shuker et al., 1996, Science 274:1531-1534). The signal from the bound molecule is monitored by employing line broadening, transferred NOEs and pulsed field gradient diffusion measurements (Moore, 1999, Curr. Opin. Biotechnol. 10:54-58). A strategy for lead generation by NMR using a library of small molecules has been recently described (Fejzo et al., 1999, Chem. Biol. 6:755-769).

Other examples of NMR methods that can be used for the invention include, but are not limited to, one-dimensional, two-dimensional, three dimension, four dimensional NMR methods as well as correlation spectroscopy ("COSY"), and nuclear Overhauser effect ("NOE") spectroscopy. Such methods of structure determination of compounds are well known to one of skill in the art.

Similar to mass spectroscopy, an advantage of NMR is the not only the elucidation of the structure of a compound, but also the determination of the structure of the compound bound to a tissue protective cytokine receptor complex.

5.5 Therapeutic Use

One of ordinary skill in the art would recognize that compounds identified by the present assays, are useful as therapeutics for various diseases. The therapeutic indications and possible methods of administration for tissue protective compounds identified by the inventive assays disclosed above are disclosed in PCT Application No. PCT/US01/49479, U.S. patent application Ser. Nos. 10/188,905 and 10/185,841, incorporated herein by reference.

The aforementioned compounds identified by the methods of the invention may be useful generally for the therapeutic or prophylactic treatment of human diseases of the central nervous system or peripheral nervous system which have primarily neurological or psychiatric symptoms, ophthalmic diseases, cardiovascular diseases, cardiopulmonary diseases, respiratory diseases, kidney, urinary and reproductive diseases, bone diseases, skin diseases, gastrointestinal diseases and endocrine and metabolic abnormalities. In particular, such conditions and diseases include hypoxic conditions, which adversely affect excitable tissues, such as excitable tissues in the central nervous system tissue, peripheral nervous system tissue, or cardiac tissue or retinal tissue such as, for example, brain, heart, or retina/eye. Therefore, the compounds identified by the methods of the invention can be used to treat or prevent damage to excitable tissue resulting from hypoxic conditions in a variety of conditions and circumstances. Non-limiting examples of such conditions and circumstances are provided in the table herein below.

In the example of the protection of neuronal tissue pathologies treatable using compounds identified by the methods of the invention, such pathologies include those which result from reduced oxygenation of neuronal tissues. Any condition which reduces the availability of oxygen to neuronal tissue, resulting in stress, damage, and finally, neuronal cell death, can be treated using compounds identified by the methods of the present invention. Generally referred to as hypoxia and/or ischemia, these conditions arise from or include, but are not limited to, stroke, vascular occlusion, prenatal or postnatal oxygen deprivation, suffocation, choking, near drowning, carbon monoxide poisoning, smoke inhalation, trauma, including surgery and radiotherapy, asphyxia, epilepsy, hypoglycemia, chronic obstructive pulmonary disease, emphysema, adult respiratory distress syndrome, hypotensive shock, septic shock, anaphylactic shock, insulin shock, sickle cell crisis, cardiac arrest, dysrhythmia, nitrogen narcosis, and neurological deficits caused by heart-lung bypass procedures.

In one embodiment, for example, the compounds identified by the methods of the present invention identified using the inventive assay could be administered alone or as part of a composition to prevent injury or tissue damage resulting from risk of injury or tissue damage during surgical procedures, such as, for example, tumor resection or aneurysm repair. Other pathologies caused by or resulting from hypoglycemia which are treatable using compounds identified by the methods of the present invention include insulin overdose, also referred to as iatrogenic hyperinsulinemia, insulinoma, growth hormone deficiency, hypocortisolism, drug overdose, and certain tumors.

Other pathologies resulting from excitable neuronal tissue damage include seizure disorders, such as epilepsy, convulsions, or chronic seizure disorders. Other treatable conditions and diseases include, but are not limited to, diseases such as stroke, multiple sclerosis, hypotension, cardiac arrest, Alzheimer's disease, Parkinson's disease, cerebral palsy, brain or spinal cord trauma, AIDS dementia, age-related loss of cognitive function, memory loss, amyotrophic lateral sclerosis, seizure disorders, alcoholism, retinal ischemia, optic nerve damage resulting from glaucoma, and neuronal loss.

The specific compounds identified by the methods of the present invention may be used to treat inflammation resulting from disease conditions or various traumas, such as physically or chemically induced inflammation. Such traumas could include angitis, chronic bronchitis, pancreatitis, osteomyelitis, rheumatoid arthritis, glomerulonephritis, optic neuritis, temporal arteritis, encephalitis, meningitis, transverse myelitis, dermatomyositis, polymyositis, necrotizing fasciitis, hepatitis, and necrotizing enterocolitis.

The compounds identified by the methods of the present invention may be used to treat conditions of, and damage to, retinal tissue. Such disorders include, but are not limited to retinal ischemia, macular degeneration, retinal detachment, retinitis pigmentosa, arteriosclerotic retinopathy, hypertensive retinopathy, retinal artery blockage, retinal vein blockage, hypotension, and diabetic retinopathy.

In another embodiment, the compounds identified by the methods of the present invention and principles of the invention may be used to protect or treat injury resulting from radiation damage to excitable tissue. A further utility of the compounds identified by the methods of the present invention is in the treatment of neurotoxin poisoning, such as domoic acid shellfish poisoning, neurolathyrism, and Guam disease, amyotrophic lateral sclerosis, and Parkinson's disease.

As mentioned above, the present invention is also directed to compounds identified by the methods of the present invention for use in enhancing excitable tissue function in a mammal by peripheral administration of a tissue protective cytokine as described above. Various diseases and conditions are amenable to treatment using this method, and further, this method is useful for enhancing cognitive function in the absence of any condition or disease. These uses of the present invention are describe in further detail below and include enhancement of learning and training in both human and non-human mammals.

Conditions and diseases treatable using compounds identified by the methods of the present invention directed to the central nervous system include but are not limited to mood disorders, anxiety disorders, depression, autism, attention deficit hyperactivity disorder, and cognitive dysfunction. These conditions benefit from enhancement of neuronal function. Other disorders treatable in accordance with the teachings of the present invention include sleep disruption, for example, sleep apnea and travel-related disorders; subarachnoid and aneurismal bleeds, hypotensive shock, concussive injury, septic shock, anaphylactic shock, and sequelae of various encephalitides and meningitides, for example, connective tissue disease-related cerebritides such as lupus. Other uses include prevention of or protection from poisoning by neurotoxins, such as domoic acid shellfish poisoning, neurolathyrism, and Guam disease, amyotrophic lateral sclerosis, Parkinson's disease; postoperative treatment for embolic or ischemic injury; whole brain irradiation; sickle cell crisis; and eclampsia.

A further group of conditions treatable using compounds identified by the methods of the present invention include mitochondrial dysfunction, of either a hereditary or acquired nature, which are the cause of a variety of neurological diseases typified by neuronal injury and death. For example, Leigh disease (subacute necrotizing encephalopathy) is characterized by progressive visual loss and encephalopathy, due to neuronal drop out, and myopathy. In these cases, defective mitochondrial metabolism fails to supply enough high energy substrates to fuel the metabolism of excitable cells. An erythropoietin receptor activity modulator optimizes failing function in a variety of mitochondrial diseases. As mentioned above, hypoxic conditions adversely affect excitable tissues. The excitable tissues include, but are not limited to, central nervous system tissue, peripheral nervous system tissue, and heart tissue. In addition to the conditions described above, the compounds identified by the methods of the present invention are useful in the treatment of inhalation poisoning such as carbon monoxide and smoke inhalation, severe asthma, adult respiratory distress syndrome, and choking and near drowning. Further conditions which create hypoxic conditions or by other means induce excitable tissue damage include hypoglycemia that may occur in inappropriate dosing of insulin, or with insulin-producing neoplasms (insulinoma).

Various neuropsychologic disorders which are believed to originate from excitable tissue damage are treatable using compounds identified by the methods of the present invention. Chronic disorders in which neuronal damage is involved and for which treatment by the present invention is provided include disorders relating to the central nervous system and/or peripheral nervous system including age-related loss of cognitive function and senile dementia, chronic seizure disorders, Alzheimer's disease, Parkinson's disease, dementia, memory loss, amyotrophic lateral sclerosis, multiple sclerosis, tuberous sclerosis, Wilson's Disease, cerebral and progressive supranuclear palsy, Guam disease, Lewy body dementia, prion diseases, such as spongiform encephalopathies, e.g., Creutzfeldt-Jakob disease, Huntington's disease, myotonic dystrophy, Freidrich's ataxia and other ataxias, as well as Gilles de la Tourette's syndrome, seizure disorders such as epilepsy and chronic seizure disorder, stroke, brain or spinal cord trauma, AIDS dementia, alcoholism, autism, retinal ischemia, glaucoma, autonomic function disorders such as hypertension and sleep disorders, and neuropsychiatric disorders that include, but are not limited to schizophrenia, schizoaffective disorder, attention deficit disorder, dysthymic disorder, major depressive disorder, mania, obsessive-compulsive disorder, psychoactive substance use disorders, anxiety, panic disorder, as well as unipolar and bipolar affective disorders. Additional neuropsychiatric and neurodegenerative disorders include, for example, those listed in the American Psychiatric Association's Diagnostic and Statistical manual of Mental Disorders (DSM), the most current version of which in incorporated herein by reference in its entirety.

In another embodiment, recombinant chimeric toxin molecules comprising erythropoietin can be used for therapeutic delivery of toxins to treat a proliferative disorder, such as cancer, or viral disorder, such as subacute sclerosing panencephalitis.

The following table lists additional exemplary, non-limiting indications as to the various conditions and diseases amenable to treatment by the aforementioned tissue protective cytokines.

| Cell, tissue or organ | Dysfunction or pathology | Condition or disease | Type |
|---|---|---|---|
| Heart | Ischemia | Coronary artery disease | Acute, chronic |
|  |  |  | Stable, unstable |
|  |  | Myocardial infarction | Dressler's syndrome |
|  |  | Angina |  |
|  |  | Congenital heart disease | Valvular |
|  |  |  | Cardiomyopathy |

-continued

| Cell, tissue or organ | Dysfunction or pathology | Condition or disease | Type |
|---|---|---|---|
| | | Prinzmetal angina | |
| | | Cardiac rupture | Aneurysmatic |
| | | | Septal perforation |
| | | Angiitis | |
| | Arrhythmia | Tachy-, bradyarrhythmia | Stable, unstable |
| | | Supraventricular, ventricular | Hypersensitive carotid sinus node |
| | | Conduction abnormalities | |
| | Congestive heart failure | Left, right, bi-ventricular, systolic, diastolic | Cardiomyopathies, such as idiopathic familial, infective, metabolic, storage disease, deficiencies, connective tissue disorder, infiltration and granulomas, neurovascular |
| | | Myocarditis | Autoimmune, infective, idiopathic |
| | | Cor pulmonale | |
| | Blunt and penetrating trauma | | |
| | Toxins | Cocaine toxicity | |
| Vascular | Hypertension | Primary, secondary | |
| | Decompression sickness | | |
| | Fibromuscular hyperplasia | | |
| | Aneurysm | Dissecting, ruptured, enlarging | |
| Lungs | Obstructive | Asthma | |
| | | Chronic bronchitis, Emphysema and airway obstruction | |
| | Ischemic lung disease | Pulmonary embolism, Pulmonary thrombosis, Fat embolism | |
| | Environmental lung diseases | | |
| | Ischemic lung disease | Pulmonary embolism Pulmonary thrombosis | |
| | Interstitial lung disease | Idiopathic pulmonary fibrosis | |
| | Congenital | Cystic fibrosis | |
| | Cor pulmonale | | |
| | Trauma | | |
| | Pneumonia and pneumonitides | Infectious, parasitic, toxic, traumatic, burn, aspiration | |
| | Sarcoidosis | | |
| Pancreas | Endocrine | Diabetes mellitus, type I and II | Beta cell failure, dysfunction |
| | | | Diabetic neuropathy |
| | | Other endocrine cell failure of the pancreas | |
| | Exocrine | Exocrine pancreas failure | pancreatitis |
| Bone | Osteopenia | Primary | Hypogonadism |
| | | secondary | immobilisation |
| | | | Postmenopausal |
| | | | Age-related |
| | | | Hyperparathyroidism |
| | | | Hyperthyroidism |
| | | | Calcium, magnesium, phosphorus and/or vitamin D deficiency |
| | Osteomyelitis | | |
| | Avascular necrosis | | |
| | Trauma | | |
| | Paget's disease | | |
| Skin | Alopecia | Areata | Primary |
| | | Totalis | Secondary |
| | | | Male pattern baldness |
| | Vitiligo | Localized | Primary |
| | | generalized | secondary |
| | Diabetic ulceration | | |
| | Peripheral vascular disease | | |
| | Burn injuries | | |
| Autoimmune disorders | Lupus erythematodes, Sjiogren, Rheumatoid arthritis, Glomerulonephritis, | | |

-continued

| Cell, tissue or organ | Dysfunction or pathology | Condition or disease | Type |
|---|---|---|---|
| Eye | Angiitis<br>Langerhan's histiocytosis<br>Optic neuritis<br>Blunt and penetrating injuries, Infections, Sarcoid, Sickle C disease, Retinal detachment, Temporal arteritis<br>Retinal ischemia, Macular degeneration, Retinitis pigmentosa, Arteriosclerotic retinopathy, Hypertensive retinopathy, Retinal artery blockage, Retinal vein blockage, Hypotension, Diabetic retinopathy, and Macular edema | | |
| Embryonic and fetal disorders | Asphyxia<br>Ischemia | | |
| CNS | Chronic fatigue syndrome, acute and chronic hypoosmolar and hyperosmolar syndromes, AIDS Dementia, Electrocution | | |
| | Encephalitis | Rabies, Herpes | |
| | Meningitis<br>Subdural hematoma<br>Nicotine addiction | | |
| | Drug abuse and withdrawal | Cocaine, heroin, crack, marijuana, LSD, PCP, poly-drug abuse, ecstasy, opioids, sedative hypnotics, amphetamines, caffeine | |
| | Obsessive-compulsive disorders<br>Spinal stenosis,<br>Transverse myelitis,<br>Guillian Barre, Trauma,<br>Nerve root compression,<br>Tumoral compression,<br>Heat stroke | | |
| ENT | Tinnitus<br>Meuniere's syndrome<br>Hearing loss<br>Traumatic injury, barotraumas | | |
| Kidney | Renal failure | Acute, chronic | Vascular/ischemic, interstitial disease, diabetic kidney disease, nephrotic syndromes, infections, injury, contrast-induced, chemotherapy-induced, CPB-induced, or preventive |
| | Henoch S. Purpura | | |
| Striated muscle | Autoimmune disorders | Myasthenia gravis<br>Dermatomyositis<br>Polymyositis | |
| | Myopathies | Inherited metabolic, endocrine and toxic | |
| | Heat stroke<br>Crush injury<br>Rhabdomylosis<br>Mitochondrial disease | | |
| | Infection | Necrotizing fasciitis | |
| Sexual dysfunction | Central and peripheral (e.g. erectile dysfunction) | Impotence secondary to medication, (diabetes) | |
| Liver | Hepatitis | Viral, bacterial, parasitic | |
| | Ischemic disease<br>Cirrhosis, fatty liver<br>Infiltrative/metabolic diseases | | |

| Cell, tissue or organ | Dysfunction or pathology | Condition or disease | Type |
|---|---|---|---|
| Gastrointestinal | Ischemic bowel disease |  |  |
|  | Inflammatory bowel disease |  |  |
|  | Necrotizing enterocolitis |  |  |
| Organ transplantation | Treatment of donor and recipient |  |  |
| Reproductive tract | Infertility | Vascular |  |
|  |  | Autoimmune |  |
|  |  | Uterine abnormalities |  |
|  |  | Implantation disorders |  |
| Endocrine | Glandular hyper- and hypofunction |  |  |

As mentioned above, these diseases, disorders or conditions are merely illustrative of the range of benefits provided by the compounds identified by the methods of the present invention. Accordingly, this invention generally provides therapeutic or prophylactic treatment of the consequences of mechanical trauma or of human diseases. Therapeutic or prophylactic treatment for diseases, disorders or conditions of the CNS and/or peripheral nervous system are contemplated. Therapeutic or prophylactic treatment for diseases, disorders or conditions which have a psychiatric component is provided. Therapeutic or prophylactic treatment for diseases, disorders or conditions including but not limited to those having an ophthalmic, cardiovascular, cardiopulmonary, respiratory, kidney, urinary, reproductive, gastrointestinal, endocrine, or metabolic component is provided.

In one embodiment, such a pharmaceutical composition of erythropoietin or tissue protective cytokine may be administered systemically to protect or enhance the target cells, tissue or organ. Such administration may be parenterally, via inhalation, or transmucosally, e.g., orally, nasally, rectally, intravaginally, sublingually, submucosally or transdermally. Preferably, administration is parenteral, e.g., via intravenous or intraperitoneal injection, and also including, but is not limited to, intra-arterial, intramuscular, intradermal and subcutaneous administration.

Selection of the preferred effective dose will be readily determinable by a skilled artisan based upon considering several factors, which will be known to one of ordinary skill in the art. Such factors include the particular form of erythropoietin and/or compounds identified by the methods of the present invention, and the pharmacokinetic parameters such as bioavailability, metabolism, half-life, etc., which will have been established during the usual development procedures typically employed in obtaining regulatory approval for a pharmaceutical compound. Further factors in considering the dose include the condition or disease to be treated or the benefit to be achieved in a normal individual, the body mass of the patient, the route of administration, whether administration is acute or chronic, concomitant medications, and other factors well known to affect the efficacy of administered pharmaceutical agents. Thus the precise dosage should be decided according to the judgment of the practitioner and each patient's circumstances, e.g., depending upon the condition and the immune status of the individual patient, and according to standard clinical techniques.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

6. EXAMPLES

6.1 Example 1

Competitive EPO Bioassay

The competitive binding assay described below was performed to determine if carbamylated EPO binds to the EPO-R. UT-7 cells which express EPO-R were utilized to determine if carbamylated EPO competitively inhibits binding of rhEPO to the EPO-R. With binding of rhEPO to the EPO-R, cells exhibited proliferation. Inhibition of the proliferation is indicative of competitive binding.

Methods

For the purpose of the competitive binding assay, erythroleukemic UT-7 cells (Komatsu, N. et al., 1991, Cancer Res., 51:341-8) were obtained from DSMZ (Braunschweig, Germany, ACC137). The assays of the carbamylated EPO and rhEPO were performed as described in Leveque et al. (1996, Hematol Oncol 14:137-46) over 48 hours. A WST-1 reduction (Roche #1 644 807) was used to quantitative the living cells. Signal to noise ratio of the assay was 8-15, and the half-maximal effective concentration of carbamylated EPO and rhEPO determined by a four parameter fit from concentration response curves using at least 6 drug concentrations. In this particular assay, the assays was performed with rhEPO, then separately with carbamylated EPO, and then the assay was performed with both rhEPO and carbamylated EPO.

The results show that cell proliferation was 0.6-fold and 1.7-fold greater, respectively, when rhEPO was administered as well as when carbamylated EPO and rhEPO were both incorporated into the assay. Carbamylated EPO alone, demonstrated no effect on cell proliferation even with increased amounts of test compound.

Figure 1:
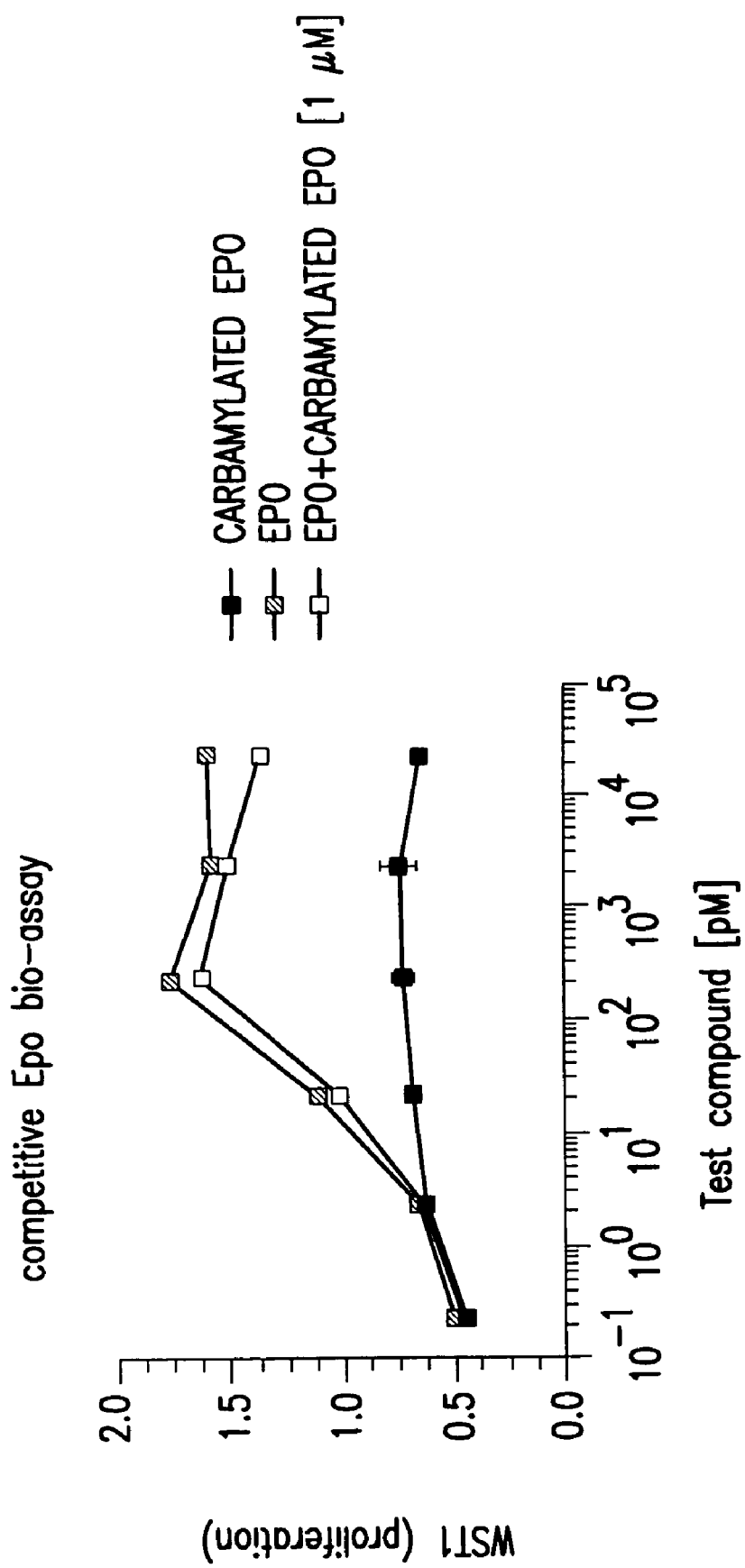
FIG. 1 depicts the results of a competitive assay between EPO and carbamylated EPO that demonstrate that carbamylated EPO does not bind to the EPO-R.

FIG. 1 shows the concentration of the test compound (rhEPO and carbamylated EPO) on the x-axis, plotted against cell proliferation on the y-axis. FIG. 1 clearly shows that the presence of carbamylated EPO does not impact rhEPO's ability to stimulate the proliferation of UT-7 cells within the assay, since the competitive assay with both carbamylated EPO and rhEPO did not exhibit a decrease in cell proliferation.

These results suggests that the carbamylated EPO does not bind with the classical EPO-R dimer complex present on UT-7 cells.

6.2 Example 2

Western Blot of Rat Brain Membrane

Rat brain cells have been shown to be responsive to EPO. Membrane proteins of rat brain cells were isolated to determine if these EPO responsive cells comprise either the $\beta_c$ receptor or the $\beta_c$ receptor associated with IL-3 specific receptor component.

Methods

Rat membrane proteins were isolated using the following protocol. Rat brain was homogenized in PBS containing protease inhibitors (25 µg/ml Leupeptin (5 mg/ml in stock), 10 µg/ml Aprotin (1 mg/ml in stock), 1 mM PMSF (100 mM in stock) 20×. The homogenized tissue was then centrifuged at 3,800 rpm for 5 minutes at 4° C. The supernatant is then collected and further centrifuged at 14,000 rpm for 30 minutes at 4° C. The pellet resulting from is centrifugation is then homogenized in PBS containing the protease inhibitor and 1% Triton X-100. This homogenate is then further centrifuged at 14,000 rpm for 30 minutes at 4° C. The resulting supernatant contains the membrane proteins.

The membrane proteins were then separated by gel electrophoresis. The membrane proteins were blocked overnight with 1× casein (Vector 10× Casein Soln., Cat#: SP-5020) at 4° C. Using a Vector Avidin/Biotin Blocking Kit (Cat #: SP-2001) avidin and biotin blocks were generated. An avidin block is generated by adding 2 drops of avidin per 10 ml 1×PBS-0.1% Tween-20/1× Casein for 20 mins, rinsing the block briefly, and then washing the block with 1×PBS-0.1% Tween-20/1× Casein for 10 mins. A biotin block was generated in a similar manner, by adding 2 drops of biotin per 10 ml 1×PBS-0.1% Tween-20/1× Casein for 20 mins, rinsing the block briefly, and then washing the block with 1×PBS-0.1% Tween-20/1× Casein for 10 mins. The primary antibody (Common β Unit K-17 (Santa Cruz Biotechnology, Inc., Santa Cruz, Calif.), dilution 1:200) was incubated for 1 hour at room temperature. The blocks were then washed four times for 10 minutes each with 1×PBS-0.1% Tween-20/1× Casein. A secondary incubation from the VECTASTAIN ABC kit (Peroxidase Rabbit IgG, Cat#: PK-4001) at a 1:1000 dilution (1 drop in 60 ml 1×PBS-0.1% Tween-20/1× Casein) was performed for 1 hour at room temperature. The block was then washed 3 times for 10 mins each with 1×PBS-0.1% Tween-20. During the wash the AB reagent was prepared in 1×PBS-0.1% Tween-20: 2 drops of reagent A of the kit into 10 ml 1×PBS-0.1% Tween-20, mix well, 2 drops of reagent B, mix well, and incubate for 30 minutes at room temperature to allow complex formation. The membranes were then incubated for 30 minutes at room temperature, then washed 3 times for 10 minutes each with 1×PBS-0.1% Tween-20. The substrate solution from the Vector Peroxidase Substrate Kit DAB in distilled water was prepared (2 drops of Buffer Stock Solution added to 10 ml distilled water, mixed, 4 drops DAB Stock Solution, mixed, 2 drops of Hydrogen Peroxide Solution, mixed) just prior to adding to the blots. The blot with the substrate was then incubated at room temperature for 10 minutes or until the color developed. The blots were then washed with 2 changes of distilled water. This procedure was also repeated using a primary antibody for the IL-3 specific subunit (T-20, Santa Cruz Biotechnology, Inc., Santa Cruz, Calif.).

The results indicated that both the $\beta_c$ receptor and $\beta_c$ receptor specific to IL-3 were identified in rat brain cell membranes.

Figure 2:
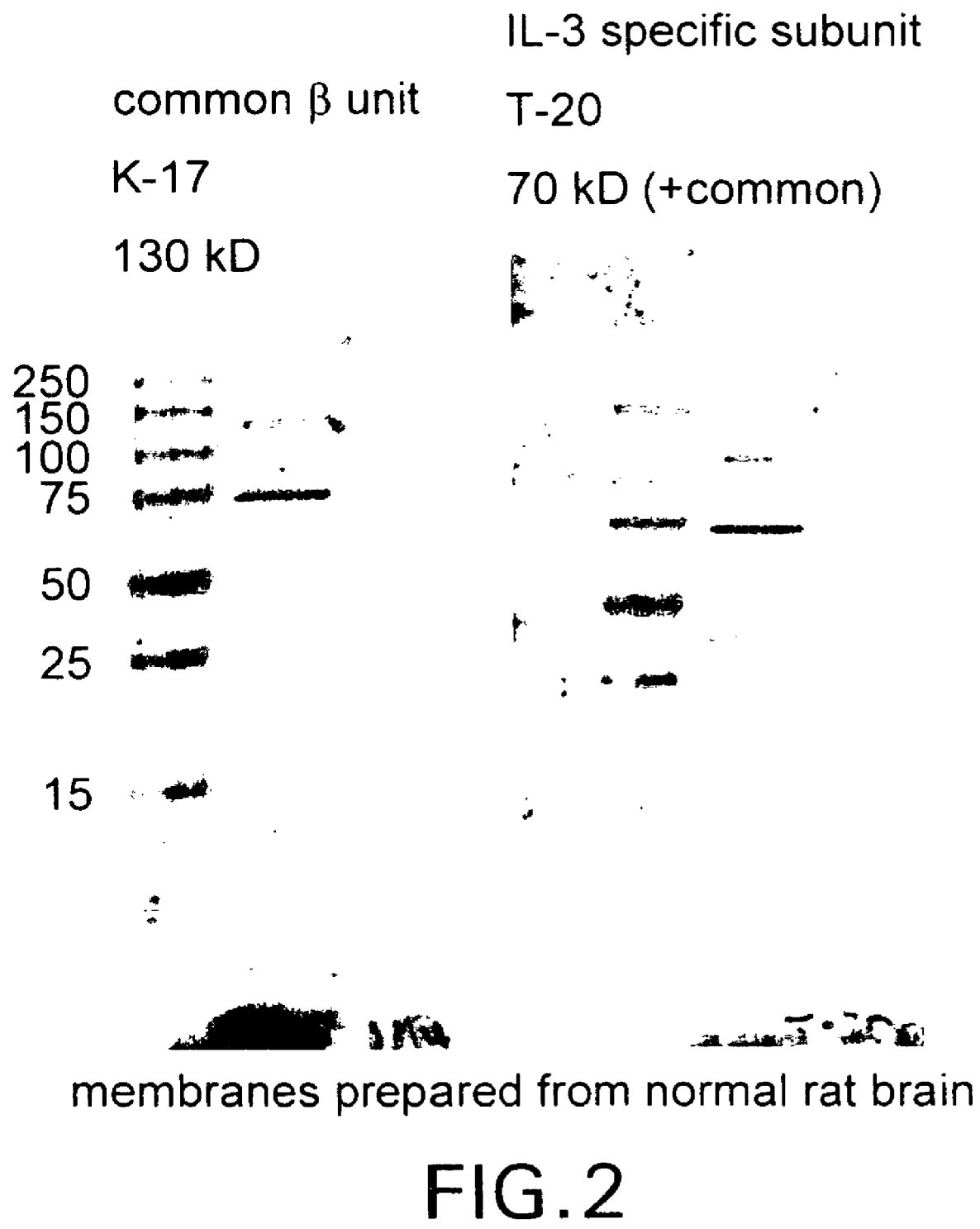
FIG. 2 shows the presence of the $β_c$ receptor within rat brain membranes.

FIG. 2 shows photographs of polyacrylamide gels of the separated membrane proteins. The first gel shows a 130 KD protein that corresponds to the $\beta_c$ receptor. The second gel shows a 70 KD protein that corresponds to the form of the $\beta_c$ receptor specific to IL-3 receptor protein. The results clearly demonstrate the presence of the $\beta_c$ receptor (band at 130 kD) in an erythropoietin-responsive cell (brain). This finding suggests that a tissue protective cytokine receptor complex may form in brain cell membranes, since both EPO receptors and $\beta_c$ receptors are present in the membranes.

6.3 Example 3

Immunohistochemistry for $B_C$ Receptor in Rat Spinal Cord

A rat spinal cord section was stained in order to test for the presence of $\beta_c$ receptors.

Methods

The spinal cord of a rat was removed and fixed in paraffin. The embedded tissue was then sectioned (6 um). The section of spinal cord was then stained using anti-$\beta_c$ receptor antibody (K-17, Santa Cruz Biotechnology, Inc., Santa Cruz, Calif.

Figure 3:
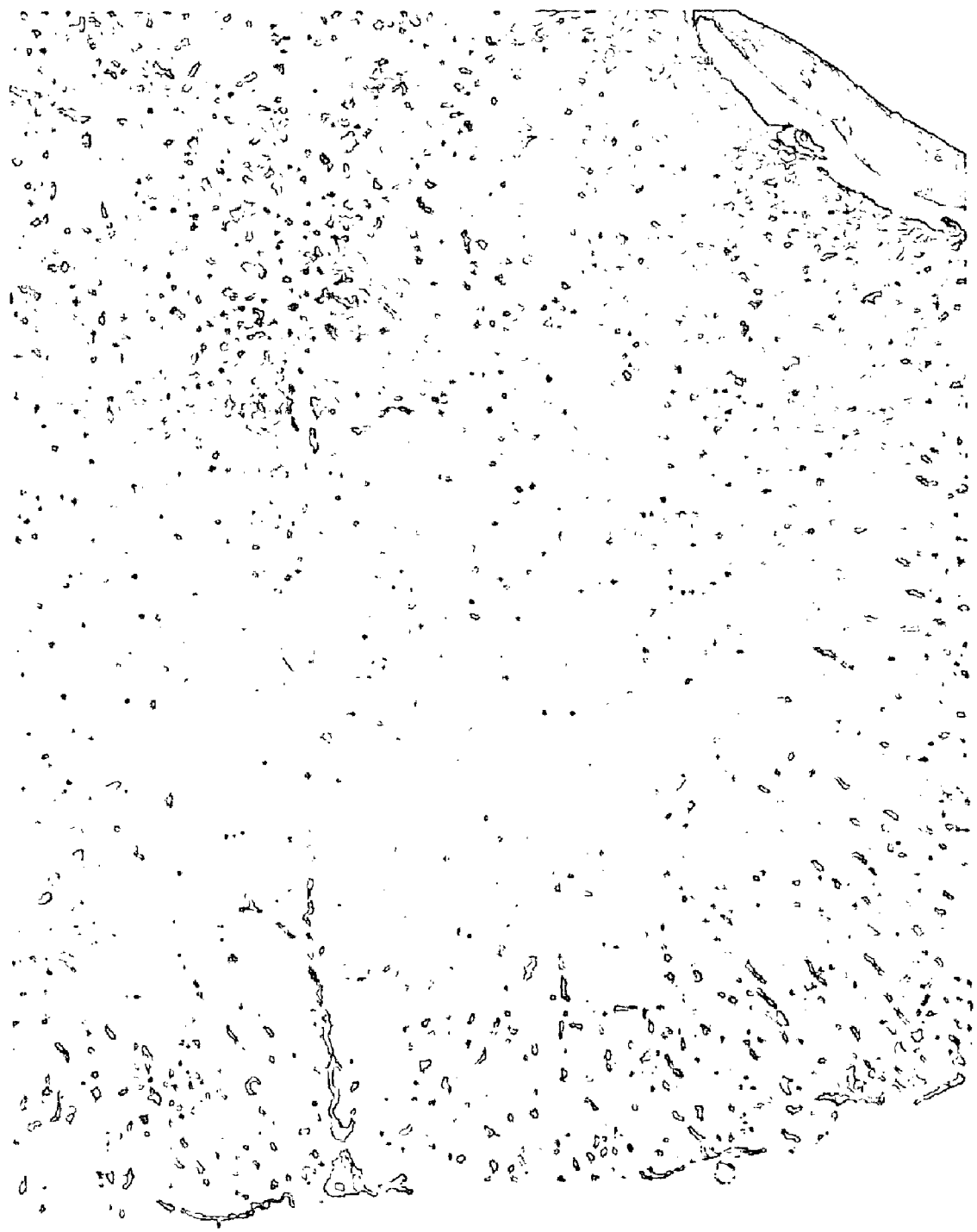
FIG. 3 shows rat spinal cord tissue stained for the presence of the $β_c$ receptor.

FIG. 3 shows a photograph the sectioned spinal cord stained for $\beta_c$ receptor using anti $\beta_c$ receptor antibody. The stain indicates the $\beta_c$ receptor is present within the spinal cord.

Figure 4:
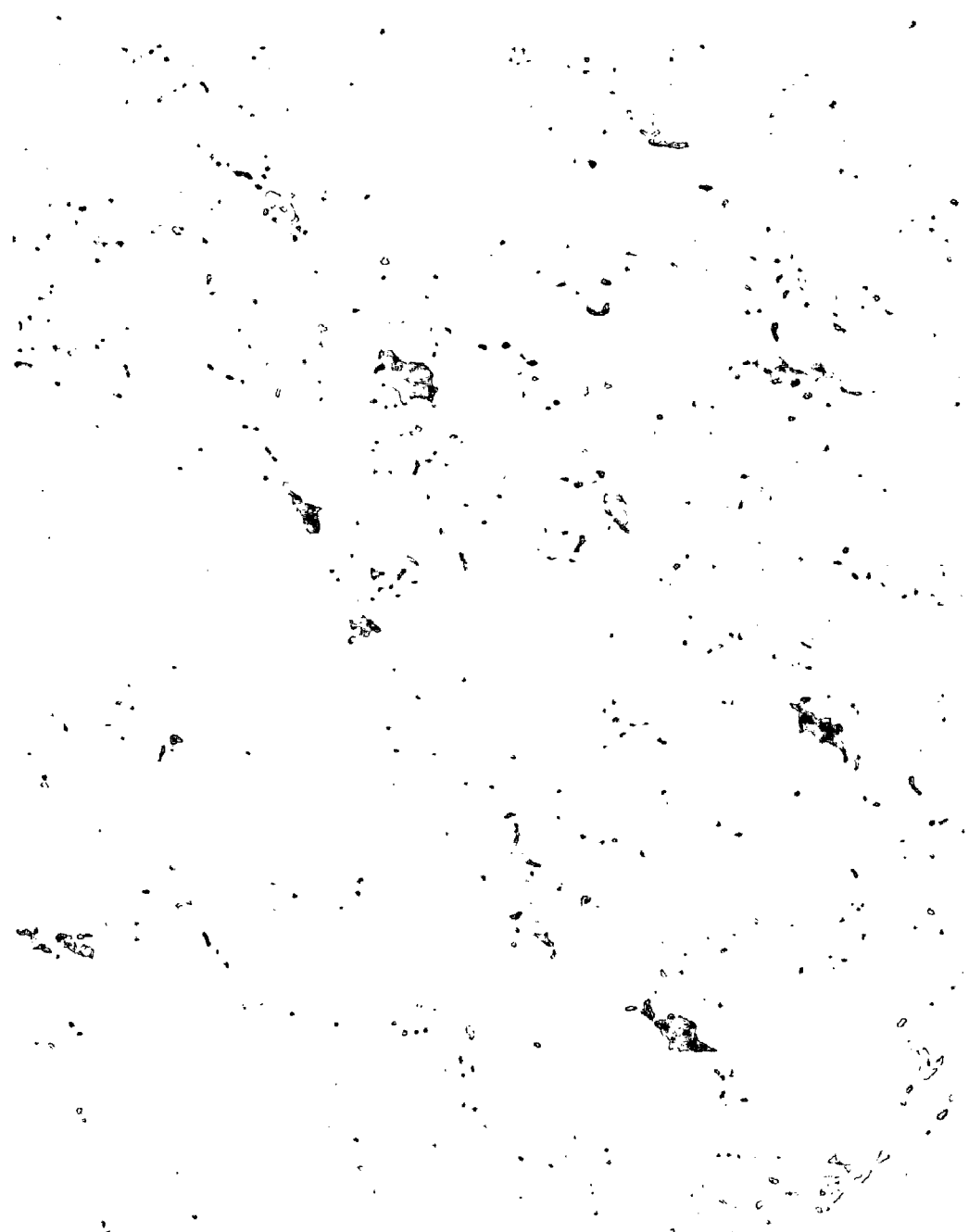
FIG. 4 shows enhanced view of rat spinal cord tissue stained for the presence of the $β_c$ receptor.

FIG. 4 shows a photograph of a close up of the stained areas of the sectioned spinal cord demonstrating reactivity with the anti-$\beta_c$ receptor antibody.

This finding suggests the presence of tissue protective cytokine receptor complexes in spinal cord tissue, since $\beta_c$ receptors and EPO receptors are present in these tissues.

6.4 Example 4

Coprecipitation of EPO-R and $B_C$ Receptor

To determine if EPO receptor and $\beta_c$ receptor are associated with one another in cells, receptor antibodies were used to coprecipitate complexes from cells that express both receptors. Membrane proteins from P-19 cells were separated by electrophoresis on polyacrylamide gels and Western blots were performed to stain for EPO receptor and $\beta_c$ receptor.

Methods

The immunoprecipitation of the EPO-R and $\beta_c$ receptor from P-19 cells, neural-like embryonal carcinoma cells, was performed in accordance with the protocol outlined in Jubinsky et al., 1997, (Blood 90:1867-1873). Using the antibodies specific to the receptor as described above in section 6.3. Immunoprecipitates were then run on a polyacrylymide gel and transferred by Western and stained using antibodies specific for EPO receptors and $\beta_c$ receptors.

Figure 5:
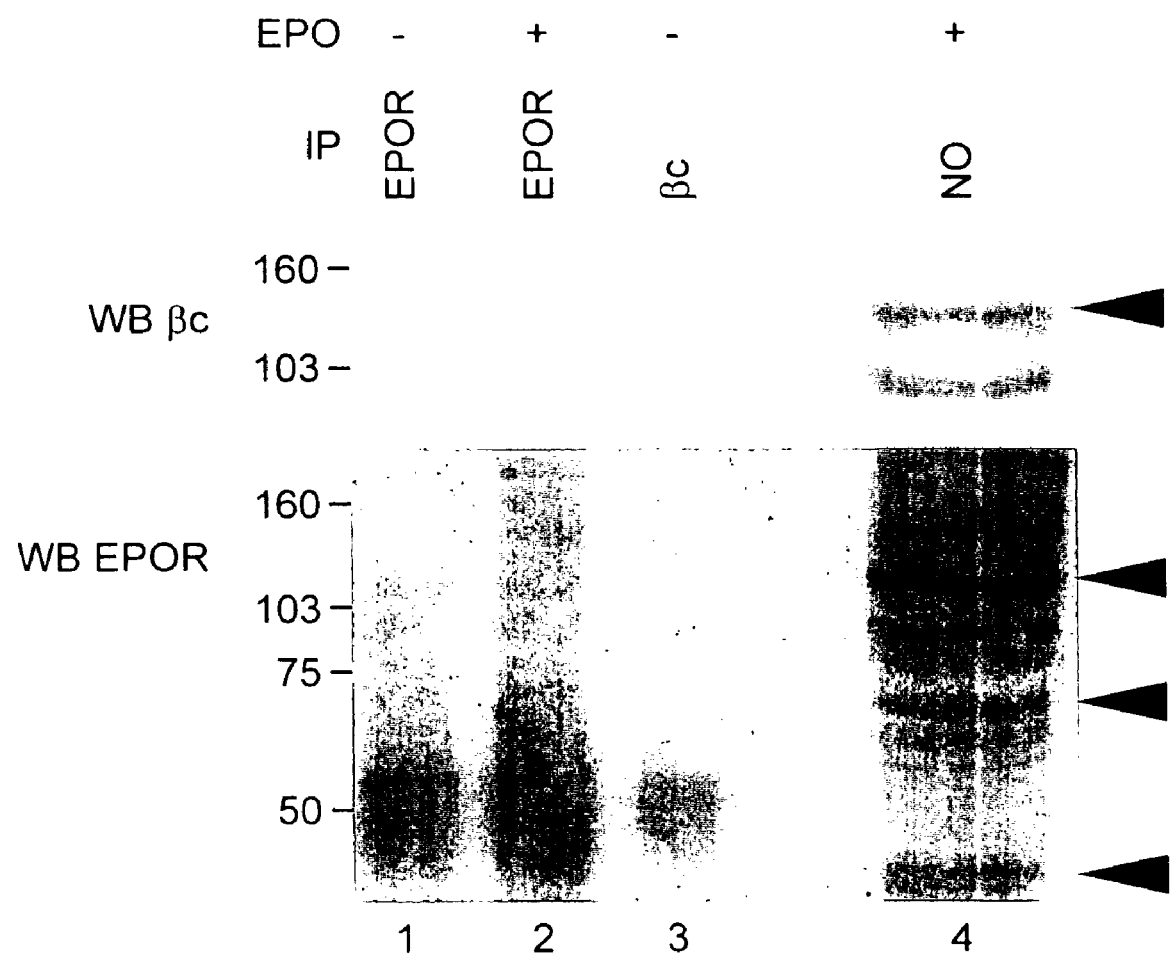
FIG. 5 shows the coprecipitation of the EPO-R and $β_c$ receptor.

FIG. 5 depicts a Western blot of the samples coimmunoprecipitated with the EPO-R and $\beta_c$ receptor antibodies. Lane 1 shows the results of immunoprecipitation of the EPO-R in the absence of EPO on a western blot with the $\beta_c$ receptor antibody (top) and the EPO-R antibody (bottom). A band representing the $\beta_c$ receptor can clearly be seen on the gel (arrow pointing to appropriate band, top). The arrow on the top gel, stained with $\beta_c$ receptor antibody, indicates the position where EPO receptor migrate if it were present in the sample. Lane 2 shows the results of immunoprecipitation of the EPO-R in the presence of EPO on a western blot with the $\beta_C$ receptor antibody (top) and the EPO-R antibody (bottom).

Lane 3 shows reverse immunoprecipitation, the band (bottom) indicates the presence of EPO-R in the sample immunoprecipitated using the $\beta_c$ receptor antibody. The first arrow on the bottom gel, stained with EPO-R antibody, points to a band at about 103 kD that was identified as nucleolin (see Example 10, below). The second arrow on the bottom gel, stained with EPO-R antibody, points to a band at about 68 kD that was identified as EPO receptor (see Example 10, below).

The results suggest that EPO-R and $\beta_c$ receptor form a complex in cells where both receptors are expressed. Finally, complexes were formed whether or not EPO itself was present (compare Lane 1 to Lane 2), suggesting that EPO is not necessary for formation of a tissue protective cytokine receptor complex.

6.5 Example 5

Apoptosis in Cardiomyocytes with and without $\beta_c$ Receptor

Apoptosis in cardiomyocytes was induced in wild type cardiomyocytes from normal mice and in cardiomyocytes from $\beta_c$ chain knockout (−/−) mice to determine if $\beta_c$ receptors played a role in the protective activity of EPO on cells in preventing or delaying apoptosis.

Methods

Cardiomyocytes were isolated from either wild type C57BL/6-129Sv or strain matched common beta chain knockout $\beta_c$ (−/−) mice (Robb et al., 1995, P.N.A.S. U.S.A. 92:9565-9569) as described (Fiordaliso et al., 2001, Diabetes 50:2363-2375). Apoptotic cell death was induced by incubating in staurosporine (Sigma, 0.1 µM) in the presence or absence of erythropoietin (100 ng/ml). Wild type and $\beta_c$ (−/−) cardiomyocyte cells served as controls (Columns 1 and 2 of FIG. 7) where apoptosis was not induced. Apoptosis was induced in wild type and $\beta_c$ (−/−) cardiomyocyte cells (Columns 3 and 4 of FIG. 7), wild type cardiomyocyte cells in the presence of EPO or carbamylated EPO (Columns 5 and 6 of FIG. 7), and $\beta_c$ (−/−) cardiomyocyte cells in the presence of EPO (Column 7 of FIG. 7).

Following 16 hours incubation, cells were fixed and processed for in situ detection of fragmented DNA using TUNEL (Roche Diagnostics).

Figure 7:
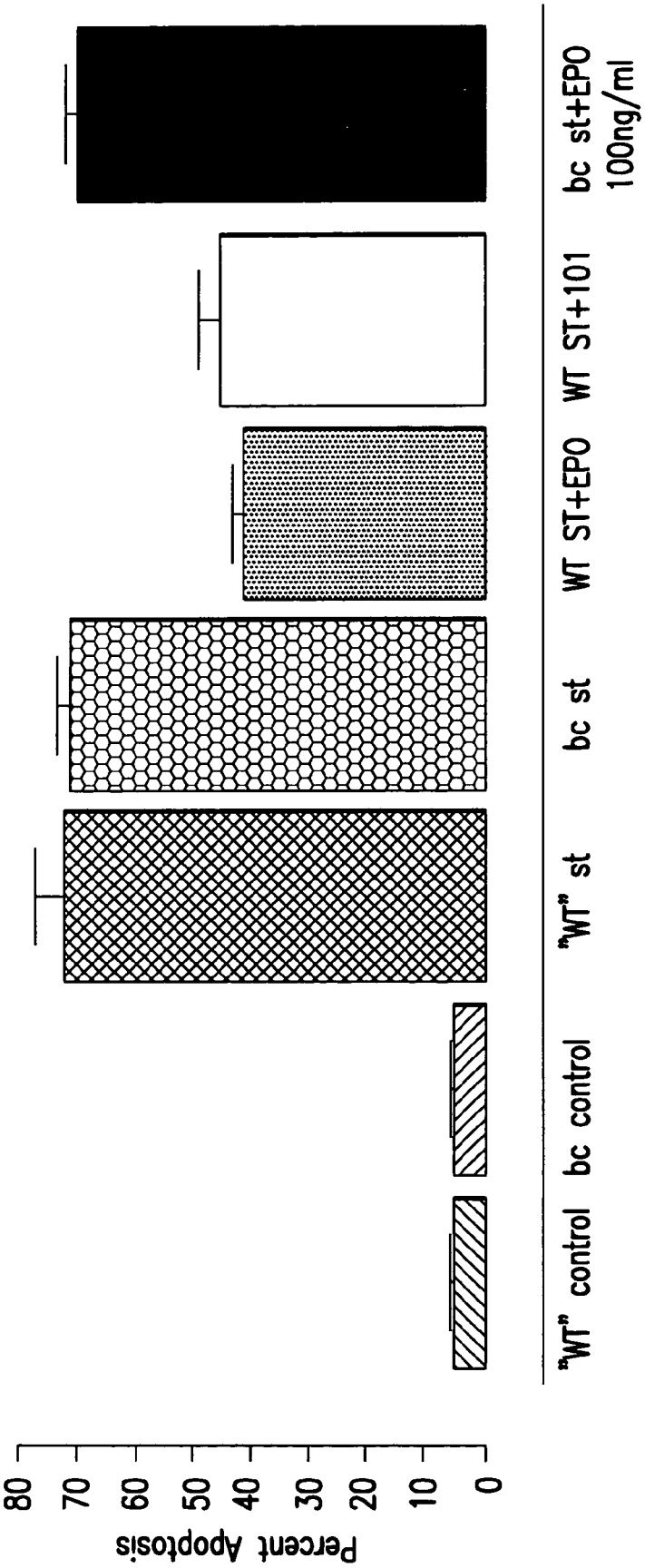
FIG. 7 shows apoptosis in isolated cardiomyocytes from normal and $β_c$ receptor knockout mice in the presence and absence of EPO.

The results are shown in FIG. 7, which shows the percent apoptosis (y-axis) in isolated cardiomyocytes from normal and $\beta_c$ receptor knockout mice in the presence and absence of EPO (Columns 3-7). The percent apoptosis for $\beta_c$(−/−) cardiomyocyte cells where apoptosis was induced in the presence of EPO (Column 7) did not significantly differ from the percent apoptosis in wild type and $\beta_c$ (−/−) cardiomyocyte cells in the absence of EPO (see Columns 3 and 4).

The results suggest that the tissue protective activity of EPO is dependent on the presence of a $\beta_c$ receptor in these cells.

6.6 Example 6

Downstream Kinase Activation via the EPO Receptor

To determine if EPO and carbamylated EPO of varying concentrations were capable of inducing downstream kinase activity in cells expressing the EPO receptor, EPO receptor expressing cells were examined for the presence of an activated kinase, phosphorylated Jak2, in the presence of EPO and carbamylated EPO.

Methods

BaF/3/EPOR cells were stimulated for 10 min. with EPO or carbamylated EPO at different concentrations. Activation of Jak2 was analyzed by Western blotting of cell lysates using an antibody recognizing tyrosine-phosphorylated Jak2 (PY-Jak2). Membranes were stripped and reprobed with an antibody against Jak2 to confirm equal loading.

FIG. 8 shows Western blots of the cell proteins separated by polyacrylamide gel electrophoresis and stained using PY-Jak2 antibodies. The top shows that phosphorylated Jak2 was present in cells stimulated with EPO at 5 nM and 50 nM concentrations.

The results suggest that carbamylated EPO cannot induce downstream activation of the classical EPO receptor homodimer in cells expressing the EPO receptor. This suggests carbamylated EPO does not bind to the classical EPO receptor homodimer.

6.7 Example 7

BAF3/EPOR Cell-Binding Assay

To determine if cells expressing the EPO receptor bind EPO and carbamylated EPO, BaF3 cells were contacted with each ligand and binding affinity was measured in a competitive binding assay.

Methods 0.1 nM 125-I EPO and graded doses of unlabelled EPO and carbamylated EPO, respectively were incubated 30 min at RT in PBS in 106 wells. The membranes were washed on filters and counted for membrane bound 125-I EPO in a gammacounter. The receptor bound fraction of radioligand was plotted as bound 125-I EPO against graded doses of unlabelled ligand.

FIG. 9 shows a graph of ligand binding affinity for BaF3 cells expressing the EPO receptor. Ligand concentration in nM (x-axis) is plotted against binding (cpm) (y-axis) for BaF3 EPO receptor expressing cells contacted with EPO receptor ligands EPO and carbamylated EPO.

The BaF-3/EPO-R cells bind EPO with an affinity of about 1 nM, whereas no carbamylated EPO binding was detectable. The results indicate that carbamylated EPO does not competitively inhibit binding of EPO to cells expressing the EPO receptor.

6.8 Example 8

UT-7 Membrane Assay

To determine if cells expressing the classical EPO receptor dimer bind EPO and carbamylated EPO, UT-7 cell membranes were contacted with each ligand and binding affinity was measured in a competitive binding assay.

Methods

One hundred micrograms of UT-7 membranes were incubated 30 min at room temperature in 200 ul PBS with 0.1 nM $^{125}$I EPO and graded doses of unlabelled EPO and carbamylated EPO, respectively. The membranes were washed on filters and counted for membrane bound $^{125}$I EPO in a gammacounter. The receptor-bound fraction of radioligand was plotted as bound $^{125}$I EPO against graded doses of unlabelled ligand. The UT-7 membranes bind EPO with an affinity of 0.1-0.5 nM. In contrast, no carbamylated EPO binding was detected.

FIG. 10 shows a graph of ligand binding affinity for UT-7 cell membranes having the EPO receptor. Ligand concentration in nM (x-axis) is plotted against binding (cpm) (y-axis) for UT-7 EPO receptor expressing cell membranes contacted with EPO receptor ligands EPO and carbamylated EPO.

The results indicate that carbamylated EPO does not competitively inhibit binding of EPO to cells expressing both the classical EPO receptor dimer.

6.9 Example 9

Hemotocrit and Hemoglobulin Concentrations

Mice were administered EPO and modified EPO to determine whether carbamylated EPO or asialoEPO have the same erythropoietic capabilities, i.e., increased hematocrit and increased hemoglobin, as EPO.

Methods

Mice were injected intravenously 5 times per week with 50 µg/kg of EPO, carbamylated EPO and asialoEPO for 4 weeks. Serum hemoglobin concentrations and the hematocrite were determined by a hemoglobinometer using blood (<50 µl) withdrawn from the retroorbital plexus under isoflurane anesthesia.

FIG. 11 shows histograms of 11A, hematocrit levels as measured by the percent volume of hematocrit (y-axis), and 11B, hemoglobin levels measured in concentration in mM (y-axis), in mice after administration of control (vehicle), EPO, carbamylated EPO, and asialoEPO (x-axis).

The results indicate that carbamylated EPO and asialoEPO administered to mice do not induce the increased hematocrit and hemoglobin exhibited by mice which were administered EPO. This suggests that carbamylated EPO and asialoEPO interact differently with cells in vivo in comparison to EPO. When combined with the experimental results of the above binding assays, these results confirm that carbamylated EPO and asialoEPO do not bind the EPO receptor and therefore cannot impart the erythropoietic activities of EPO.

6.10 Example 10

Detecting the Presence of Nucleolin

The precipitation using Western blot and the $\beta_c$ receptor antibody described in Example 4 above was further analyzed. In particular, the protein corresponding to the 103 KD band shown in FIG. 5 five Lane 1 (top) further analyzed to determine the identity of another protein that had precipitated in the samples.

Methods

P19 cells were grown to 70% confluence in complete medium. They were treated with 10 ng/ml EPO or saline (C) for 15 min, then detached by tapping on the flask, spun for 7 min at 700 rpm and resuspended in lysis buffer (TBS with protease inhibitors, 2 mM CaCl, 1% Triton and 1% NP40) to give a final concentration of 1 mg protein/ml. CaCl was present in the lysis buffer, and freezing or vortexing were avoided, to maintain protein interactions.

After removal of debris by centrifugation for 10 min at 120000 rpm, the lysate was incubated with protein A sepharose (Pharmacia, 10 microL drained gel/ml) for 1 h at room temperature to remove non specific binding.

The supernatant was then incubated with protein A Sepharose (10 microL gel/ml) previously coupled to the antibody for 1 h and washed three times with lysis buffer. Either an antibody against beta common chain (K17, Santa Cruz Biotechnologies*) or a mixture of two antibodies against EPO-R (M20 and h194, Santa Cruz Biotechnologies) at a final dilution of 1:200 were used and the incubation was run overnight at 4° C. Protein A sepharose beads were then washed five times with low detergent lysis buffer (the same as above, except 0.5% Triton and no NP40) and bound proteins were dissociated by the addition of 30 microL of 2× Laemmli sample buffer with 5% beta-mercaptoethanol and run on a 10% SDS-PAGE.

The 103 kD band was excised from Coomassie blue stained gel, destained for few hours in 25 mM ammonium bicarbonate/40% ethanol and washed with a sequential increasing percentage of acetonitrile. Proteins were in gel-digested overnight at 30° C. with trypsin (Promega, Madison Wis.) at a concentration of 12 ng/ml in a 25 mM ammonium bicarbonate/10% acetonitrile solution. Peptide mass fingerprinting (PMF) was performed on a Bruker ReflexIII™ matrix-assisted laser desorption/ionization (MALDI) mass spectrometer using a-cyano-4-hydroxycinnamic acid (Bruker Daltonics Billerica, Mass.) as a matrix. The mass spectra were externally calibrated with a mixture of 7 standard peptides in the range between 1000 to 3000 Da. Data generated were subjected to database (NCBInr) searching using as programs Mascot and Profound allowing up to 1 missed trypsin cleavage and a mass tolerance of ±0.2 Da. Mass spectrometry was used to determine the identity of nucleolin.

The results suggest that the P19 cells expressing the EPO receptor and the $\beta_c$ receptor that form a tissue protective cytokine receptor complex produce nucleolin in response to administration of EPO.

FIG. 12 shows a photograph of the SDS-PAGE gel with a 103 KD nucleolin protein circled.

The invention is not to be limited in scope by the specific embodiments described which are intended as single illustrations of individual aspects of the invention, and functionally equivalent methods and components are within the scope of the invention. Indeed various modifications of the invention, in addition to those shown and described herein will become apparent to those skilled in the art from the foregoing description and accompanying drawings. Such modifications are intended to fall within the scope of the appended claims.

All references cited herein are incorporated by reference herein in their entireties for all purposes.

What is claimed:

1. A method for identifying a compound that modulates a tissue protective activity, comprising:
   (a) contacting a test compound with a tissue protective cytokine receptor complex-expressing cell, wherein said tissue protective cytokine receptor complex comprises an erythropoietin (EPO) receptor and a βc receptor and wherein said cell is transformed with a nucleic acid comprising a nucleotide sequence that encodes a reporter gene operably linked to a regulatory element associated with a tissue protective cytokine receptor complex activity;
   (b) identifying a test compound that increases the level of reporter gene expression relative to the level of reporter gene expression measured in the absence of the test compound, and
   (c) assaying the identified test compound for the ability to inhibit apoptosis,
wherein a test compound that increases the level of reporter gene expression relative to the level of reporter gene expression in the absence of the test compound and inhibits apoptosis is identified as a compound that modulates a tissue protective activity.

2. The method of claim 1, wherein the regulatory element is a serum response element.

3. The method of claim 1, wherein the cell is a prokaryotic cell.

4. The method of claim 1, wherein the cell is a eukaryotic cell.

5. The method of claim 4, wherein the eukaryotic cell is a human cell.

6. The method of claim 1, wherein the cell endogenously expresses at least one subunit of the tissue protective cytokine receptor complex.

7. The method of claim 1, wherein the cell is a BaF3 cell.

8. A method of identifying a compound that modulates the activity of a tissue protective cytokine receptor complex comprising an erythropoietin receptor and βc receptor, said method comprising:
   (a) contacting a test compound with a cell of a modified yeast strain (i) containing a nucleotide sequence encoding a reporter gene that is operably linked to a tissue protective cytokine receptor complex-responsive promoter and (ii) expressing a tissue protective cytokine receptor complex comprising an erythropoietin receptor and a βc receptor;
   (b) determining the level of activity of said tissue protective cytokine receptor complex by measuring the level of reporter gene expression; and
   (c) assaying the test compound for the ability to inhibit apoptosis,
such that if the level of reporter gene activity in the presence of the compound increases relative to the level of reporter gene activity in the absence of the compound and if the test compound inhibits apoptosis, then a compound that modulates the activity of said tissue protective cytokine receptor complex is identified.

9. The method of claim 1, further comprises detecting the presence of nucleolin in the cell and wherein an upregulation of nucleolin in the cell indicates a tissue protective activity.

10. The method of claim 1, further comprises detecting or measuring an increased level of activity of neuroglobin or cytoglobin in a cell and wherein an upregulation of neuroglobin or cytoglobin in the cell indicates a tissue protective activity.

11. The method of claim 1 or 8, wherein the test compound is an antibody specific for the tissue protective cytokine receptor complex.

12. The method of claim 1 or 8, wherein the test compound is an antibody specific for a tissue protective cytokine receptor complex ligand.

13. The method of claim 1 or 8, wherein the test compound is a small molecule.

14. The method of claim 1 or 8, wherein the test compound is a peptide.

15. The method of claim 1 or 8, wherein the test compound is a member of a library.

16. The method of claim 12, wherein the tissue protective cytokine receptor complex ligand is an EPO.

17. The method of claim 1 or 8, wherein the compound binds the tissue protective cytokine receptor complex.

18. The method of claim 1 or 8, wherein the tissue protective activity inhibits apoptotic death of a cell, tissue, or organ.

19. The method of claim 1 or 8, wherein the ability to inhibit apoptosis is assayed in a cell-based assay.

20. The method of claim 19, wherein the ability of the test compound to inhibit apoptosis is assayed in a cell isolated from an animal's tissues or organs.

21. The method of claim 20, wherein the cell is a cardiomyocyte cell.

22. The method of claim 20, wherein the cell is a neuronal, retinal, muscle, heart, lung, liver, kidney, small intestine, adrenal cortex, adrenal medulla, capillary endothelial, testes, ovary, pancreas, bone, skin, or endometrial cell.

23. The method of claim 19, wherein the cell is a neuronal, retinal, muscle, heart, lung, liver, kidney, small intestine, adrenal cortex, adrenal medulla, capillary endothelial, testes, ovary, pancreas, bone, skin, or endometrial cell.

24. The method of claim 19, wherein the cell is a cardiomyocyte cell.

25. The method of claim 1 or 8, further comprising assaying a tissue protective activity in a $\beta_c$ (−/−) knock-out non-human animal.

* * * * *

SEQUENCE LISTING

<160> NUMBER OF SEQ ID NOS: 212

<210> SEQ ID NO 1
<211> LENGTH: 5
<212> TYPE: PRT
<213> ORGANISM: Homo sapiens

```
<400> SEQUENCE: 1

Val Leu Gln Arg Tyr
1               5

<210> SEQ ID NO 2
<211> LENGTH: 8
<212> TYPE: PRT
<213> ORGANISM: Homo sapiens

<400> SEQUENCE: 2

Thr Lys Val Asn Phe Tyr Ala Trp
1               5

<210> SEQ ID NO 3
<211> LENGTH: 9
<212> TYPE: PRT
<213> ORGANISM: Homo sapiens

<400> SEQUENCE: 3

Ser Gly Leu Arg Ser Leu Thr Thr Leu
1               5

<210> SEQ ID NO 4
<211> LENGTH: 6
<212> TYPE: PRT
<213> ORGANISM: Homo sapiens

<400> SEQUENCE: 4

Ser Asn Phe Leu Arg Gly
1               5

<210> SEQ ID NO 5
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 5

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Glu Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160
```

Thr Ala Asp Thr Phe Arg Lys Leu Phe Arg Val Tyr Ser Asn Phe Leu
            165                 170                 175

Arg Gly Lys Leu Lys Leu Tyr Thr Gly Glu Ala Cys Arg Thr Gly Asp
        180                 185                 190

Arg

<210> SEQ ID NO 6
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 6

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Asp Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 7
<211> LENGTH: 580
<212> TYPE: DNA
<213> ORGANISM: Homo sapiens

<400> SEQUENCE: 7
atgggggtgc acgaatgtcc tgcctggctg tggcttctcc tgtccctgct gtcgctccct    60
ctgggcctcc cagtcctggg cgccccacca cgcctcatct gtgacagccg agtcctggag   120
aggtacctct tggaggccaa ggaggccgag aatatcacga cgggctgtgc tgaacactgc   180
agcttgaatg agaatatcac tgtcccagac accaaagtta atttctatgc ctggaagagg   240
atggaggtcg ggcagcaggc cgtagaagtc tggcagggcc tggccctgct gtcggaagct   300
gtcctgcggg gccaggccct gttggtcaac tcttcccagc cgtgggagcc cctgcactgc   360
atgtggataa agccgtcagt ggccttcgca gcctcaccac tctgcttcgg gctctgggag   420
cccagaagga agccatctcc cctccagatg cggcctcagc tgctccactc cgaacaatca   480

```
ctgctgacac tttcgcaaac tcttccgagt ctactccaat ttcctccggg gaaagctgaa    540
gctgtacaca ggggaggcct gcaggacagg ggacagatga                          580

<210> SEQ ID NO 8
<211> LENGTH: 35
<212> TYPE: DNA
<213> ORGANISM: Artificial
<220> FEATURE:
<223> OTHER INFORMATION: Description of Artificial Sequence: primer

<400> SEQUENCE: 8
agctctcgag gcgcggagat gggggtgcac gaatg                               35

<210> SEQ ID NO 9
<211> LENGTH: 36
<212> TYPE: DNA
<213> ORGANISM: Artificial
<220> FEATURE:
<223> OTHER INFORMATION: Description of Artificial Sequence: primer

<400> SEQUENCE: 9
atgctctaga cacacctggt catctgtccc ctgtcc                              36

<210> SEQ ID NO 10
<211> LENGTH: 193
<212> TYPE: PRT
<213> ORGANISM: Homo sapiens

<400> SEQUENCE: 10
```

Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Arg Leu
                20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

```
<210> SEQ ID NO 11
<211> LENGTH: 45
<212> TYPE: DNA
```

```
<213> ORGANISM: Artificial
<220> FEATURE:
<223> OTHER INFORMATION: Description of Artificial Sequence: primer

<400> SEQUENCE: 11
catgtggata aagccgtcga gggccttcgc agcctcacca ctctg          45

<210> SEQ ID NO 12
<211> LENGTH: 45
<212> TYPE: DNA
<213> ORGANISM: Artificial
<220> FEATURE:
<223> OTHER INFORMATION: Description of Artificial Sequence: primer

<400> SEQUENCE: 12
cagagtggtg aggctgcgaa ggccctcgac ggctttatcc acatg          45

<210> SEQ ID NO 13
<211> LENGTH: 45
<212> TYPE: DNA
<213> ORGANISM: Artificial
<220> FEATURE:
<223> OTHER INFORMATION: Description of Artificial Sequence: primer

<400> SEQUENCE: 13
gagaatatca ctgtcccaga caccgacgtt aatttctatg cctgg          45

<210> SEQ ID NO 14
<211> LENGTH: 45
<212> TYPE: DNA
<213> ORGANISM: Artificial
<220> FEATURE:
<223> OTHER INFORMATION: Description of Artificial Sequence: primer

<400> SEQUENCE: 14
ccaggcatag aaattaacgt cggtgtctgg gacagtgata ttctc          45

<210> SEQ ID NO 15
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 15

Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Pro Arg Leu
            20                  25                  30

Ala Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
```

```
                130                 135                 140
Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
                180                 185                 190

Arg

<210> SEQ ID NO 16
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 16

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
                20                  25                  30

Ile Ala Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
        50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Val Ser Gly
            115                 120                 125

Leu Arg Ser Leu Thr Thr Leu Leu Arg Ala Leu Gly Ala Gln Lys Glu
        130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
                180                 185                 190

Arg

<210> SEQ ID NO 17
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 17

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
                20                  25                  30

Ile Cys Asp Ser Ile Val Leu Glu Arg Tyr Leu Leu Glu Ala Lys Glu
            35                  40                  45
```

```
Ala Glu Asn Ile Thr Thr Gly Cys Ala Glu His Cys Ser Leu Asn Glu
     50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Val Ser Gly
            115                 120                 125

Leu Arg Ser Leu Thr Thr Leu Leu Arg Ala Leu Gly Ala Gln Lys Glu
            130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 18
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 18

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
                20                  25                  30

Ile Cys Asp Ser Arg Ser Leu Glu Arg Tyr Leu Leu Glu Ala Lys Glu
            35                  40                  45

Ala Glu Asn Ile Thr Thr Gly Cys Ala Glu His Cys Ser Leu Asn Glu
     50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Val Ser Gly
            115                 120                 125

Leu Arg Ser Leu Thr Thr Leu Leu Arg Ala Leu Gly Ala Gln Lys Glu
            130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg
```

```
<210> SEQ ID NO 19
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 19

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Ala Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 20
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 20

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Ala Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
```

```
                115             120                 125
Leu Arg Ser Leu Thr Thr Leu Leu Arg Ala Leu Gly Ala Gln Lys Glu
        130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 21
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 21

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Ala Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 22
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 22

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30
```

```
Ile Cys Asp Ser Arg Val Leu Glu Arg Tyr Leu Leu Glu Ala Lys Glu
         35                  40                  45

Ala Glu Asn Ile Thr Thr Gly Cys Ala Glu His Cys Ser Leu Asn Glu
 50                  55                  60

Asn Ile Thr Val Pro Asp Thr Lys Val Asn Phe Tyr Ala Trp Lys Arg
 65                  70                  75                  80

Met Glu Val Gly Gln Gln Ala Val Glu Val Trp Gln Gly Leu Ala Leu
                 85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
            115                 120                 125

Leu Arg Ser Leu Thr Thr Leu Leu Arg Ala Leu Gly Ala Gln Lys Glu
130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 23
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 23

Met Gly Val His Glu Cys Pro Ala Trp Leu Trp Leu Leu Leu Ser Leu
 1               5                  10                  15

Leu Ser Leu Pro Leu Gly Leu Pro Val Leu Gly Ala Pro Pro Arg Leu
             20                  25                  30

Ile Cys Asp Ser Arg Val Leu Glu Glu Tyr Leu Leu Glu Ala Lys Glu
         35                  40                  45

Ala Glu Asn Ile Thr Thr Gly Cys Ala Glu His Cys Ser Leu Asn Glu
 50                  55                  60

Asn Ile Thr Val Pro Asp Thr Lys Val Asn Phe Tyr Ala Trp Lys Arg
 65                  70                  75                  80

Met Glu Val Gly Gln Gln Ala Val Glu Val Trp Gln Gly Leu Ala Leu
                 85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
            115                 120                 125

Leu Arg Ser Leu Thr Thr Leu Leu Arg Ala Leu Gly Ala Gln Lys Glu
130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190
```

Arg

<210> SEQ ID NO 24
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 24

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Gln Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 25
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 25

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Ala Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser

-continued

```
                100                 105                 110
Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 26
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 26

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Phe Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 27
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 27

Met Gly Val His Glu Cys Pro Ala Trp Leu Trp Leu Leu Leu Ser Leu
1               5                   10                  15
```

-continued

```
Leu Ser Leu Pro Leu Gly Leu Pro Val Leu Gly Ala Pro Pro Arg Leu
             20                  25                  30

Ile Cys Asp Ser Arg Val Leu Glu Arg Ile Leu Leu Glu Ala Glu Glu
         35                  40                  45

Ala Glu Asn Ile Thr Thr Gly Cys Ala Glu His Cys Ser Leu Asn Glu
     50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                 85                  90                  95

Leu Ser Glu Ala Val Leu Arg Gly Gln Ala Leu Leu Val Asn Ser Ser
             100                 105                 110

Gln Pro Trp Glu Pro Leu Gln Leu His Val Asp Lys Ala Val Ser Gly
         115                 120                 125

Leu Arg Ser Leu Thr Thr Leu Leu Arg Ala Leu Gly Ala Gln Lys Glu
     130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                 165                 170                 175

Arg Gly Lys Leu Lys Leu Tyr Thr Gly Glu Ala Cys Arg Thr Gly Asp
             180                 185                 190

Arg

<210> SEQ ID NO 28
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 28

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
             20                  25                  30

Ile Cys Asp Ser Arg Val Leu Glu Arg Tyr Leu Leu Glu Ala Glu Glu
         35                  40                  45

Ala Glu Asn Ile Thr Thr Gly Cys Ala Glu His Cys Ser Leu Asn Glu
     50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                 85                  90                  95

Leu Ser Glu Ala Val Leu Arg Gly Gln Ala Leu Leu Val Asn Ser Ser
             100                 105                 110

Gln Pro Trp Glu Pro Leu Gln Leu His Val Asp Lys Ala Val Ser Gly
         115                 120                 125

Leu Arg Ser Leu Thr Thr Leu Leu Arg Ala Leu Gly Ala Gln Lys Glu
     130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                 165                 170                 175
```

```
Arg Gly Lys Leu Lys Leu Tyr Thr Gly Glu Ala Cys Arg Thr Gly Asp
            180                 185                 190

Arg

<210> SEQ ID NO 29
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 29

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Ala Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 30
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 30

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Ala
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
```

```
                    85                  90                  95
Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg
```

<210> SEQ ID NO 31
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 31

```
Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Lys Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg
```

<210> SEQ ID NO 32
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 32

```
Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
            35                  40                  45

Ala Glu Asn Ile Thr Thr Gly Ser Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Val Ser Gly
            115                 120                 125

Leu Arg Ser Leu Thr Thr Leu Leu Arg Ala Leu Gly Ala Gln Lys Glu
130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
                180                 185                 190

Arg

<210> SEQ ID NO 33
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 33

Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
            35                  40                  45

Ala Glu Asn Ile Thr Thr Gly Tyr Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Val Ser Gly
            115                 120                 125

Leu Arg Ser Leu Thr Thr Leu Leu Arg Ala Leu Gly Ala Gln Lys Glu
130                 135                 140

Ala Ile Ser Pro Pro Asp Ala Ala Ser Ala Ala Pro Leu Arg Thr Ile
145                 150                 155                 160
```

-continued

```
Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 34
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 34

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Asn Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 35
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 35

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu Thr Cys Ser Leu Asn Glu
    50                  55                  60

Asn Ile Thr Val Pro Asp Thr Lys Val Asn Phe Tyr Ala Trp Lys Arg
```

```
            65                  70                  75                  80
Met Glu Val Gly Gln Gln Ala Val Glu Val Trp Gln Gly Leu Ala Leu
                    85                  90                  95

Leu Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Val Ser Gly
                115                 120                 125

Leu Arg Ser Leu Thr Thr Leu Leu Arg Ala Leu Gly Ala Gln Lys Glu
            130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                    165                 170                 175

Arg Gly Lys Leu Lys Leu Tyr Thr Gly Glu Ala Cys Arg Thr Gly Asp
                180                 185                 190

Arg
```

<210> SEQ ID NO 36
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 36

```
Met Gly Val His Glu Cys Pro Ala Trp Leu Trp Leu Leu Leu Ser Leu
1                   5                   10                  15

Leu Ser Leu Pro Leu Gly Leu Pro Val Leu Gly Ala Pro Pro Arg Leu
                    20                  25                  30

Ile Cys Asp Ser Arg Val Leu Glu Arg Tyr Leu Leu Glu Ala Lys Glu
                35                  40                  45

Ala Glu Asn Ile Thr Thr Gly Cys Ala Glu His Ser Ser Leu Asn Glu
            50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                    85                  90                  95

Leu Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Val Ser Gly
                115                 120                 125

Leu Arg Ser Leu Thr Thr Leu Leu Arg Ala Leu Gly Ala Gln Lys Glu
            130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                    165                 170                 175

Arg Gly Lys Leu Lys Leu Tyr Thr Gly Glu Ala Cys Arg Thr Gly Asp
                180                 185                 190

Arg
```

<210> SEQ ID NO 37
<211> LENGTH: 193
<212> TYPE: PRT
<213> ORGANISM: Artificial
<220> FEATURE:

<223> OTHER INFORMATION: Description of Artificial Sequence: mutein

<400> SEQUENCE: 37

```
Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Tyr Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg
```

<210> SEQ ID NO 38
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 38

```
Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Lys Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140
```

```
Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
            165                 170                 175

Arg Gly Lys Leu Lys Leu Tyr Thr Gly Glu Ala Cys Arg Thr Gly Asp
            180                 185                 190

Arg

<210> SEQ ID NO 39
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 39

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
                20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
        50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Lys Ser Ser
                100                 105                 110

Gln Pro Trp Glu Pro Leu Gln Leu His Val Asp Lys Ala Val Ser Gly
            115                 120                 125

Leu Arg Ser Leu Thr Thr Leu Leu Arg Ala Leu Gly Ala Gln Lys Glu
130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
            165                 170                 175

Arg Gly Lys Leu Lys Leu Tyr Thr Gly Glu Ala Cys Arg Thr Gly Asp
            180                 185                 190

Arg

<210> SEQ ID NO 40
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 40

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
                20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
```

```
                50                  55                  60
Asn Ile Thr Val Asn Asp Thr Lys Val Asn Phe Tyr Ala Trp Lys Arg
 65                  70                  75                  80

Met Glu Val Gly Gln Gln Ala Val Glu Val Trp Gln Gly Leu Ala Leu
                 85                  90                  95

Leu Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Val Ser Gly
                115                 120                 125

Leu Arg Ser Leu Thr Thr Leu Leu Arg Ala Leu Gly Ala Gln Lys Glu
                130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
                180                 185                 190

Arg

<210> SEQ ID NO 41
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 41

Met Gly Val His Glu Cys Pro Ala Trp Leu Trp Leu Leu Leu Ser Leu
  1               5                  10                  15

Leu Ser Leu Pro Leu Gly Leu Pro Val Leu Gly Ala Pro Pro Arg Leu
                 20                  25                  30

Ile Cys Asp Ser Arg Val Leu Glu Arg Tyr Leu Leu Glu Ala Lys Glu
                 35                  40                  45

Ala Glu Asn Ile Thr Thr Gly Cys Ala Glu His Cys Ser Leu Asn Glu
                 50                  55                  60

Asn Ile Thr Val Ala Asp Thr Lys Val Asn Phe Tyr Ala Trp Lys Arg
 65                  70                  75                  80

Met Glu Val Gly Gln Gln Ala Val Glu Val Trp Gln Gly Leu Ala Leu
                 85                  90                  95

Leu Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Val Ser Gly
                115                 120                 125

Leu Arg Ser Leu Thr Thr Leu Leu Arg Ala Leu Gly Ala Gln Lys Glu
                130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
                180                 185                 190

Arg

<210> SEQ ID NO 42
<211> LENGTH: 193
```

<212> TYPE: PRT
<213> ORGANISM: Artificial
<220> FEATURE:
<223> OTHER INFORMATION: Description of Artificial Sequence: mutein

<400> SEQUENCE: 42

```
Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Ala Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg
```

<210> SEQ ID NO 43
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 43

```
Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Ile Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125
```

```
Leu Arg Ser Leu Thr Thr Leu Leu Arg Ala Leu Gly Ala Gln Lys Glu
        130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
        180                 185                 190

Arg

<210> SEQ ID NO 44
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 44

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Asp Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
        130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
        180                 185                 190

Arg

<210> SEQ ID NO 45
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 45

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
```

-continued

```
                35                  40                  45
Ala Glu Asn Ile Thr Thr Gly Cys Ala Glu His Cys Ser Leu Asn Glu
            50                  55                  60
Asn Ile Thr Val Pro Asp Thr Ala Val Asn Phe Tyr Ala Trp Lys Arg
 65                  70                  75                  80
Met Glu Val Gly Gln Gln Ala Val Glu Val Trp Gln Gly Leu Ala Leu
                 85                  90                  95
Leu Ser Glu Ala Val Leu Arg Gly Gln Ala Leu Leu Val Asn Ser Ser
                100                 105                 110
Gln Pro Trp Glu Pro Leu Gln Leu His Val Asp Lys Ala Val Ser Gly
                115                 120                 125
Leu Arg Ser Leu Thr Thr Leu Leu Arg Ala Leu Gly Ala Gln Lys Glu
            130                 135                 140
Ala Ile Ser Pro Pro Asp Ala Ala Ser Ala Ala Pro Leu Arg Thr Ile
145                 150                 155                 160
Thr Ala Asp Thr Phe Arg Lys Leu Phe Arg Val Tyr Ser Asn Phe Leu
                165                 170                 175
Arg Gly Lys Leu Lys Leu Tyr Thr Gly Glu Ala Cys Arg Thr Gly Asp
                180                 185                 190
Arg

<210> SEQ ID NO 46
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 46

Met Gly Val His Glu Cys Pro Ala Trp Leu Trp Leu Leu Ser Leu
 1               5                  10                  15
Leu Ser Leu Pro Leu Gly Leu Pro Val Leu Gly Ala Pro Pro Arg Leu
                 20                  25                  30
Ile Cys Asp Ser Arg Val Leu Glu Arg Tyr Leu Leu Glu Ala Lys Glu
             35                  40                  45
Ala Glu Asn Ile Thr Thr Gly Cys Ala Glu His Cys Ser Leu Asn Glu
         50                  55                  60
Asn Ile Thr Val Pro Asp Thr Lys Ala Asn Phe Tyr Ala Trp Lys Arg
 65                  70                  75                  80
Met Glu Val Gly Gln Gln Ala Val Glu Val Trp Gln Gly Leu Ala Leu
                 85                  90                  95
Leu Ser Glu Ala Val Leu Arg Gly Gln Ala Leu Leu Val Asn Ser Ser
                100                 105                 110
Gln Pro Trp Glu Pro Leu Gln Leu His Val Asp Lys Ala Val Ser Gly
                115                 120                 125
Leu Arg Ser Leu Thr Thr Leu Leu Arg Ala Leu Gly Ala Gln Lys Glu
            130                 135                 140
Ala Ile Ser Pro Pro Asp Ala Ala Ser Ala Ala Pro Leu Arg Thr Ile
145                 150                 155                 160
Thr Ala Asp Thr Phe Arg Lys Leu Phe Arg Val Tyr Ser Asn Phe Leu
                165                 170                 175
Arg Gly Lys Leu Lys Leu Tyr Thr Gly Glu Ala Cys Arg Thr Gly Asp
                180                 185                 190
Arg
```

```
<210> SEQ ID NO 47
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 47

Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Ala Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 48
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 48

Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Ile Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110
```

```
Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 49
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 49

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Ala Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 50
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 50

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
```

```
                    20                  25                  30

Ile Cys Asp Ser Arg Val Leu Glu Arg Tyr Leu Leu Glu Ala Lys Glu
             35                  40                  45

Ala Glu Asn Ile Thr Thr Gly Cys Ala Glu His Cys Ser Leu Asn Glu
 50                  55                  60

Asn Ile Thr Val Pro Asp Thr Lys Val Asn Phe Ala Ala Trp Lys Arg
 65                  70                  75                  80

Met Glu Val Gly Gln Gln Ala Val Glu Val Trp Gln Gly Leu Ala Leu
                 85                  90                  95

Leu Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Val Ser Gly
            115                 120                 125

Leu Arg Ser Leu Thr Thr Leu Leu Arg Ala Leu Gly Ala Gln Lys Glu
        130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 51
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 51

Met Gly Val His Glu Cys Pro Ala Trp Leu Trp Leu Leu Leu Ser Leu
  1               5                  10                  15

Leu Ser Leu Pro Leu Gly Leu Pro Val Leu Gly Ala Pro Pro Arg Leu
             20                  25                  30

Ile Cys Asp Ser Arg Val Leu Glu Arg Tyr Leu Leu Glu Ala Lys Glu
             35                  40                  45

Ala Glu Asn Ile Thr Thr Gly Cys Ala Glu His Cys Ser Leu Asn Glu
 50                  55                  60

Asn Ile Thr Val Pro Asp Thr Lys Val Asn Phe Ser Ala Trp Lys Arg
 65                  70                  75                  80

Met Glu Val Gly Gln Gln Ala Val Glu Val Trp Gln Gly Leu Ala Leu
                 85                  90                  95

Leu Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Val Ser Gly
            115                 120                 125

Leu Arg Ser Leu Thr Thr Leu Leu Arg Ala Leu Gly Ala Gln Lys Glu
        130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190
```

<210> SEQ ID NO 52
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 52

```
Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Phe Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg
```

<210> SEQ ID NO 53
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 53

```
Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Asn Lys Arg
65                  70                  75                  80

Met Glu Val Gly Gln Gln Ala Val Glu Val Trp Gln Gly Leu Ala Leu
                85                  90                  95
```

-continued

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 54
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 54

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Ala Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 55
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 55

Met Gly Val His Glu Cys Pro Ala Trp Leu Trp Leu Leu Leu Ser Leu

```
                1               5                  10                 15
Leu Ser Leu Pro Leu Gly Leu Pro Val Leu Gly Ala Pro Pro Arg Leu
                    20                  25                 30

Ile Cys Asp Ser Arg Val Leu Glu Arg Tyr Leu Leu Glu Ala Lys Glu
                    35                  40                 45

Ala Glu Asn Ile Thr Thr Gly Cys Ala Glu His Cys Ser Leu Asn Glu
            50                  55                 60

Asn Ile Thr Val Pro Asp Thr Lys Val Asn Phe Tyr Ala Trp Lys Arg
65                      70                 75                      80

Met Glu Val Gly Gln Asn Ala Val Glu Val Trp Gln Gly Leu Ala Leu
                    85                  90                 95

Leu Ser Glu Ala Val Leu Arg Gly Gln Ala Leu Leu Val Asn Ser Ser
                    100                 105                110

Gln Pro Trp Glu Pro Leu Gln Leu His Val Asp Lys Ala Val Ser Gly
                115                 120                125

Leu Arg Ser Leu Thr Thr Leu Leu Arg Ala Leu Gly Ala Gln Lys Glu
            130                 135                140

Ala Ile Ser Pro Pro Asp Ala Ala Ser Ala Ala Pro Leu Arg Thr Ile
145                     150                155                     160

Thr Ala Asp Thr Phe Arg Lys Leu Phe Arg Val Tyr Ser Asn Phe Leu
                165                 170                175

Arg Gly Lys Leu Lys Leu Tyr Thr Gly Glu Ala Cys Arg Thr Gly Asp
                180                 185                190

Arg

<210> SEQ ID NO 56
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 56

Met Gly Val His Glu Cys Pro Ala Trp Leu Trp Leu Leu Leu Ser Leu
1               5                   10                 15

Leu Ser Leu Pro Leu Gly Leu Pro Val Leu Gly Ala Pro Pro Arg Leu
                    20                  25                 30

Ile Cys Asp Ser Arg Val Leu Glu Arg Tyr Leu Leu Glu Ala Lys Glu
                    35                  40                 45

Ala Glu Asn Ile Thr Thr Gly Cys Ala Glu His Cys Ser Leu Asn Glu
            50                  55                 60

Asn Ile Thr Val Pro Asp Thr Lys Val Asn Phe Tyr Ala Trp Lys Arg
65                      70                 75                      80

Met Glu Val Gly Gln Gln Ala Val Thr Val Trp Gln Gly Leu Ala Leu
                    85                  90                 95

Leu Ser Glu Ala Val Leu Arg Gly Gln Ala Leu Leu Val Asn Ser Ser
                    100                 105                110

Gln Pro Trp Glu Pro Leu Gln Leu His Val Asp Lys Ala Val Ser Gly
                115                 120                125

Leu Arg Ser Leu Thr Thr Leu Leu Arg Ala Leu Gly Ala Gln Lys Glu
            130                 135                140

Ala Ile Ser Pro Pro Asp Ala Ala Ser Ala Ala Pro Leu Arg Thr Ile
145                     150                155                     160

Thr Ala Asp Thr Phe Arg Lys Leu Phe Arg Val Tyr Ser Asn Phe Leu
                165                 170                175
```

```
Arg Gly Lys Leu Lys Leu Tyr Thr Gly Glu Ala Cys Arg Thr Gly Asp
            180                 185                 190

Arg

<210> SEQ ID NO 57
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 57

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Ser Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 58
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 58

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80
```

```
Met Glu Val Gly Gln Gln Ala Val Glu Val Trp Gln Gly Leu Ala Leu
                85                  90                  95

Ala Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Val Ser Gly
                115                 120                 125

Leu Arg Ser Leu Thr Thr Leu Leu Arg Ala Leu Gly Ala Gln Lys Glu
            130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
                180                 185                 190

Arg
```

<210> SEQ ID NO 59
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 59

```
Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
                20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
                100                 105                 110

Gln Pro Trp Glu Pro Leu Gln Leu His Val Arg Lys Ala Val Ser Gly
                115                 120                 125

Leu Arg Ser Leu Thr Thr Leu Leu Arg Ala Leu Gly Ala Gln Lys Glu
            130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
                180                 185                 190

Arg
```

<210> SEQ ID NO 60
<211> LENGTH: 193
<212> TYPE: PRT
<213> ORGANISM: Artificial
<220> FEATURE:
<223> OTHER INFORMATION: Description of Artificial Sequence: mutein -continued

```
<400> SEQUENCE: 60

Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Ala Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 61
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 61

Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Arg Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160
```

```
Thr Ala Asp Thr Phe Arg Lys Leu Phe Arg Val Tyr Ser Asn Phe Leu
            165                 170                 175

Arg Gly Lys Leu Lys Leu Tyr Thr Gly Glu Ala Cys Arg Thr Gly Asp
            180                 185                 190

Arg

<210> SEQ ID NO 62
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 62

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
        50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Glu Gly
            115                 120                 125

Leu Arg Ser Leu Thr Thr Leu Leu Arg Ala Leu Gly Ala Gln Lys Glu
            130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
            165                 170                 175

Arg Gly Lys Leu Lys Leu Tyr Thr Gly Glu Ala Cys Arg Thr Gly Asp
            180                 185                 190

Arg

<210> SEQ ID NO 63
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 63

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
        50                  55                  60
```

-continued

```
Asn Ile Thr Val Pro Asp Thr Lys Val Asn Phe Tyr Ala Trp Lys Arg
 65                  70                  75                  80

Met Glu Val Gly Gln Gln Ala Val Glu Val Trp Gln Gly Leu Ala Leu
                 85                  90                  95

Leu Ser Glu Ala Val Leu Arg Gly Gln Ala Leu Leu Val Asn Ser Ser
             100                 105                 110

Gln Pro Trp Glu Pro Leu Gln Leu His Val Asp Lys Ala Val Ala Gly
         115                 120                 125

Leu Arg Ser Leu Thr Thr Leu Leu Arg Ala Leu Gly Ala Gln Lys Glu
     130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg
```

<210> SEQ ID NO 64
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 64

```
Met Gly Val His Glu Cys Pro Ala Trp Leu Trp Leu Leu Leu Ser Leu
  1               5                  10                  15

Leu Ser Leu Pro Leu Gly Leu Pro Val Leu Gly Ala Pro Pro Arg Leu
                 20                  25                  30

Ile Cys Asp Ser Arg Val Leu Glu Arg Tyr Leu Leu Glu Ala Lys Glu
             35                  40                  45

Ala Glu Asn Ile Thr Thr Gly Cys Ala Glu His Cys Ser Leu Asn Glu
 50                  55                  60

Asn Ile Thr Val Pro Asp Thr Lys Val Asn Phe Tyr Ala Trp Lys Arg
 65                  70                  75                  80

Met Glu Val Gly Gln Gln Ala Val Glu Val Trp Gln Gly Leu Ala Leu
                 85                  90                  95

Leu Ser Glu Ala Val Leu Arg Gly Gln Ala Leu Leu Val Asn Ser Ser
             100                 105                 110

Gln Pro Trp Glu Pro Leu Gln Leu His Val Asp Lys Ala Val Thr Gly
         115                 120                 125

Leu Arg Ser Leu Thr Thr Leu Leu Arg Ala Leu Gly Ala Gln Lys Glu
     130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg
```

<210> SEQ ID NO 65
<211> LENGTH: 193
<212> TYPE: PRT
<213> ORGANISM: Artificial

```
<220> FEATURE:
<223> OTHER INFORMATION: Description of Artificial Sequence: mutein

<400> SEQUENCE: 65

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Ala
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 66
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 66

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Ile
        115                 120                 125

Leu Arg Ser Leu Thr Thr Leu Leu Arg Ala Leu Gly Ala Gln Lys Glu
    130                 135                 140
```

```
Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 67
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 67

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
                20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Ala Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 68
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 68

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
                20                  25                  30

Ile Cys Asp Ser Arg Val Leu Glu Arg Tyr Leu Leu Glu Ala Lys Glu
            35                  40                  45
```

```
Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Val Ser Gly
                115                 120                 125

Leu Ala Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
                180                 185                 190

Arg

<210> SEQ ID NO 69
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 69

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
                20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Val Ser Gly
                115                 120                 125

Leu Glu Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
                180                 185                 190

Arg

<210> SEQ ID NO 70
```

-continued

```
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 70

Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ala Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 71
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 71

Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125
```

```
Leu Arg Ile Leu Thr Thr Leu Leu Arg Ala Leu Gly Ala Gln Lys Glu
        130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
                180                 185                 190

Arg

<210> SEQ ID NO 72
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 72

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
                20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
        50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Val Ser Gly
            115                 120                 125

Leu Arg Ser Ala Thr Thr Leu Leu Arg Ala Leu Gly Ala Gln Lys Glu
        130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
                180                 185                 190

Arg

<210> SEQ ID NO 73
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 73

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
                20                  25                  30
```

```
Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
 50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Val Ser Gly
                115                 120                 125

Leu Arg Ser Leu Ala Thr Leu Leu Arg Ala Leu Gly Ala Gln Lys Glu
                130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
                180                 185                 190

Arg

<210> SEQ ID NO 74
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 74

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
                20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
 50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Val Ser Gly
                115                 120                 125

Leu Arg Ser Leu Ile Thr Leu Leu Arg Ala Leu Gly Ala Gln Lys Glu
                130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
                180                 185                 190

Arg
```

<210> SEQ ID NO 75
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 75

```
Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Ala Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg
```

<210> SEQ ID NO 76
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 76

```
Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110
```

```
Gln Pro Trp Glu Pro Leu Gln Leu His Val Asp Lys Ala Val Ser Gly
        115                 120                 125

Leu Arg Ser Leu Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
                180                 185                 190

Arg

<210> SEQ ID NO 77
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 77

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
                20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
        50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Val Ser Gly
        115                 120                 125

Leu Arg Ser Leu Thr Thr Lys Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
                180                 185                 190

Arg

<210> SEQ ID NO 78
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 78

Met Gly Val His Glu Cys Pro Ala Trp Leu Trp Leu Leu Leu Ser Leu
1               5                   10                  15
```

-continued

```
Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
 50                  55                  60

Asn Ile Thr Val Pro Asp Thr Lys Val Asn Phe Tyr Ala Trp Lys Arg
 65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Val Ser Gly
            115                 120                 125

Leu Arg Ser Leu Thr Thr Ala Leu Arg Ala Leu Gly Ala Gln Lys Glu
130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
                180                 185                 190

Arg
```

<210> SEQ ID NO 79
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 79

```
Met Gly Val His Glu Cys Pro Ala Trp Leu Trp Leu Leu Leu Ser Leu
 1               5                  10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
 50                  55                  60

Asn Ile Thr Val Pro Asp Thr Lys Val Asn Phe Tyr Ala Trp Lys Arg
 65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Val Ser Gly
            115                 120                 125

Leu Arg Ser Leu Thr Thr Ser Leu Arg Ala Leu Gly Ala Gln Lys Glu
130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
```

```
                    180                 185                 190

Arg

<210> SEQ ID NO 80
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 80

Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Arg Leu
                20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
        50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Val Ser Gly
                115                 120                 125

Leu Arg Ser Leu Thr Thr Leu Leu Arg Ala Leu Gly Ala Gln Ala Glu
        130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
                180                 185                 190

Arg

<210> SEQ ID NO 81
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 81

Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Arg Leu
                20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
        50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95
```

-continued

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 82
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 82

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Ala Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 83
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 83

```
Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
        50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ala
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 84
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 84

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
        50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Ala Ala Asp Thr Phe Arg Lys Leu Phe Arg Val Tyr Ser Asn Phe Leu
```

```
                    165                 170                 175

Arg Gly Lys Leu Lys Leu Tyr Thr Gly Glu Ala Cys Arg Thr Gly Asp
            180                 185                 190

Arg

<210> SEQ ID NO 85
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 85

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Ala Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 86
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 86

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80
```

```
Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Ile Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg
```

```
<210> SEQ ID NO 87
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 87

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Ala Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg
```

```
<210> SEQ ID NO 88
<211> LENGTH: 193
<212> TYPE: PRT
<213> ORGANISM: Artificial
<220> FEATURE:
<223> OTHER INFORMATION: Description of Artificial Sequence: mutein
```

```
<400> SEQUENCE: 88

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ala Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 89
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 89

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
```

```
                 145                 150                 155                 160
Thr Ala Asp Thr Phe Arg Lys Leu Phe Arg Val Tyr Ser Lys Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 90
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 90

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Ala Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 91
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 91

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60
```

```
Asn Ile Thr Val Pro Asp Thr Lys Val Asn Phe Tyr Ala Trp Lys Arg
 65                  70                  75                  80

Met Glu Val Gly Gln Gln Ala Val Glu Val Trp Gln Gly Leu Ala Leu
                 85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Tyr Leu
                165                 170                 175

Arg Gly Lys Leu Lys Leu Tyr Thr Gly Glu Ala Cys Arg Thr Gly Asp
            180                 185                 190

Arg

<210> SEQ ID NO 92
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 92

Met Gly Val His Glu Cys Pro Ala Trp Leu Trp Leu Leu Leu Ser Leu
  1               5                  10                  15

Leu Ser Leu Pro Leu Gly Leu Pro Val Leu Gly Ala Pro Pro Arg Leu
                 20                  25                  30

Ile Cys Asp Ser Arg Val Leu Glu Arg Tyr Leu Leu Glu Ala Lys Glu
             35                  40                  45

Ala Glu Asn Ile Thr Thr Gly Cys Ala Glu His Cys Ser Leu Asn Glu
         50                  55                  60

Asn Ile Thr Val Pro Asp Thr Lys Val Asn Phe Tyr Ala Trp Lys Arg
 65                  70                  75                  80

Met Glu Val Gly Gln Gln Ala Val Glu Val Trp Gln Gly Leu Ala Leu
                 85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Ala Leu
                165                 170                 175

Arg Gly Lys Leu Lys Leu Tyr Thr Gly Glu Ala Cys Arg Thr Gly Asp
            180                 185                 190

Arg

<210> SEQ ID NO 93
<211> LENGTH: 193
<212> TYPE: PRT
```

```
<213> ORGANISM: Artificial
<220> FEATURE:
<223> OTHER INFORMATION: Description of Artificial Sequence: mutein

<400> SEQUENCE: 93

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Ala
                165                 170                 175

Arg Gly Lys Leu Lys Leu Tyr Thr Gly Glu Ala Cys Arg Thr Gly Asp
            180                 185                 190

Arg

<210> SEQ ID NO 94
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 94

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
```

```
                130             135             140
Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Ala Gly Lys Leu Lys Leu Tyr Thr Gly Glu Ala Cys Arg Thr Gly Asp
            180                 185                 190

Arg

<210> SEQ ID NO 95
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 95

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
                20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
        50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Val Ser Gly
            115                 120                 125

Leu Arg Ser Leu Thr Thr Leu Leu Arg Ala Leu Gly Ala Gln Lys Glu
        130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Glu Gly Lys Leu Lys Leu Tyr Thr Gly Glu Ala Cys Arg Thr Gly Asp
            180                 185                 190

Arg

<210> SEQ ID NO 96
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 96

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
                20                  25                  30

Ile Cys Asp Ser Arg Val Leu Glu Arg Tyr Leu Leu Glu Ala Lys Glu
            35                  40                  45
```

-continued

Ala Glu Asn Ile Thr Thr Gly Cys Ala Glu His Cys Ser Leu Asn Glu
            50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Ala Lys Leu Lys Leu Tyr Thr Gly Glu Ala Cys Arg Thr Gly Asp
            180                 185                 190

Arg

<210> SEQ ID NO 97
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 97

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Ala Leu Lys Leu Tyr Thr Gly Glu Ala Cys Arg Thr Gly Asp
            180                 185                 190

Arg

<210> SEQ ID NO 98
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 98

```
Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Trp Leu Lys Leu Tyr Thr Gly Glu Ala Cys Arg Thr Gly Asp
            180                 185                 190

Arg
```

<210> SEQ ID NO 99
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 99

```
Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
```

-continued

```
            115                 120                 125
Leu Arg Ser Leu Thr Thr Leu Leu Arg Ala Leu Gly Ala Gln Lys Glu
        130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Ala Lys Leu Tyr Thr Gly Glu Ala Cys Arg Thr Gly Asp
                180                 185                 190

Arg

<210> SEQ ID NO 100
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 100

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Ala Leu Tyr Thr Gly Glu Ala Cys Arg Thr Gly Asp
                180                 185                 190

Arg

<210> SEQ ID NO 101
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 101

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30
```

```
Ile Cys Asp Ser Arg Val Leu Glu Arg Tyr Leu Leu Glu Ala Lys Glu
         35                  40                  45

Ala Glu Asn Ile Thr Thr Gly Cys Ala Glu His Cys Ser Leu Asn Glu
 50                  55                  60

Asn Ile Thr Val Pro Asp Thr Lys Val Asn Phe Tyr Ala Trp Lys Arg
 65                  70                  75                  80

Met Glu Val Gly Gln Gln Ala Val Glu Val Trp Gln Gly Leu Ala Leu
                 85                  90                  95

Leu Ser Glu Ala Val Leu Arg Gly Gln Ala Leu Leu Val Asn Ser Ser
             100                 105                 110

Gln Pro Trp Glu Pro Leu Gln Leu His Val Asp Lys Ala Val Ser Gly
         115                 120                 125

Leu Arg Ser Leu Thr Thr Leu Leu Arg Ala Leu Gly Ala Gln Lys Glu
     130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                 165                 170                 175

Arg Gly Lys Leu Lys Ala Tyr Thr Gly Glu Ala Cys Arg Thr Gly Asp
             180                 185                 190

Arg
```

<210> SEQ ID NO 102
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 102

```
Met Gly Val His Glu Cys Pro Ala Trp Leu Trp Leu Leu Leu Ser Leu
 1               5                  10                  15

Leu Ser Leu Pro Leu Gly Leu Pro Val Leu Gly Ala Pro Pro Arg Leu
                 20                  25                  30

Ile Cys Asp Ser Arg Val Leu Glu Arg Tyr Leu Leu Glu Ala Lys Glu
         35                  40                  45

Ala Glu Asn Ile Thr Thr Gly Cys Ala Glu His Cys Ser Leu Asn Glu
 50                  55                  60

Asn Ile Thr Val Pro Asp Thr Lys Val Asn Phe Tyr Ala Trp Lys Arg
 65                  70                  75                  80

Met Glu Val Gly Gln Gln Ala Val Glu Val Trp Gln Gly Leu Ala Leu
                 85                  90                  95

Leu Ser Glu Ala Val Leu Arg Gly Gln Ala Leu Leu Val Asn Ser Ser
             100                 105                 110

Gln Pro Trp Glu Pro Leu Gln Leu His Val Asp Lys Ala Val Ser Gly
         115                 120                 125

Leu Arg Ser Leu Thr Thr Leu Leu Arg Ala Leu Gly Ala Gln Lys Glu
     130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                 165                 170                 175

Arg Gly Lys Leu Lys Leu Tyr Thr Ala Glu Ala Cys Arg Thr Gly Asp
             180                 185                 190
```

Arg

```
<210> SEQ ID NO 103
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 103
```

Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Ser Arg Thr Gly Asp
            180                 185                 190

Arg

```
<210> SEQ ID NO 104
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 104
```

Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser

```
            100                 105                 110
Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Ala Arg Thr Gly Asp
            180                 185                 190

Arg

<210> SEQ ID NO 105
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 105

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Ala Thr Gly Asp
            180                 185                 190

Arg

<210> SEQ ID NO 106
<211> LENGTH: 192
<212> TYPE: PRT
<213> ORGANISM: Artificial
<220> FEATURE:
<223> OTHER INFORMATION: Description of Artificial Sequence: mutein

<400> SEQUENCE: 106

Met Gly Val His Glu Cys Pro Ala Trp Leu Trp Leu Leu Leu Ser Leu
1               5                   10                  15
```

```
Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Glu His Cys Ser Leu Asn Glu Asn
    50                  55                  60

Ile Thr Val Pro Asp Thr Asp Val Asn Phe Tyr Ala Trp Lys Arg Met
65                  70                  75                  80

Glu Val Gly Gln Gln Ala Val Glu Val Trp Gln Gly Leu Ala Leu Leu
                85                  90                  95

Ser Glu Ala Val Leu Arg Gly Gln Ala Leu Leu Val Asn Ser Ser Gln
            100                 105                 110

Pro Trp Glu Pro Leu Gln Leu His Val Asp Lys Ala Val Glu Gly Leu
        115                 120                 125

Arg Ser Leu Thr Thr Leu Leu Arg Ala Leu Gly Ala Gln Lys Glu Ala
    130                 135                 140

Ile Ser Pro Pro Asp Ala Ala Ser Ala Ala Pro Leu Arg Thr Ile Thr
145                 150                 155                 160

Ala Asp Thr Phe Arg Lys Leu Phe Arg Val Tyr Ser Asn Phe Leu Arg
                165                 170                 175

Gly Lys Leu Lys Leu Tyr Thr Gly Glu Ala Cys Arg Thr Gly Asp Arg
            180                 185                 190

<210> SEQ ID NO 107
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 107

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Asn Glu Thr Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190
```

<210> SEQ ID NO 108
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 108

```
Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Asp Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Glu Gly Lys Leu Lys Leu Tyr Thr Gly Glu Ala Cys Arg Thr Gly Asp
            180                 185                 190

Arg
```

<210> SEQ ID NO 109
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 109

```
Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95
```

Leu Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Val Ser Gly
            115                 120                 125

Leu Glu Ser Leu Thr Thr Ser Leu Arg Ala Leu Gly Ala Gln Lys Glu
        130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 110
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 110

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
                20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
        50                  55                  60

Asn Ile Thr Val Pro Asp Thr Lys Val Asn Phe Tyr Ala Trp Ala Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Val Ser Gly
            115                 120                 125

Leu Arg Ser Leu Thr Thr Leu Leu Arg Ala Leu Gly Ala Gln Lys Glu
        130                 135                 140

Ala Ile Ser Pro Pro Asp Ala Ala Ser Ala Ala Pro Leu Arg Thr Ile
145                 150                 155                 160

Thr Ala Asp Thr Phe Arg Ala Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 111
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 111

Met Gly Val His Glu Cys Pro Ala Trp Leu Trp Leu Leu Leu Ser Leu

```
                 1               5                  10                 15
Leu Ser Leu Pro Leu Gly Leu Pro Val Leu Gly Ala Pro Pro Arg Leu
                20                 25                 30

Ile Cys Asp Ser Arg Val Leu Glu Arg Tyr Leu Leu Glu Ala Lys Glu
                35                 40                 45

Ala Glu Asn Ile Thr Thr Gly Cys Ala Glu His Cys Ser Leu Asn Glu
            50                 55                 60

Asn Ile Thr Val Pro Asp Thr Ala Val Asn Phe Tyr Ala Trp Ala Arg
65                  70                 75                  80

Met Glu Val Gly Gln Gln Ala Val Glu Val Trp Gln Gly Leu Ala Leu
                85                 90                 95

Leu Ser Glu Ala Val Leu Arg Gly Gln Ala Leu Leu Val Asn Ser Ser
                100                105                110

Gln Pro Trp Glu Pro Leu Gln Leu His Val Asp Lys Ala Val Ser Gly
            115                120                125

Leu Arg Ser Leu Thr Thr Leu Leu Arg Ala Leu Gly Ala Gln Lys Glu
            130                135                140

Ala Ile Ser Pro Pro Asp Ala Ala Ser Ala Ala Pro Leu Arg Thr Ile
145                 150                155                160

Thr Ala Asp Thr Phe Arg Ala Leu Phe Arg Val Tyr Ser Asn Phe Leu
                165                170                175

Arg Gly Lys Leu Lys Leu Tyr Thr Gly Glu Ala Cys Arg Thr Gly Asp
            180                185                190

Arg

<210> SEQ ID NO 112
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 112

Met Gly Val His Glu Cys Pro Ala Trp Leu Trp Leu Leu Leu Ser Leu
1               5                  10                 15

Leu Ser Leu Pro Leu Gly Leu Pro Val Leu Gly Ala Pro Pro Arg Leu
                20                 25                 30

Ile Cys Asp Ser Arg Val Leu Glu Arg Tyr Leu Leu Glu Ala Lys Glu
                35                 40                 45

Ala Glu Asn Ile Thr Thr Gly Cys Ala Glu His Cys Ser Leu Asn Glu
            50                 55                 60

Asn Ile Thr Val Pro Asp Thr Lys Val Asn Phe Tyr Ala Trp Lys Arg
65                  70                 75                  80

Met Glu Val Gly Gln Gln Ala Val Glu Val Trp Gln Gly Leu Ala Leu
                85                 90                 95

Leu Ser Glu Ala Val Leu Arg Gly Gln Ala Leu Leu Val Asn Ser Ser
                100                105                110

Gln Pro Trp Glu Pro Leu Gln Leu His Val Asp Lys Ala Val Ser Gly
            115                120                125

Leu Arg Ser Leu Thr Thr Leu Leu Arg Ala Leu Gly Ala Gln Lys Glu
            130                135                140

Ala Ile Ser Pro Pro Asp Ala Ala Ser Ala Ala Pro Leu Arg Thr Ile
145                 150                155                160

Thr Ala Asp Thr Phe Arg Lys Leu Phe Arg Val Tyr Ser Asn Phe Leu
                165                170                175
```

```
Arg Gly Lys Leu Lys Leu Tyr Thr Gly Glu Ala Cys Arg Thr Gly Asp
            180                 185                 190

Arg

<210> SEQ ID NO 113
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 113

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Ala Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Ala Leu Lys Leu Tyr Thr Gly Glu Ala Cys Arg Thr Gly Asp
            180                 185                 190

Arg

<210> SEQ ID NO 114
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 114

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Ala Val Asn Phe Tyr Ala Trp Lys Arg
65                  70                  75                  80
```

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Ala Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Ala Leu Lys Leu Tyr Thr Gly Glu Ala Cys Arg Thr Gly Asp
            180                 185                 190

Arg

<210> SEQ ID NO 115
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 115

Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Arg Leu
                20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
50                  55                  60

Asn Ile Thr Val Pro Asp Thr Ala Val Asn Phe Tyr Ala Trp Ala Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Ala Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Ala Leu Phe Arg Val Tyr Ser Asn Phe Leu
                165                 170                 175

Arg Gly Ala Leu Lys Leu Tyr Thr Gly Glu Ala Cys Arg Thr Gly Asp
            180                 185                 190

Arg

<210> SEQ ID NO 116
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 116

```
Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Ala Val Asn Phe Tyr Ala Trp Ala Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Ala Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Ala Leu Phe Arg Val Tyr Ser Asn Phe Leu
                165                 170                 175

Arg Gly Ala Leu Ala Leu Tyr Thr Gly Glu Ala Cys Arg Thr Gly Asp
            180                 185                 190

Arg
```

<210> SEQ ID NO 117
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 117

```
Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Lys Ile Thr Thr Gly Cys Ala Glu His Cys Ser Leu Asn Glu
    50                  55                  60

Lys Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Lys Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160
```

```
Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 118
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 118

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Ala Leu Leu Glu Ala Lys Glu
        35                  40                  45

Ala Glu Lys Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 119
<211> LENGTH: 193
<212> TYPE: PRT
<213> ORGANISM: Artificial
<220> FEATURE:
<223> OTHER INFORMATION: Description of Artificial Sequence: mutein

<400> SEQUENCE: 119

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Ala Ala Leu Leu Glu Ala Lys Glu
        35                  40                  45

Ala Glu Asn Ile Thr Thr Gly Cys Ala Glu His Cys Ser Leu Asn Glu
    50                  55                  60
```

```
Asn Ile Thr Val Pro Asp Thr Lys Val Asn Phe Tyr Ala Trp Lys Arg
 65                  70                  75                  80

Met Glu Val Gly Gln Gln Ala Val Glu Val Trp Gln Gly Leu Ala Leu
                 85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 120
<211> LENGTH: 36
<212> TYPE: DNA
<213> ORGANISM: Artificial
<220> FEATURE:
<223> OTHER INFORMATION: Description of Artificial Sequence: primer

<400> SEQUENCE: 120
gtctactcca atttcctcga gggaaagctg aagctg                            36

<210> SEQ ID NO 121
<211> LENGTH: 34
<212> TYPE: DNA
<213> ORGANISM: Artificial
<220> FEATURE:
<223> OTHER INFORMATION: Description of Artificial Sequence: primer

<400> SEQUENCE: 121
gcttcagctt tccctcgagg aaattggagt agac                              34

<210> SEQ ID NO 122
<211> LENGTH: 32
<212> TYPE: DNA
<213> ORGANISM: Artificial
<220> FEATURE:
<223> OTHER INFORMATION: Description of Artificial Sequence: primer

<400> SEQUENCE: 122
ccgtcagtgg ccttgagagc ctcaccactc tg                                32

<210> SEQ ID NO 123
<211> LENGTH: 32
<212> TYPE: DNA
<213> ORGANISM: Artificial
<220> FEATURE:
<223> OTHER INFORMATION: Description of Artificial Sequence: primer

<400> SEQUENCE: 123
cagagtggtg aggctctcaa ggccactgac gg                                32

<210> SEQ ID NO 124
<211> LENGTH: 32
<212> TYPE: DNA
<213> ORGANISM: Artificial
```

```
<220> FEATURE:
<223> OTHER INFORMATION: Description of Artificial Sequence: primer

<400> SEQUENCE: 124
ccgtcagtgg ccttgagagc ctcaccactc tg                                     32

<210> SEQ ID NO 125
<211> LENGTH: 32
<212> TYPE: DNA
<213> ORGANISM: Artificial
<220> FEATURE:
<223> OTHER INFORMATION: Description of Artificial Sequence: primer

<400> SEQUENCE: 125
cagagtggtg aggctctcaa ggccactgac gg                                     32

<210> SEQ ID NO 126
<211> LENGTH: 31
<212> TYPE: DNA
<213> ORGANISM: Artificial
<220> FEATURE:
<223> OTHER INFORMATION: Description of Artificial Sequence: primer

<400> SEQUENCE: 126
cgcagcctca ccacttcgct tcgggctctg g                                      31

<210> SEQ ID NO 127
<211> LENGTH: 31
<212> TYPE: DNA
<213> ORGANISM: Artificial
<220> FEATURE:
<223> OTHER INFORMATION: Description of Artificial Sequence: primer

<400> SEQUENCE: 127
ccagagcccg aagcgaagtg gtgaggctgc g                                      31

<210> SEQ ID NO 128
<211> LENGTH: 40
<212> TYPE: DNA
<213> ORGANISM: Artificial
<220> FEATURE:
<223> OTHER INFORMATION: Description of Artificial Sequence: primer

<400> SEQUENCE: 128
gaatatcact gtcccagacg gtggtgcctg gaagaggatg                             40

<210> SEQ ID NO 129
<211> LENGTH: 40
<212> TYPE: DNA
<213> ORGANISM: Artificial
<220> FEATURE:
<223> OTHER INFORMATION: Description of Artificial Sequence: primer

<400> SEQUENCE: 129
catcctcttc caggcaccac cgtctgggac agtgatattc                             40

<210> SEQ ID NO 130
<211> LENGTH: 33
<212> TYPE: DNA
<213> ORGANISM: Artificial
<220> FEATURE:
<223> OTHER INFORMATION: Description of Artificial Sequence: primer

<400> SEQUENCE: 130
tacctcttgg aggccgcgga ggccgagaat atc                                    33
```

<210> SEQ ID NO 131
<211> LENGTH: 33
<212> TYPE: DNA
<213> ORGANISM: Artificial
<220> FEATURE:
<223> OTHER INFORMATION: Description of Artificial Sequence: primer

<400> SEQUENCE: 131
gatattctcg gcctccgcgg cctccaagag gta                          33

<210> SEQ ID NO 132
<211> LENGTH: 35
<212> TYPE: DNA
<213> ORGANISM: Artificial
<220> FEATURE:
<223> OTHER INFORMATION: Description of Artificial Sequence: primer

<400> SEQUENCE: 132
gctgacactt tccgcgcact cttccgagtc tactc                        35

<210> SEQ ID NO 133
<211> LENGTH: 35
<212> TYPE: DNA
<213> ORGANISM: Artificial
<220> FEATURE:
<223> OTHER INFORMATION: Description of Artificial Sequence: primer

<400> SEQUENCE: 133
gagtagactc ggaagagtgc gcggaaagtg tcagc                        35

<210> SEQ ID NO 134
<211> LENGTH: 33
<212> TYPE: DNA
<213> ORGANISM: Artificial
<220> FEATURE:
<223> OTHER INFORMATION: Description of Artificial Sequence: primer

<400> SEQUENCE: 134
atttcctccg gggagcgctg aagctgtaca cag                          33

<210> SEQ ID NO 135
<211> LENGTH: 33
<212> TYPE: DNA
<213> ORGANISM: Artificial
<220> FEATURE:
<223> OTHER INFORMATION: Description of Artificial Sequence: primer

<400> SEQUENCE: 135
ctgtgtacag cttcagcgct ccccggagga aat                          33

<210> SEQ ID NO 136
<211> LENGTH: 32
<212> TYPE: DNA
<213> ORGANISM: Artificial
<220> FEATURE:
<223> OTHER INFORMATION: Description of Artificial Sequence: primer

<400> SEQUENCE: 136
ctccggggaa agctggcgct gtacacaggg ga                           32

<210> SEQ ID NO 137
<211> LENGTH: 32
<212> TYPE: DNA
<213> ORGANISM: Artificial
<220> FEATURE:
<223> OTHER INFORMATION: Description of Artificial Sequence: primer

<400> SEQUENCE: 137
tcccctgtgt acagcgccag ctttccccgg ag                        32

<210> SEQ ID NO 138
<211> LENGTH: 35
<212> TYPE: DNA
<213> ORGANISM: Artificial
<220> FEATURE:
<223> OTHER INFORMATION: Description of Artificial Sequence: primer

<400> SEQUENCE: 138
actgtcccag acaccgcagt taatttctat gcctg                     35

<210> SEQ ID NO 139
<211> LENGTH: 35
<212> TYPE: DNA
<213> ORGANISM: Artificial
<220> FEATURE:
<223> OTHER INFORMATION: Description of Artificial Sequence: primer

<400> SEQUENCE: 139
caggcataga aattaactgc ggtgtctggg acagt                     35

<210> SEQ ID NO 140
<211> LENGTH: 35
<212> TYPE: DNA
<213> ORGANISM: Artificial
<220> FEATURE:
<223> OTHER INFORMATION: Description of Artificial Sequence: primer

<400> SEQUENCE: 140
agttaatttc tatgcctggg cgaggatgga ggtcg                     35

<210> SEQ ID NO 141
<211> LENGTH: 35
<212> TYPE: DNA
<213> ORGANISM: Artificial
<220> FEATURE:
<223> OTHER INFORMATION: Description of Artificial Sequence: primer

<400> SEQUENCE: 141
cgacctccat cctcgcccag gcatagaaat taact                     35

<210> SEQ ID NO 142
<211> LENGTH: 33
<212> TYPE: DNA
<213> ORGANISM: Artificial
<220> FEATURE:
<223> OTHER INFORMATION: Description of Artificial Sequence: primer

<400> SEQUENCE: 142
tgcagctgca tgtggatgca gccgtcagtg gcc                       33

<210> SEQ ID NO 143
<211> LENGTH: 33
<212> TYPE: DNA
<213> ORGANISM: Artificial
<220> FEATURE:
<223> OTHER INFORMATION: Description of Artificial Sequence: primer

<400> SEQUENCE: 143
ggccactgac ggctgcatcc acatgcagct gca                       33

<210> SEQ ID NO 144

```
<211> LENGTH: 32
<212> TYPE: DNA
<213> ORGANISM: Artificial
<220> FEATURE:
<223> OTHER INFORMATION: Description of Artificial Sequence: primer

<400> SEQUENCE: 144
ctctgggagc ccaggcggaa gccatctccc ct                                    32

<210> SEQ ID NO 145
<211> LENGTH: 32
<212> TYPE: DNA
<213> ORGANISM: Artificial
<220> FEATURE:
<223> OTHER INFORMATION: Description of Artificial Sequence: primer

<400> SEQUENCE: 145
aggggagatg gcttccgcct gggctcccag ag                                    32

<210> SEQ ID NO 146
<211> LENGTH: 35
<212> TYPE: DNA
<213> ORGANISM: Artificial
<220> FEATURE:
<223> OTHER INFORMATION: Description of Artificial Sequence: primer

<400> SEQUENCE: 146
gctgacactt tccgcgcact cttccgagtc tactc                                 35

<210> SEQ ID NO 147
<211> LENGTH: 35
<212> TYPE: DNA
<213> ORGANISM: Artificial
<220> FEATURE:
<223> OTHER INFORMATION: Description of Artificial Sequence: primer

<400> SEQUENCE: 147
gagtagactc ggaagagtgc gcggaaagtg tcagc                                 35

<210> SEQ ID NO 148
<211> LENGTH: 35
<212> TYPE: DNA
<213> ORGANISM: Artificial
<220> FEATURE:
<223> OTHER INFORMATION: Description of Artificial Sequence: primer

<400> SEQUENCE: 148
agttaatttc tatgcctggg cgaggatgga ggtcg                                 35

<210> SEQ ID NO 149
<211> LENGTH: 35
<212> TYPE: DNA
<213> ORGANISM: Artificial
<220> FEATURE:
<223> OTHER INFORMATION: Description of Artificial Sequence: primer

<400> SEQUENCE: 149
cgacctccat cctcgcccag gcatagaaat taact                                 35

<210> SEQ ID NO 150
<211> LENGTH: 35
<212> TYPE: DNA
<213> ORGANISM: Artificial
<220> FEATURE:
<223> OTHER INFORMATION: Description of Artificial Sequence: primer

<400> SEQUENCE: 150
```
gctgacactt tccgcgcact cttccgagtc tactc         35

<210> SEQ ID NO 151
<211> LENGTH: 35
<212> TYPE: DNA
<213> ORGANISM: Artificial
<220> FEATURE:
<223> OTHER INFORMATION: Description of Artificial Sequence: primer

<400> SEQUENCE: 151
gagtagactc ggaagagtgc gcggaaagtg tcagc         35

<210> SEQ ID NO 152
<211> LENGTH: 35
<212> TYPE: DNA
<213> ORGANISM: Artificial
<220> FEATURE:
<223> OTHER INFORMATION: Description of Artificial Sequence: primer

<400> SEQUENCE: 152
agttaatttc tatgcctggg cgaggatgga ggtcg         35

<210> SEQ ID NO 153
<211> LENGTH: 35
<212> TYPE: DNA
<213> ORGANISM: Artificial
<220> FEATURE:
<223> OTHER INFORMATION: Description of Artificial Sequence: primer

<400> SEQUENCE: 153
cgacctccat cctcgcccag gcatagaaat taact         35

<210> SEQ ID NO 154
<211> LENGTH: 35
<212> TYPE: DNA
<213> ORGANISM: Artificial
<220> FEATURE:
<223> OTHER INFORMATION: Description of Artificial Sequence: primer

<400> SEQUENCE: 154
actgtcccag acaccgcagt taatttctat gcctg         35

<210> SEQ ID NO 155
<211> LENGTH: 35
<212> TYPE: DNA
<213> ORGANISM: Artificial
<220> FEATURE:
<223> OTHER INFORMATION: Description of Artificial Sequence: primer

<400> SEQUENCE: 155
caggcataga aattaactgc ggtgtctggg acagt         35

<210> SEQ ID NO 156
<211> LENGTH: 33
<212> TYPE: DNA
<213> ORGANISM: Artificial
<220> FEATURE:
<223> OTHER INFORMATION: Description of Artificial Sequence: primer

<400> SEQUENCE: 156
tgcagctgca tgtggatgca gccgtcagtg gcc         33

<210> SEQ ID NO 157
<211> LENGTH: 33
<212> TYPE: DNA

```
<213> ORGANISM: Artificial
<220> FEATURE:
<223> OTHER INFORMATION: Description of Artificial Sequence: primer

<400> SEQUENCE: 157
ggccactgac ggctgcatcc acatgcagct gca                              33

<210> SEQ ID NO 158
<211> LENGTH: 33
<212> TYPE: DNA
<213> ORGANISM: Artificial
<220> FEATURE:
<223> OTHER INFORMATION: Description of Artificial Sequence: primer

<400> SEQUENCE: 158
atttcctccg gggagcgctg aagctgtaca cag                              33

<210> SEQ ID NO 159
<211> LENGTH: 33
<212> TYPE: DNA
<213> ORGANISM: Artificial
<220> FEATURE:
<223> OTHER INFORMATION: Description of Artificial Sequence: primer

<400> SEQUENCE: 159
ctgtgtacag cttcagcgct ccccggagga aat                              33

<210> SEQ ID NO 160
<211> LENGTH: 33
<212> TYPE: DNA
<213> ORGANISM: Artificial
<220> FEATURE:
<223> OTHER INFORMATION: Description of Artificial Sequence: primer

<400> SEQUENCE: 160
tgcagctgca tgtggatgca gccgtcagtg gcc                              33

<210> SEQ ID NO 161
<211> LENGTH: 33
<212> TYPE: DNA
<213> ORGANISM: Artificial
<220> FEATURE:
<223> OTHER INFORMATION: Description of Artificial Sequence: primer

<400> SEQUENCE: 161
ggccactgac ggctgcatcc acatgcagct gca                              33

<210> SEQ ID NO 162
<211> LENGTH: 33
<212> TYPE: DNA
<213> ORGANISM: Artificial
<220> FEATURE:
<223> OTHER INFORMATION: Description of Artificial Sequence: primer

<400> SEQUENCE: 162
atttcctccg gggagcgctg aagctgtaca cag                              33

<210> SEQ ID NO 163
<211> LENGTH: 33
<212> TYPE: DNA
<213> ORGANISM: Artificial
<220> FEATURE:
<223> OTHER INFORMATION: Description of Artificial Sequence: primer

<400> SEQUENCE: 163
ctgtgtacag cttcagcgct ccccggagga aat                              33
```

<210> SEQ ID NO 164
<211> LENGTH: 35
<212> TYPE: DNA
<213> ORGANISM: Artificial
<220> FEATURE:
<223> OTHER INFORMATION: Description of Artificial Sequence: primer

<400> SEQUENCE: 164
actgtcccag acaccgcagt taatttctat gcctg                              35

<210> SEQ ID NO 165
<211> LENGTH: 35
<212> TYPE: DNA
<213> ORGANISM: Artificial
<220> FEATURE:
<223> OTHER INFORMATION: Description of Artificial Sequence: primer

<400> SEQUENCE: 165
caggcataga aattaactgc ggtgtctggg acagt                              35

<210> SEQ ID NO 166
<211> LENGTH: 33
<212> TYPE: DNA
<213> ORGANISM: Artificial
<220> FEATURE:
<223> OTHER INFORMATION: Description of Artificial Sequence: primer

<400> SEQUENCE: 166
tgcagctgca tgtggatgca gccgtcagtg gcc                                33

<210> SEQ ID NO 167
<211> LENGTH: 33
<212> TYPE: DNA
<213> ORGANISM: Artificial
<220> FEATURE:
<223> OTHER INFORMATION: Description of Artificial Sequence: primer

<400> SEQUENCE: 167
ggccactgac ggctgcatcc acatgcagct gca                                33

<210> SEQ ID NO 168
<211> LENGTH: 33
<212> TYPE: DNA
<213> ORGANISM: Artificial
<220> FEATURE:
<223> OTHER INFORMATION: Description of Artificial Sequence: primer

<400> SEQUENCE: 168
atttcctccg gggagcgctg aagctgtaca cag                                33

<210> SEQ ID NO 169
<211> LENGTH: 33
<212> TYPE: DNA
<213> ORGANISM: Artificial
<220> FEATURE:
<223> OTHER INFORMATION: Description of Artificial Sequence: primer

<400> SEQUENCE: 169
ctgtgtacag cttcagcgct ccccggagga aat                                33

<210> SEQ ID NO 170
<211> LENGTH: 35
<212> TYPE: DNA
<213> ORGANISM: Artificial
<220> FEATURE:

<223> OTHER INFORMATION: Description of Artificial Sequence: primer

<400> SEQUENCE: 170
actgtcccag acaccgcagt taatttctat gcctg                                    35

<210> SEQ ID NO 171
<211> LENGTH: 35
<212> TYPE: DNA
<213> ORGANISM: Artificial
<220> FEATURE:
<223> OTHER INFORMATION: Description of Artificial Sequence: primer

<400> SEQUENCE: 171
caggcataga aattaactgc ggtgtctggg acagt                                    35

<210> SEQ ID NO 172
<211> LENGTH: 35
<212> TYPE: DNA
<213> ORGANISM: Artificial
<220> FEATURE:
<223> OTHER INFORMATION: Description of Artificial Sequence: primer

<400> SEQUENCE: 172
agttaatttc tatgcctggg cgaggatgga ggtcg                                    35

<210> SEQ ID NO 173
<211> LENGTH: 35
<212> TYPE: DNA
<213> ORGANISM: Artificial
<220> FEATURE:
<223> OTHER INFORMATION: Description of Artificial Sequence: primer

<400> SEQUENCE: 173
cgacctccat cctcgcccag gcatagaaat taact                                    35

<210> SEQ ID NO 174
<211> LENGTH: 33
<212> TYPE: DNA
<213> ORGANISM: Artificial
<220> FEATURE:
<223> OTHER INFORMATION: Description of Artificial Sequence: primer

<400> SEQUENCE: 174
tgcagctgca tgtggatgca gccgtcagtg gcc                                      33

<210> SEQ ID NO 175
<211> LENGTH: 33
<212> TYPE: DNA
<213> ORGANISM: Artificial
<220> FEATURE:
<223> OTHER INFORMATION: Description of Artificial Sequence: primer

<400> SEQUENCE: 175
ggccactgac ggctgcatcc acatgcagct gca                                      33

<210> SEQ ID NO 176
<211> LENGTH: 33
<212> TYPE: DNA
<213> ORGANISM: Artificial
<220> FEATURE:
<223> OTHER INFORMATION: Description of Artificial Sequence: primer

<400> SEQUENCE: 176
atttcctccg gggagcgctg aagctgtaca cag                                      33

<210> SEQ ID NO 177
<211> LENGTH: 33
<212> TYPE: DNA
<213> ORGANISM: Artificial
<220> FEATURE:
<223> OTHER INFORMATION: Description of Artificial Sequence: primer

<400> SEQUENCE: 177
ctgtgtacag cttcagcgct ccccggagga aat                                  33

<210> SEQ ID NO 178
<211> LENGTH: 35
<212> TYPE: DNA
<213> ORGANISM: Artificial
<220> FEATURE:
<223> OTHER INFORMATION: Description of Artificial Sequence: primer

<400> SEQUENCE: 178
actgtcccag acaccgcagt taatttctat gcctg                                35

<210> SEQ ID NO 179
<211> LENGTH: 35
<212> TYPE: DNA
<213> ORGANISM: Artificial
<220> FEATURE:
<223> OTHER INFORMATION: Description of Artificial Sequence: primer

<400> SEQUENCE: 179
caggcataga aattaactgc ggtgtctggg acagt                                35

<210> SEQ ID NO 180
<211> LENGTH: 35
<212> TYPE: DNA
<213> ORGANISM: Artificial
<220> FEATURE:
<223> OTHER INFORMATION: Description of Artificial Sequence: primer

<400> SEQUENCE: 180
agttaatttc tatgcctggg cgaggatgga ggtcg                                35

<210> SEQ ID NO 181
<211> LENGTH: 35
<212> TYPE: DNA
<213> ORGANISM: Artificial
<220> FEATURE:
<223> OTHER INFORMATION: Description of Artificial Sequence: primer

<400> SEQUENCE: 181
cgacctccat cctcgcccag gcatagaaat taact                                35

<210> SEQ ID NO 182
<211> LENGTH: 35
<212> TYPE: DNA
<213> ORGANISM: Artificial
<220> FEATURE:
<223> OTHER INFORMATION: Description of Artificial Sequence: primer

<400> SEQUENCE: 182
gctgacactt tccgcgcact cttccgagtc tactc                                35

<210> SEQ ID NO 183
<211> LENGTH: 35
<212> TYPE: DNA
<213> ORGANISM: Artificial
<220> FEATURE:
<223> OTHER INFORMATION: Description of Artificial Sequence: primer

<400> SEQUENCE: 183
gagtagactc ggaagagtgc gcggaaagtg tcagc                                      35

<210> SEQ ID NO 184
<211> LENGTH: 33
<212> TYPE: DNA
<213> ORGANISM: Artificial
<220> FEATURE:
<223> OTHER INFORMATION: Description of Artificial Sequence: primer

<400> SEQUENCE: 184
tgcagctgca tgtggatgca gccgtcagtg gcc                                        33

<210> SEQ ID NO 185
<211> LENGTH: 33
<212> TYPE: DNA
<213> ORGANISM: Artificial
<220> FEATURE:
<223> OTHER INFORMATION: Description of Artificial Sequence: primer

<400> SEQUENCE: 185
ggccactgac ggctgcatcc acatgcagct gca                                        33

<210> SEQ ID NO 186
<211> LENGTH: 33
<212> TYPE: DNA
<213> ORGANISM: Artificial
<220> FEATURE:
<223> OTHER INFORMATION: Description of Artificial Sequence: primer

<400> SEQUENCE: 186
atttcctccg gggagcgctg aagctgtaca cag                                        33

<210> SEQ ID NO 187
<211> LENGTH: 33
<212> TYPE: DNA
<213> ORGANISM: Artificial
<220> FEATURE:
<223> OTHER INFORMATION: Description of Artificial Sequence: primer

<400> SEQUENCE: 187
ctgtgtacag cttcagcgct ccccggagga aat                                        33

<210> SEQ ID NO 188
<211> LENGTH: 35
<212> TYPE: DNA
<213> ORGANISM: Artificial
<220> FEATURE:
<223> OTHER INFORMATION: Description of Artificial Sequence: primer

<400> SEQUENCE: 188
actgtcccag acaccgcagt taatttctat gcctg                                      35

<210> SEQ ID NO 189
<211> LENGTH: 35
<212> TYPE: DNA
<213> ORGANISM: Artificial
<220> FEATURE:
<223> OTHER INFORMATION: Description of Artificial Sequence: primer

<400> SEQUENCE: 189
caggcataga aattaactgc ggtgtctggg acagt                                      35

<210> SEQ ID NO 190
<211> LENGTH: 35

```
<212> TYPE: DNA
<213> ORGANISM: Artificial
<220> FEATURE:
<223> OTHER INFORMATION: Description of Artificial Sequence: primer

<400> SEQUENCE: 190
agttaatttc tatgcctggg cgaggatgga ggtcg                                35

<210> SEQ ID NO 191
<211> LENGTH: 35
<212> TYPE: DNA
<213> ORGANISM: Artificial
<220> FEATURE:
<223> OTHER INFORMATION: Description of Artificial Sequence: primer

<400> SEQUENCE: 191
cgacctccat cctcgcccag gcatagaaat taact                                35

<210> SEQ ID NO 192
<211> LENGTH: 35
<212> TYPE: DNA
<213> ORGANISM: Artificial
<220> FEATURE:
<223> OTHER INFORMATION: Description of Artificial Sequence: primer

<400> SEQUENCE: 192
gctgacactt tccgcgcact cttccgagtc tactc                                35

<210> SEQ ID NO 193
<211> LENGTH: 35
<212> TYPE: DNA
<213> ORGANISM: Artificial
<220> FEATURE:
<223> OTHER INFORMATION: Description of Artificial Sequence: primer

<400> SEQUENCE: 193
gagtagactc ggaagagtgc gcggaaagtg tcagc                                35

<210> SEQ ID NO 194
<211> LENGTH: 32
<212> TYPE: DNA
<213> ORGANISM: Artificial
<220> FEATURE:
<223> OTHER INFORMATION: Description of Artificial Sequence: primer

<400> SEQUENCE: 194
ctccggggag cgctggcgct gtacacaggg ga                                   32

<210> SEQ ID NO 195
<211> LENGTH: 32
<212> TYPE: DNA
<213> ORGANISM: Artificial
<220> FEATURE:
<223> OTHER INFORMATION: Description of Artificial Sequence: primer

<400> SEQUENCE: 195 tccectgtgt acagcgccag cgctccccgg ag                                   32

<210> SEQ ID NO 196
<211> LENGTH: 31
<212> TYPE: DNA
<213> ORGANISM: Artificial
<220> FEATURE:
<223> OTHER INFORMATION: Description of Artificial Sequence: primer

<400> SEQUENCE: 196
```
caaggaggcc gagaaaatca cgacgggctg t                                    31

<210> SEQ ID NO 197
<211> LENGTH: 31
<212> TYPE: DNA
<213> ORGANISM: Artificial
<220> FEATURE:
<223> OTHER INFORMATION: Description of Artificial Sequence: primer

<400> SEQUENCE: 197
acagcccgtc gtgatttct cggcctcctt g                                     31

<210> SEQ ID NO 198
<211> LENGTH: 37
<212> TYPE: DNA
<213> ORGANISM: Artificial
<220> FEATURE:
<223> OTHER INFORMATION: Description of Artificial Sequence: primer

<400> SEQUENCE: 198
actgcagctt gaatgagaaa atcactgtcc cagacac                              37

<210> SEQ ID NO 199
<211> LENGTH: 37
<212> TYPE: DNA
<213> ORGANISM: Artificial
<220> FEATURE:
<223> OTHER INFORMATION: Description of Artificial Sequence: primer

<400> SEQUENCE: 199
gtgtctggga cagtgatttt ctcattcaag ctgcagt                              37

<210> SEQ ID NO 200
<211> LENGTH: 31
<212> TYPE: DNA
<213> ORGANISM: Artificial
<220> FEATURE:
<223> OTHER INFORMATION: Description of Artificial Sequence: primer

<400> SEQUENCE: 200
aggccctgtt ggtcaaatct tcccagccgt g                                    31

<210> SEQ ID NO 201
<211> LENGTH: 31
<212> TYPE: DNA
<213> ORGANISM: Artificial
<220> FEATURE:
<223> OTHER INFORMATION: Description of Artificial Sequence: primer

<400> SEQUENCE: 201
cacggctggg aagatttgac caacagggcc t                                    31

<210> SEQ ID NO 202
<211> LENGTH: 33
<212> TYPE: DNA
<213> ORGANISM: Artificial
<220> FEATURE:
<223> OTHER INFORMATION: Description of Artificial Sequence: primer

<400> SEQUENCE: 202
atttcctccg gggatggctg aagctgtaca cag                                  33

<210> SEQ ID NO 203
<211> LENGTH: 33
<212> TYPE: DNA
<213> ORGANISM: Artificial

```
<220> FEATURE:
<223> OTHER INFORMATION: Description of Artificial Sequence: primer

<400> SEQUENCE: 203
ctgtgtacag cttcagccat ccccggagga aat                                    33

<210> SEQ ID NO 204
<211> LENGTH: 35
<212> TYPE: DNA
<213> ORGANISM: Artificial
<220> FEATURE:
<223> OTHER INFORMATION: Description of Artificial Sequence: primer

<400> SEQUENCE: 204
agccgagtcc tggaggcggc cctcttggag gccaa                                  35

<210> SEQ ID NO 205
<211> LENGTH: 35
<212> TYPE: DNA
<213> ORGANISM: Artificial
<220> FEATURE:
<223> OTHER INFORMATION: Description of Artificial Sequence: primer

<400> SEQUENCE: 205
ttggcctcca agagggccgc ctccaggact cggct                                  35

<210> SEQ ID NO 206
<211> LENGTH: 35
<212> TYPE: DNA
<213> ORGANISM: Artificial
<220> FEATURE:
<223> OTHER INFORMATION: Description of Artificial Sequence: primer

<400> SEQUENCE: 206
agccgagtcc tggagagggc cctcttggag gccaa                                  35

<210> SEQ ID NO 207
<211> LENGTH: 35
<212> TYPE: DNA
<213> ORGANISM: Artificial
<220> FEATURE:
<223> OTHER INFORMATION: Description of Artificial Sequence: primer

<400> SEQUENCE: 207
ttggcctcca agagggccct ctccaggact cggct                                  35

<210> SEQ ID NO 208
<211> LENGTH: 6059
<212> TYPE: DNA
<213> ORGANISM: Artificial
<220> FEATURE:
<223> OTHER INFORMATION: Description of Artificial Sequence: plasmid

<400> SEQUENCE: 208
ctagagtcga cccgggcggc cgcttccctt tagtgagggt taatgcttcg agcagacatg     60
ataagataca ttgatgagtt tggacaaacc acaactagaa tgcagtgaaa aaaatgcttt    120
atttgtgaaa tttgtgatgc tattgcttta tttgtaacca ttataagctg caataaacaa    180
gttaacaaca acaattgcat tcattttatg tttcaggttc aggggagat gtgggaggtt    240 ttttaaagca agtaaaacct ctacaaatgt ggtaaaatcc gataaggatc gatccgggct    300
ggcgtaatag cgaagaggcc cgcaccgatc gcccttccca acagttgcgc agcctgaatg    360
gcgaatggac gcgccctgta gcggcgcatt aagcgcggcg ggtgtggtgg ttacgcgcag    420
```

```
cgtgaccgct acacttgcca gcgccctagc gcccgctcct ttcgctttct tcccttcctt     480
tctcgccacg ttcgccggct ttccccgtca agctctaaat cggggggctcc ctttagggtt    540 ccgatttagt gctttacggc acctcgaccc caaaaaactt gattagggtg atggttcacg    600
tagtgggcca tcgccctgat agacggtttt tcgccctttg acgttggagt ccacgttctt    660
taatagtgga ctcttgttcc aaactggaac aacactcaac cctatctcgg tctattcttt    720
tgatttataa gggattttgc cgatttcggc ctattggtta aaaatgagc tgatttaaca     780 aaaatttaac gcgaatttta acaaaatatt aacgcttaca atttcctgat gcggtatttt    840
ctccttacgc atctgtgcgg tatttcacac cgcatacgcg gatctgcgca gcaccatggc    900
ctgaaataac ctctgaaaga ggaacttggt taggtacctt ctgaggcgga agaaccagc     960 tgtggaatgt gtgtcagtta gggtgtggaa agtccccagg ctccccagca ggcagaagta    1020
tgcaaagcat gcatctcaat tagtcagcaa ccaggtgtgg aaagtcccca ggctccccag    1080
caggcagaag tatgcaaagc atgcatctca attagtcagc aaccatagtc ccgcccctaa    1140
ctccgcccat cccgccccta actccgccca gttccgccca ttctccgccc catggctgac    1200 taatttttttt tatttatgca gaggccgagg ccgcctcggc ctctgagcta ttccagaagt   1260
agtgaggagg ctttttttgga ggcctaggct tttgcaaaaa gcttgattct tctgacacaa   1320
cagtctcgaa cttaaggcta gagccaccat gattgaacaa gatggattgc acgcaggttc    1380
tccggccgct tgggtggaga ggctattcgg ctatgactgg gcacaacaga caatcggctg    1440
ctctgatgcc gccgtgttcc ggctgtcagc gcagggggcgc ccggttcttt ttgtcaagac   1500
cgacctgtcc ggtgccctga atgaactgca ggacgaggca gcgcggctat cgtggctggc   1560
cacgacgggg gttccttgcg cagctgtgct cgacgttgtc actgaagcgg gaagggactg   1620
gctgctattg ggcgaagtgc cggggcagga tctcctgtca tctcaccttg ctcctgccga   1680
gaaagtatcc atcatggctg atgcaatgcg gcggctgcat acgcttgatc cggctacctg   1740
cccattcgac caccaagcga aacatcgcat cgagcgagca cgtactcgga tggaagccgg   1800
tcttgtcgat caggatgatc tggacgaaga gcatcagggg ctcgcgccag ccgaactgtt   1860
cgccaggctc aaggcgcgca tgcccgacgg cgaggatctc gtcgtgaccc atggcgatgc   1920
ctgcttgccg aatatcatgg tggaaaatgg ccgcttttct ggattcatcg actgtggccg   1980
gctgggtgtg gcggaccgct atcaggacat agcgttggct acccgtgata ttgctgaaga   2040
gcttggcggc gaatgggctg accgcttcct cgtgctttac ggtatcgccg ctcccgattc   2100
gcagcgcatc gccttctatc gccttcttga cgagttcttc tgagcgggac tctggggttc   2160
gaaatgaccg accaagcgac gcccaacctg ccatcacgat ggccgcaata aaatatcttt   2220
attttcatta catctgtgtg ttggttttttt gtgtgaatcg atagcgataa ggatccgcgt   2280
atggtgcact ctcagtacaa tctgctctga tgccgcatag ttaagccagc ccgacaccc    2340 gccaacaccc gctgacgcgc cctgacgggc ttgtctgctc ccggcatccg cttacagaca    2400
agctgtgacc gtctccggga gctgcatgtg tcagaggttt tcaccgtcat caccgaaacg    2460
cgcgagcgaa agggcctcg tgatacgcct atttttatag gttaatgtca tgataataat    2520
ggtttcttag acgtcaggtg gcacttttcg gggaaatgtg cgcggaaccc ctatttgttt    2580
atttttctaa atacattcaa atatgtatcc gctcatgaga caataaccct gataaatgct    2640
tcaataatat tgaaaaagga agagtatgag tattcaacat ttccgtgtcg cccttattcc    2700
cttttttgcg gcattttgcc ttcctgtttt tgctcaccca gaaacgctgg tgaaagtaaa    2760
agatgctgaa gatcagttgg gtgcacgagt gggttacatc gaactggatc tcaacagcgg    2820
```

```
taagatcctt gagagttttc gccccgaaga acgttttcca atgatgagca cttttaaagt    2880
tctgctatgt ggcgcggtat tatcccgtat tgacgccggg caagagcaac tcggtcgccg    2940
catacactat tctcagaatg acttggttga gtactcacca gtcacagaaa agcatcttac    3000
ggatggcatg acagtaagag aattatgcag tgctgccata accatgagtg ataacactgc    3060
ggccaactta cttctgacaa cgatcggagg accgaaggag ctaaccgctt ttttgcacaa    3120
catgggggat catgtaactc gccttgatcg ttgggaaccg gagctgaatg aagccatacc    3180
aaacgacgag cgtgacacca cgatgcctgt agcaatggca acaacgttgc gcaaactatt    3240
aactggcgaa ctacttactc tagcttcccg gcaacaatta atagactgga tggaggcgga    3300
taaagttgca ggaccacttc tgcgctcggc ccttccggct ggctggttta ttgctgataa    3360
atctggagcc ggtgagcgtg ggtctcgcgg tatcattgca gcactggggc cagatggtaa    3420
gccctcccgt atcgtagtta tctacacgac ggggagtcag gcaactatgg atgaacgaaa    3480
tagacagatc gctgagatag gtgcctcact gattaagcat tggtaactgt cagaccaagt    3540
ttactcatat atactttaga ttgatttaaa acttcatttt taatttaaaa ggatctaggt    3600
gaagatcctt tttgataatc tcatgaccaa aatcccttaa cgtgagtttt cgttccactg    3660
agcgtcagac cccgtagaaa agatcaaagg atcttcttga gatccttttt ttctgcgcgt    3720
aatctgctgc ttgcaaacaa aaaaaccacc gctaccagcg gtggtttgtt tgccggatca    3780
agagctacca actctttttc cgaaggtaac tggcttcagc agagcgcaga taccaaatac    3840
tgttcttcta gtgtagccgt agttaggcca ccacttcaag aactctgtag caccgcctac    3900
atacctcgct ctgctaatcc tgttaccagt ggctgctgcc agtggcgata agtcgtgtct    3960
taccgggttg gactcaagac gatagttacc ggataaggcg cagcggtcgg gctgaacggg    4020
gggttcgtgc acacagccca gcttggagcg aacgacctac accgaactga gatacctaca    4080
gcgtgagcta tgagaaagcg ccacgcttcc cgaagggaga aaggcggaca ggtatccggt    4140
aagcggcagg gtcggaacag gagagcgcac gagggagctt ccagggggaa acgcctggta    4200
tctttatagt cctgtcgggt ttcgccacct ctgacttgag cgtcgatttt tgtgatgctc    4260
gtcagggggg cggagcctat ggaaaaacgc cagcaacgcg gcctttttac ggttcctggc    4320
cttttgctgg ccttttgctc acatggctcg acagatcttc aatattggcc attagccata    4380
ttattcattg gttatatagc ataaatcaat attggctatt ggccattgca tacgttgtat    4440
ctatatcata atatgtacat ttatattggc tcatgtccaa tatgaccgcc atgttggcat    4500
tgattattga ctagttatta atagtaatca attacggggt cattagttca tagcccatat    4560
atggagttcc gcgttacata acttacggta aatggcccgc ctggctgacc gcccaacgac    4620
ccccgcccat tgacgtcaat aatgacgtat gttcccatag taacgccaat agggactttc    4680
cattgacgtc aatgggtgga gtatttacgg taaactgccc acttggcagt acatcaagtg    4740
tatcatatgc caagtccgcc ccctattgac gtcaatgacg gtaaatggcc cgcctggcat    4800
tatgcccagt acatgacctt acgggacttt cctacttggc agtacatcta cgtattagtc    4860
atcgctatta ccatggtgat gcggttttgg cagtacacca atgggcgtgg atagcggttt    4920
gactcacggg gatttccaag tctccacccc attgacgtca atgggagttt gttttggcac    4980
caaaatcaac gggactttcc aaaatgtcgt aacaactgcg atcgcccgcc ccgttgacgc    5040
aaatgggcgg taggcgtgta cggtgggagg tctatataag cagagctcgt ttagtgaacc    5100
gtcagatcac tagaagcttt attgcggtag tttatcacag ttaaattgct aacgcagtca    5160
```

```
gtgcttctga cacaacagtc tcgaacttaa gctgcagtga ctctcttaag gtagccttgc   5220
agaagttggt cgtgaggcac tgggcaggta agtatcaagg ttacaagaca ggtttaagga   5280
gaccaataga aactgggctt gtcgagacag agaagactct tgcgtttctg ataggcacct   5340
attggtctta ctgacatcca ctttgccttt ctctccacag gtgtccactc ccagttcaat   5400
tacagctctt aaggctagag tacttaatac gactcactat aggctagcct cgagcgcgga   5460 gatggggtg cacgaatgtc ctgcctggct gtggcttctc ctgtccctgc tgtcgctccc   5520
tctgggcctc ccagtcctgg gcgccccacc acgcctcatc tgtgacagcc gagtcctgga   5580
gaggtacctc ttggaggcca aggaggccga gaatatcacg acgggctgtg ctgaacactg   5640
cagcttgaat gagaatatca ctgtcccaga caccaaagtt aatttctatg cctggaagag   5700
gatggaggtc gggcagcagg ccgtagaagt ctggcagggc ctggccctgc tgtcggaagc   5760
tgtcctgcgg ggccaggccc tgttggtcaa ctcttcccag ccgtgggagc ccctgcagct   5820
gcatgtggat aaagccgtca gtggccttcg cagcctcacc actctgcttc gggctctgcg   5880
agcccagaag gaagccatct cccctccaga tgcggcctca gctgctccac tccgaacaat   5940
cactgctgac actttccgca aactcttccg agtctactcc aatttcctcc ggggaaagct   6000
gaagctgtac acaggggagg cctgcaggac agggaccat catcaccatc accattgat    6059

<210> SEQ ID NO 209
<211> LENGTH: 6059
<212> TYPE: DNA
<213> ORGANISM: Artificial
<220> FEATURE:
<223> OTHER INFORMATION: Description of Artificial Sequence: plasmid

<400> SEQUENCE: 209
ctagagtcga cccgggcggc cgcttcccct tagtgagggt taatgcttcg agcagacatg     60
ataagataca ttgatgagtt tggacaaacc acaactagaa tgcagtgaaa aaaatgcttt    120
atttgtgaaa tttgtgatgc tattgcttta tttgtaacca ttataagctg caataaacaa    180
gttaacaaca acaattgcat tcattttatg tttcaggttc aggggagat gtgggaggtt     240 ttttaaagca agtaaaacct ctacaaatgt ggtaaaatcc gataaggatc gatccgggct    300
ggcgtaatag cgaagaggcc cgcaccgatc gcccttccca cagttgcgc agcctgaatg     360 gcgaatggac gcgccctgta gcggcgcatt aagcgcggcg ggtgtggtgg ttacgcgcag    420
cgtgaccgct acacttgcca gcgccctagc gcccgctcct ttcgctttct tcccttcctt    480
tctcgccacg ttcgccggct ttccccgtca agctctaaat cggggctcc ctttagggtt     540 ccgatttagt gctttacggc acctcgaccc caaaaaactt gattagggtg atggttcacg    600
tagtgggcca tcgccctgat agacggtttt tcgccctttg acgttggagt ccacgttctt    660
taatagtgga ctcttgttcc aaactggaac aacactcaac cctatctcgg tctattcttt    720
tgatttataa gggattttgc cgatttcggc ctattggtta aaaatgagc tgatttaaca     780 aaaatttaac gcgaatttta acaaaatatt aacgcttaca atttcctgat gcggtatttt    840
ctccttacgc atctgtgcgg tatttcacac cgcatacgcg gatctgcgca gcaccatggc    900
ctgaaataac ctctgaaaga ggaacttggt taggtaccct ctgaggcgga agaaccagc     960 tgtggaatgt gtgtcagtta gggtgtggaa agtccccagg ctccccagca ggcagaagta   1020
tgcaaagcat gcatctcaat tagtcagcaa ccaggtgtgg aaagtcccca ggctccccag   1080
caggcagaag tatgcaaagc atgcatctca attagtcagc aaccatagtc ccgcccctaa   1140
ctccgcccat cccgccccta actccgccca gttccgccca ttctccgccc catggctgac   1200
```

```
taattttttt tatttatgca gaggccgagg ccgcctcggc ctctgagcta ttccagaagt    1260
agtgaggagg cttttttgga ggcctaggct tttgcaaaaa gcttgattct tctgacacaa    1320
cagtctcgaa cttaaggcta gagccaccat gattgaacaa gatggattgc acgcaggttc    1380
tccggccgct tgggtggaga ggctattcgg ctatgactgg gcacaacaga caatcggctg    1440
ctctgatgcc gccgtgttcc ggctgtcagc gcagggcgc ccggttcttt ttgtcaagac    1500
cgacctgtcc ggtgccctga tgaactgca ggacgaggca gcgcggctat cgtggctggc    1560
cacgacgggg gttccttgcg cagctgtgct cgacgttgtc actgaagcgg aagggactg    1620 gctgctattg ggcgaagtgc cggggcagga tctcctgtca tctcaccttg ctcctgccga    1680
gaaagtatcc atcatggctg atgcaatgcg gcggctgcat acgcttgatc cggctacctg    1740
cccattcgac caccaagcga aacatcgcat cgagcgagca cgtactcgga tggaagccgg    1800
tcttgtcgat caggatgatc tggacgaaga gcatcagggg ctcgcgccag ccgaactgtt    1860
cgccaggctc aaggcgcgca tgcccgacgg cgaggatctc gtcgtgaccc atggcgatgc    1920
ctgcttgccg aatatcatgg tggaaaatgg ccgcttttct ggattcatcg actgtggccg    1980
gctgggtgtg gcggaccgct atcaggacat agcgttggct acccgtgata ttgctgaaga    2040
gcttggcggc gaatgggctg accgcttcct cgtgctttac ggtatcgccg ctcccgattc    2100
gcagcgcatc gccttctatc gccttcttga cgagttcttc tgagcgggac tctggggttc    2160
gaaatgaccg accaagcgac gcccaacctg ccatcacgat ggccgcaata aaatatcttt    2220
attttcatta catctgtgtg ttggttttt gtgtgaatcg atagcgataa ggatccgcgt    2280
atggtgcact ctcagtacaa tctgctctga tgccgcatag ttaagccagc cccgacaccc    2340
gccaacaccc gctgacgcgc cctgacgggc ttgtctgctc ccggcatccg cttacagaca    2400
agctgtgacc gtctccggga gctgcatgtg tcagaggttt tcaccgtcat caccgaaacg    2460
cgcgagacga aagggcctcg tgatacgcct atttttatag gttaatgtca tgataataat    2520
ggtttcttag acgtcaggtg gcacttttcg gggaaatgtg cgcggaaccc ctatttgttt    2580 attttctaa atacattcaa atatgtatcc gctcatgaga caataaccct gataaatgct    2640
tcaataatat tgaaaaagga agagtatgag tattcaacat ttccgtgtcg cccttattcc    2700
cttttttgcg gcattttgcc ttcctgtttt tgctcaccca gaaacgctgg tgaaagtaaa    2760
agatgctgaa gatcagttgg gtgcacgagt gggttacatc gaactggatc tcaacagcgg    2820
taagatcctt gagagttttc gccccgaaga acgttttcca atgatgagca cttttaaagt    2880
tctgctatgt ggcgcggtat tatcccgtat tgacgccggg caagagcaac tcggtcgccg    2940
catacactat tctcagaatg acttggttga gtactcacca gtcacagaaa agcatcttac    3000
ggatggcatg acagtaagag aattatgcag tgctgccata accatgagtg ataacactgc    3060
ggccaactta cttctgacaa cgatcggagg accgaaggag ctaaccgctt ttttgcacaa    3120
catgggggat catgtaactc gccttgatcg ttgggaaccg gagctgaatg aagccatacc    3180
aaacgacgag cgtgacacca cgatgcctgt agcaatggca acaacgttgc gcaaactatt    3240
aactggcgaa ctacttactc tagcttcccg gcaacaatta atagactgga tggaggcgga    3300
taaagttgca ggaccacttc tgcgctcggc ccttccggct ggctggttta ttgctgataa    3360
atctggagcc ggtgagcgtg ggtctcgcgg tatcattgca gcactgggc cagatggtaa    3420 gccctcccgt atcgtagtta tctacacgac ggggagtcag gcaactatgg atgaacgaaa    3480
tagacagatc gctgagatag gtgcctcact gattaagcat tggtaactgt cagaccaagt    3540
```

```
ttactcatat atactttaga ttgatttaaa acttcatttt taatttaaaa ggatctaggt    3600
gaagatcctt tttgataatc tcatgaccaa aatcccttaa cgtgagtttt cgttccactg    3660
agcgtcagac cccgtagaaa agatcaaagg atcttcttga gatccttttt ttctgcgcgt    3720
aatctgctgc ttgcaaacaa aaaaaccacc gctaccagcg gtggtttgtt tgccggatca    3780
agagctacca actcttttc cgaaggtaac tggcttcagc agagcgcaga taccaaatac    3840
tgttcttcta gtgtagccgt agttaggcca ccacttcaag aactctgtag caccgcctac    3900
atacctcgct ctgctaatcc tgttaccagt ggctgctgcc agtggcgata agtcgtgtct    3960
taccgggttg gactcaagac gatagttacc ggataaggcg cagcggtcgg gctgaacggg    4020
gggttcgtgc acacagccca gcttggagcg aacgacctac accgaactga gatacctaca    4080
gcgtgagcta tgagaaagcg ccacgcttcc cgaagggaga aaggcggaca ggtatccggt    4140
aagcggcagg gtcggaacag gagagcgcac gagggagctt ccaggggaa acgcctggta    4200 tctttatagt cctgtcgggt ttcgccacct ctgacttgag cgtcgatttt tgtgatgctc    4260
gtcagggggg cggagcctat ggaaaaacgc cagcaacgcg gcctttttac ggttcctggc    4320
cttttgctgg ccttttgctc acatggctcg acagatcttc aatattggcc attagccata    4380
ttattcattg gttatatagc ataaatcaat attggctatt ggccattgca tacgttgtat    4440
ctatatcata atatgtacat ttatattggc tcatgtccaa tatgaccgcc atgttggcat    4500
tgattattga ctagttatta atagtaatca attacggggt cattagttca tagcccatat    4560
atggagttcc gcgttacata acttacggta atggcccgc ctggctgacc gcccaacgac    4620
ccccgcccat tgacgtcaat aatgacgtat gttcccatag taacgccaat agggactttc    4680
cattgacgtc aatgggtgga gtatttacgg taaactgccc acttggcagt acatcaagtg    4740
tatcatatgc caagtccgcc ccctattgac gtcaatgacg gtaaatggcc cgcctggcat    4800
tatgcccagt acatgacctt acgggacttt cctacttggc agtacatcta cgtattagtc    4860
atcgctatta ccatggtgat gcggttttgg cagtacacca tgggcgtgg atagcggttt    4920 gactcacggg gatttccaag tctccacccc attgacgtca atgggagttt gttttggcac    4980
caaaatcaac gggactttcc aaaatgtcgt aacaactgcg atcgccgcc ccgttgacgc    5040 aaatgggcgg taggcgtgta cggtgggagg tctatataag cagagctcgt ttagtgaacc    5100
gtcagatcac tagaagcttt attgcggtag tttatcacag ttaaattgct aacgcagtca    5160
gtgcttctga cacaacagtc tcgaacttaa gctgcagtga ctctcttaag gtagccttgc    5220
agaagttggt cgtgaggcac tgggcaggta agtatcaagg ttacaagaca ggtttaagga    5280
gaccaataga aactgggctt gtcgagacag agaagactct tgcgtttctg ataggcacct    5340
attggtctta ctgacatcca ctttgccttt ctctccacag gtgtccactc ccagttcaat    5400
tacagctctt aaggctagag tacttaatac gactcactat aggctagcct cgagcgcgga    5460 gatggggtg cacgaatgtc ctgcctggct gtggcttctc ctgtccctgc tgtcgctccc    5520
tctgggcctc ccagtcctgg gcgccccacc acgcctcatc tgtgacagcc gagtcctgga    5580
gaggtacctc ttggaggcca aggaggccga gaatatcacg acgggctgta atgaaacctg    5640
cagcttgaat gagaatatca ctgtcccaga caccaaagtt aatttctatg cctggaagag    5700
gatggaggtc gggcagcagg ccgtagaagt ctggcagggc ctggcctgc tgtcggaagc    5760 tgtcctgcgg ggccaggccc tgttggtcaa ctcttcccag ccgtgggagc cctgcagct    5820 gcatgtggat aaagcgtca gtggccttcg cagcctcacc actctgcttc gggtctgcg    5880 agcccagaag gaagccatct cccctccaga tgcggcctca gctgctccac tccgaacaat    5940
```

| cactgctgac actttccgca aactcttccg agtctactcc aatttcctcc ggggaaagct | 6000 |
| gaagctgtac acaggggagg cctgcaggac aggggaccat catcaccatc accattgat | 6059 |

<210> SEQ ID NO 210
<211> LENGTH: 6059
<212> TYPE: DNA
<213> ORGANISM: Artificial
<220> FEATURE:
<223> OTHER INFORMATION: Description of Artificial Sequence: plasmid

<400> SEQUENCE: 210

| ctagagtcga cccgggcggc cgcttccctt tagtgagggt taatgcttcg agcagacatg | 60 |
| ataagataca ttgatgagtt tggacaaacc acaactagaa tgcagtgaaa aaatgcttt | 120 |
| atttgtgaaa tttgtgatgc tattgcttta tttgtaacca ttataagctg caataaacaa | 180 |
| gttaacaaca acaattgcat tcattttatg tttcaggttc agggggagat gtgggaggtt | 240 |
| ttttaaagca agtaaaacct ctacaaatgt ggtaaaatcc gataaggatc gatccgggct | 300 |
| ggcgtaatag cgaagaggcc cgcaccgatc gcccttccca cagttgcgc agcctgaatg | 360 |
| gcgaatggac gcgccctgta gcggcgcatt aagcgcggcg ggtgtggtgg ttacgcgcag | 420 |
| cgtgaccgct acacttgcca gcgccctagc gcccgctcct ttcgctttct tcccttcctt | 480 |
| tctcgccacg ttcgccggct ttccccgtca gctctaaat cggggctcc ctttaggtt | 540 |
| ccgatttagt gctttacggc acctcgaccc caaaaaactt gattagggtg atggttcacg | 600 |
| tagtgggcca tcgccctgat agacggtttt tcgcccttg acgttggagt ccacgttctt | 660 |
| taatagtgga ctcttgttcc aaactggaac aacactcaac cctatctcgg tctattcttt | 720 |
| tgatttataa gggattttgc cgatttcggc ctattggtta aaaaatgagc tgatttaaca | 780 |
| aaaatttaac gcgaatttta acaaaatatt aacgcttaca atttcctgat gcggtatttt | 840 |
| ctccttacgc atctgtgcgg tatttcacac cgcatacgcg gatctgcgca gcaccatggc | 900 |
| ctgaaataac ctctgaaaga ggaacttggt taggtacctt ctgaggcgga agaaccagc | 960 |
| tgtggaatgt gtgtcagtta gggtgtggaa agtccccagg ctccccagca ggcagaagta | 1020 |
| tgcaaagcat gcatctcaat tagtcagcaa ccaggtgtgg aaagtcccca ggctccccag | 1080 |
| caggcagaag tatgcaaagc atgcatctca attagtcagc aaccatagtc ccgcccctaa | 1140 |
| ctccgcccat cccgccccta actccgccca gttccgccca ttctccgccc catggctgac | 1200 |
| taatttttt tatttatgca gaggccgagg ccgcctcggc ctctgagcta ttccagaagt | 1260 |
| agtgaggagg cttttttgga ggcctaggct tttgcaaaaa gcttgattct tctgacacaa | 1320 |
| cagtctcgaa cttaaggcta gagccaccat gattgaacaa gatggattgc acgcaggttc | 1380 |
| tccggccgct tgggtggaga ggctattcgg ctatgactgg gcacaacaga atcggctg | 1440 |
| ctctgatgcc gccgtgttcc ggctgtcagc gcagggggc ccggttcttt ttgtcaagac | 1500 |
| cgacctgtcc ggtgccctga tgaactgca ggacgaggca gcgcggctat cgtggctggc | 1560 |
| cacgacgggc gttccttgcg cagctgtgct cgacgttgtc actgaagcgg gaagggactg | 1620 |
| gctgctattg ggcgaagtgc cggggcagga tctcctgtca tctcaccttg ctcctgccga | 1680 |
| gaaagtatcc atcatggctg atgcaatgcg gcggctgcat acgcttgatc cggctacctg | 1740 |
| cccattcgac caccaagcga aacatcgcat cgagcgagca cgtactcgga tggaagccgg | 1800 |
| tcttgtcgat caggatgatc tggacgaaga gcatcagggg ctcgcgccag ccgaactgtt | 1860 |
| cgccaggctc aaggcgcgca tgcccgacgg cgaggatctc gtcgtgaccc atggcgatgc | 1920 |

```
ctgcttgccg aatatcatgg tggaaaatgg ccgcttttct ggattcatcg actgtggccg   1980
gctgggtgtg gcggaccgct atcaggacat agcgttggct acccgtgata ttgctgaaga   2040
gcttggcggc gaatgggctg accgcttcct cgtgctttac ggtatcgccg ctcccgattc   2100
gcagcgcatc gccttctatc gccttcttga cgagttcttc tgagcgggac tctggggttc   2160
gaaatgaccg accaagcgac gcccaacctg ccatcacgat ggccgcaata aaatatcttt   2220
attttcatta catctgtgtg ttggtttttt gtgtgaatcg atagcgataa ggatccgcgt   2280
atggtgcact ctcagtacaa tctgctctga tgccgcatag ttaagccagc cccgacaccc   2340
gccaacaccc gctgacgcgc cctgacgggc ttgtctgctc ccggcatccg cttacagaca   2400
agctgtgacc gtctccggga gctgcatgtg tcagaggttt tcaccgtcat caccgaaacg   2460
cgcgagacga aagggcctcg tgatacgcct attttatag gttaatgtca tgataataat   2520
ggtttcttag acgtcaggtg gcacttttcg gggaaatgtg cgcggaaccc ctatttgttt   2580
atttttctaa atacattcaa atatgtatcc gctcatgaga caataaccct gataaatgct   2640
tcaataatat tgaaaaagga gagtatgag tattcaacat ttccgtgtcg cccttattcc   2700
cttttttgcg gcattttgcc ttcctgtttt tgctcaccca gaaacgctgg tgaaagtaaa   2760
agatgctgaa gatcagttgg gtgcacgagt gggttacatc gaactggatc tcaacagcgg   2820
taagatcctt gagagttttc gccccgaaga acgttttcca atgatgagca cttttaaagt   2880
tctgctatgt ggcgcggtat tatcccgtat tgacgccggg caagagcaac tcggtcgccg   2940
catacactat tctcagaatg acttggttga gtactcacca gtcacagaaa agcatcttac   3000
ggatggcatg acagtaagag aattatgcag tgctgccata accatgagtg ataacactgc   3060
ggccaactta cttctgacaa cgatcggagg accgaaggag ctaaccgctt ttttgcacaa   3120
catgggggat catgtaactc gccttgatcg ttgggaaccg gagctgaatg aagccatacc   3180
aaacgacgag cgtgacacca cgatgcctgt agcaatggca acaacgttgc gcaaactatt   3240
aactggcgaa ctacttactc tagcttcccg gcaacaatta atagactgga tggaggcgga   3300
taaagttgca ggaccacttc tgcgctcggc ccttccggct ggctggttta ttgctgataa   3360
atctggagcc ggtgagcgtg gtctcgcgg tatcattgca gcactggggc cagatggtaa   3420
gccctcccgt atcgtagtta tctacacgac ggggagtcag gcaactatgg atgaacgaaa   3480
tagacagatc gctgagatag gtgcctcact gattaagcat tggtaactgt cagaccaagt   3540
ttactcatat atactttaga ttgatttaaa acttcatttt taatttaaaa ggatctaggt   3600
gaagatcctt tttgataatc tcatgaccaa atcccttaa cgtgagtttt cgttccactg   3660
agcgtcagac cccgtagaaa agatcaaagg atcttcttga gatcctttt ttctgcgcgt   3720
aatctgctgc ttgcaaacaa aaaaaccacc gctaccagcg gtggtttgtt tgccggatca   3780
agagctacca actctttttc cgaaggtaac tggcttcagc agagcgcaga taccaaatac   3840
tgttcttcta gtgtagccgt agttaggcca ccacttcaag aactctgtag caccgcctac   3900
atacctcgct ctgctaatcc tgttaccagt ggctgctgcc agtggcgata agtcgtgtct   3960
taccgggttg gactcaagac gatagttacc ggataaggcg cagcggtcgg gctgaacggg   4020
gggttcgtgc acacagccca gcttggagcg aacgacctac accgaactga gatacctaca   4080
gcgtgagcta tgagaaagcg ccacgcttcc cgaagggaga aaggcggaca ggtatccggt   4140
aagcggcagg gtcggaacag gagagcgcac gagggagctt ccagggggaa acgcctggta   4200
tctttatagt cctgtcgggt ttcgccacct ctgacttgag cgtcgatttt tgtgatgctc   4260
gtcagggggg cggagcctat ggaaaaacgc cagcaacgcg gcctttttac ggttcctggc   4320
```

```
cttttgctgg ccttttgctc acatggctcg acagatcttc aatattggcc attagccata    4380
ttattcattg gttatatagc ataaatcaat attggctatt ggccattgca tacgttgtat    4440
ctatatcata atatgtacat ttatattggc tcatgtccaa tatgaccgcc atgttggcat    4500
tgattattga ctagttatta atagtaatca attacggggt cattagttca tagcccatat    4560
atggagttcc gcgttacata acttacggta atggcccgc ctggctgacc gcccaacgac    4620
ccccgcccat tgacgtcaat aatgacgtat gttcccatag taacgccaat agggactttc    4680
cattgacgtc aatgggtgga gtatttacgg taaactgccc acttggcagt acatcaagtg    4740
tatcatatgc caagtccgcc ccctattgac gtcaatgacg gtaaatggcc cgcctggcat    4800
tatgcccagt acatgacctt acgggacttt cctacttggc agtacatcta cgtattagtc    4860
atcgctatta ccatggtgat gcggttttgg cagtacacca tgggcgtgg atagcggttt    4920 gactcacggg gatttccaag tctccacccc attgacgtca atgggagttt gttttggcac    4980
caaaatcaac gggactttcc aaaatgtcgt aacaactgcg atcgcccgcc ccgttgacgc    5040
aaatgggcgg taggcgtgta cggtgggagg tctatataag cagagctcgt ttagtgaacc    5100
gtcagatcac tagaagcttt attgcggtag tttatcacag ttaaattgct aacgcagtca    5160
gtgcttctga cacaacagtc tcgaacttaa gctgcagtga ctctcttaag gtagccttgc    5220
agaagttggt cgtgaggcac tgggcaggta agtatcaagg ttacaagaca ggtttaagga    5280
gaccaataga aactgggctt gtcgagacag agaagactct tgcgtttctg ataggcacct    5340
attggtctta ctgacatcca ctttgccttt ctctccacag gtgtccactc ccagttcaat    5400
tacagctctt aaggctagag tacttaatac gactcactat aggctagcct cgagcgcgga    5460
gatgggggtg cacgaatgtc ctgcctggct gtggcttctc ctgtccctgc tgtcgctccc    5520
tctgggcctc ccagtcctgg gcgccccacc acgcctcatc tgtgacagcc gagtcctgga    5580
gaggtacctc ttggaggcca aggaggccga gaatatcacg acgggctgtg ctgaacactg    5640
cagcttgaat gagaatatca ctgtcccaga caccgacgtt aatttctatg cctggaagag    5700
gatggaggtc gggcagcagg ccgtagaagt ctggcagggc ctggccctgc tgtcggaagc    5760
tgtcctgcgg ggccaggccc tgttggtcaa ctcttcccag ccgtgggagc ccctgcagct    5820
gcatgtggat aaagccgtca gtggccttcg cagcctcacc actctgcttc gggctctgcg    5880
agcccagaag gaagccatct cccctccaga tgcggcctca gctgctccac tccgaacaat    5940
cactgctgac actttccgca aactcttccg agtctactcc aatttcctcc ggggaaagct    6000
gaagctgtac acaggggagg cctgcaggac agggaccat catcaccatc accattgat    6059
```

<210> SEQ ID NO 211
<211> LENGTH: 6059
<212> TYPE: DNA
<213> ORGANISM: Artificial
<220> FEATURE:
<223> OTHER INFORMATION: Description of Artificial Sequence: plasmid

<400> SEQUENCE: 211

```
ctagagtcga cccgggcggc cgcttccctt tagtgagggt taatgcttcg agcagacatg     60
ataagataca ttgatgagtt tggacaaacc acaactagaa tgcagtgaaa aaaatgcttt    120
atttgtgaaa tttgtgatgc tattgcttta tttgtaacca ttataagctg caataaacaa    180
gttaacaaca acaattgcat tcattttatg tttcaggttc agggggagat gtgggaggtt    240
ttttaaagca agtaaaacct ctacaaatgt ggtaaaatcc gataaggatc gatccgggct    300
```

-continued

```
ggcgtaatag cgaagaggcc cgcaccgatc gcccttccca acagttgcgc agcctgaatg      360
gcgaatggac gcgccctgta gcggcgcatt aagcgcggcg ggtgtggtgg ttacgcgcag      420
cgtgaccgct acacttgcca gcgccctagc gcccgctcct ttcgctttct tcccttcctt      480
tctcgccacg ttcgccggct ttccccgtca agctctaaat cggggctcc ctttagggtt       540
ccgatttagt gctttacggc acctcgaccc caaaaaactt gattagggtg atggttcacg      600
tagtgggcca tcgccctgat agacggtttt tcgccctttg acgttggagt ccacgttctt      660
taatagtgga ctcttgttcc aaactggaac aacactcaac cctatctcgg tctattcttt      720
tgatttataa gggattttgc cgatttcggc ctattggtta aaaaatgagc tgatttaaca      780
aaaatttaac gcgaatttta acaaaatatt aacgcttaca atttcctgat gcggtatttt      840
ctccttacgc atctgtgcgg tatttcacac cgcatacgcg gatctgcgca gcaccatggc      900
ctgaaataac ctctgaaaga ggaacttggt taggtacctt ctgaggcgga agaaccagc       960
tgtggaatgt gtgtcagtta gggtgtggaa agtccccagg ctccccagca ggcagaagta     1020
tgcaaagcat gcatctcaat tagtcagcaa ccaggtgtgg aaagtcccca ggctccccag     1080
caggcagaag tatgcaaagc atgcatctca attagtcagc aaccatagtc ccgcccctaa     1140
ctccgcccat cccgcccta actccgccca gttccgccca ttctccgccc catggctgac      1200
taatttttt tatttatgca gaggccgagg ccgcctcggc ctctgagcta ttccagaagt      1260
agtgaggagg ctttttgga ggcctaggct tttgcaaaaa gcttgattct tctgacacaa      1320
cagtctcgaa cttaaggcta gagccaccat gattgaacaa gatggattgc acgcaggttc     1380
tccggccgct tgggtggaga ggctattcgg ctatgactgg gcacaacaga caatcggctg     1440
ctctgatgcc gccgtgttcc ggctgtcagc gcaggggcgc ccggttcttt ttgtcaagac     1500
cgacctgtcc ggtgccctga atgaactgca ggacgaggca gcgcggctat cgtggctggc     1560
cacgacgggc gttccttgcg cagctgtgct cgacgttgtc actgaagcgg gaagggactg     1620
gctgctattg ggcgaagtgc cggggcagga tctcctgtca tctcaccttg ctcctgccga     1680
gaaagtatcc atcatggctg atgcaatgcg gcggctgcat acgcttgatc cggctacctg     1740
cccattcgac caccaagcga aacatcgcat cgagcgagca cgtactcgga tggaagccgg     1800
tcttgtcgat caggatgatc tggacgaaga gcatcagggg ctcgcgccag ccgaactgtt     1860
cgccaggctc aaggcgcgca tgcccgacgg cgaggatctc gtcgtgaccc atggcgatgc     1920
ctgcttgccg aatatcatgg tggaaaatgg ccgcttttct ggattcatcg actgtggccg     1980
gctgggtgtg gcggaccgct atcaggacat agcgttggct acccgtgata ttgctgaaga     2040
gcttggcggc gaatgggctg accgcttcct cgtgctttac ggtatcgccg ctcccgattc     2100
gcagcgcatc gccttctatc gccttcttga cgagttcttc tgagcgggac tctgggttc     2160
gaaatgaccg accaagcgac gcccaacctg ccatcacgat ggccgcaata aaatatcttt     2220
attttcatta catctgtgtg ttggtttttt gtgtgaatcg atagcgataa ggatccgcgt     2280
atggtgcact ctcagtacaa tctgctctga tgccgcatag ttaagccagc ccgacaccc      2340
gccaacaccc gctgacgcgc cctgacgggc ttgtctgctc ccggcatccg cttacagaca     2400
agctgtgacc gtctccggga gctgcatgtg tcagaggttt tcaccgtcat caccgaaacg     2460
cgcgagcgga aagggcctcg tgatacgcct atttttatag gttaatgtca tgataataat     2520
ggtttcttag acgtcaggtg gcacttttcg gggaaatgtg cgcggaaccc ctatttgttt     2580
atttttctaa atacattcaa atatgtatcc gctcatgaga caataaccct gataaatgct     2640
tcaataatat tgaaaaagga agagtatgag tattcaacat ttccgtgtcg cccttattcc     2700
```

```
cttttttgcg gcattttgcc ttcctgtttt tgctcaccca gaaacgctgg tgaaagtaaa    2760
agatgctgaa gatcagttgg gtgcacgagt gggttacatc gaactggatc tcaacagcgg    2820
taagatcctt gagagttttc gccccgaaga acgttttcca atgatgagca cttttaaagt    2880
tctgctatgt ggcgcggtat tatcccgtat tgacgccggg caagagcaac tcggtcgccg    2940
catacactat tctcagaatg acttggttga gtactcacca gtcacagaaa agcatcttac    3000
ggatggcatg acagtaagag aattatgcag tgctgccata accatgagtg ataacactgc    3060
ggccaactta cttctgacaa cgatcggagg accgaaggag ctaaccgctt ttttgcacaa    3120
catgggggat catgtaactc gccttgatcg ttgggaaccg gagctgaatg aagccatacc    3180
aaacgacgag cgtgacacca cgatgcctgt agcaatggca acaacgttgc gcaaactatt    3240
aactggcgaa ctacttactc tagcttcccg gcaacaatta atagactgga tggaggcgga    3300
taaagttgca ggaccacttc tgcgctcggc ccttccggct ggctggttta ttgctgataa    3360
atctggagcc ggtgagcgtg gtctcgcgg tatcattgca gcactggggc cagatggtaa    3420
gccctcccgt atcgtagtta tctacacgac ggggagtcag gcaactatgg atgaacgaaa    3480
tagacagatc gctgagatag gtgcctcact gattaagcat tggtaactgt cagaccaagt    3540
ttactcatat atactttaga ttgatttaaa acttcatttt taatttaaaa ggatctaggt    3600
gaagatcctt tttgataatc tcatgaccaa aatcccttaa cgtgagtttt cgttccactg    3660
agcgtcagac cccgtagaaa agatcaaagg atcttcttga gatccttttt ttctgcgcgt    3720
aatctgctgc ttgcaaacaa aaaaaccacc gctaccagcg gtggtttgtt tgccggatca    3780
agagctacca actctttttc cgaaggtaac tggcttcagc agagcgcaga taccaaatac    3840
tgttcttcta gtgtagccgt agttaggcca ccacttcaag aactctgtag caccgcctac    3900
atacctcgct ctgctaatcc tgttaccagt ggctgctgcc agtggcgata agtcgtgtct    3960
taccgggttg gactcaagac gatagttacc ggataaggcg cagcggtcgg gctgaacggg    4020
gggttcgtgc acacagccca gcttggagcg aacgacctac accgaactga gatacctaca    4080
gcgtgagcta tgagaaagcg ccacgcttcc cgaagggaga aaggcggaca ggtatccggt    4140
aagcggcagg gtcggaacag gagagcgcac gagggagctt ccaggggaaa acgcctggta    4200
tctttatagt cctgtcgggt ttcgccacct ctgacttgag cgtcgatttt tgtgatgctc    4260
gtcagggggg cggagcctat ggaaaaacgc cagcaacgcg gcctttttac ggttcctggc    4320
cttttgctgg ccttttgctc acatggctcg acagatcttc aatattggcc attagccata    4380
ttattcattg gttatatagc ataaatcaat attggctatt ggccattgca tacgttgtat    4440
ctatatcata atatgtacat ttatattggc tcatgtccaa tatgaccgcc atgttggcat    4500
tgattattga ctagttatta atagtaatca attacggggt cattagttca tagcccatat    4560
atggagttcc gcgttacata acttacggta aatggcccgc ctggctgacc gcccaacgac    4620
ccccgcccat tgacgtcaat aatgacgtat gttcccatag taacgccaat agggactttc    4680
cattgacgtc aatgggtgga gtatttacgg taaactgccc acttggcagt acatcaagtg    4740
tatcatatgc caagtccgcc ccctattgac gtcaatgacg gtaaatggcc cgcctggcat    4800
tatgcccagt acatgacctt acgggacttt cctacttggc agtacatcta cgtattagtc    4860
atcgctatta ccatggtgat gcggttttgg cagtacacca atgggcgtgg atagcggttt    4920
gactcacggg gatttccaag tctccacccc attgacgtca atgggagttt gttttggcac    4980
caaaatcaac gggactttcc aaaatgtcgt aacaactgcg atcgcccgcc ccgttgacgc    5040
```

```
aaatgggcgg taggcgtgta cggtgggagg tctatataag cagagctcgt ttagtgaacc      5100
gtcagatcac tagaagcttt attgcggtag tttatcacag ttaaattgct aacgcagtca      5160
gtgcttctga cacaacagtc tcgaacttaa gctgcagtga ctctcttaag gtagccttgc      5220
agaagttggt cgtgaggcac tgggcaggta agtatcaagg ttacaagaca ggtttaagga      5280
gaccaataga aactgggctt gtcgagacag agaagactct tgcgtttctg ataggcacct      5340
attggtctta ctgacatcca ctttgccttt ctctccacag gtgtccactc ccagttcaat      5400
tacagctctt aaggctagag tacttaatac gactcactat aggctagcct cgagcgcgga      5460
gatgggggtg cacgaatgtc ctgcctggct gtggcttctc ctgtccctgc tgtcgctccc      5520
tctgggcctc ccagtcctgg gcgccccacc acgcctcatc tgtgacagcc gagtcctgga      5580
gaggtacctc ttggaggcca aggaggccga gaatatcacg acgggctgtg ctgaacactg      5640
cagcttgaat gagaatatca ctgtcccaga caccaaagtt aatttctatg cctggaagag      5700
gatggaggtc gggcagcagg ccgtagaagt ctggcagggc ctggccctgc tgtcggaagc      5760
tgtcctgcgg ggccaggccc tgttggtcaa ctcttcccag ccgtgggagc ccctgcagct      5820
gcatgtggat aaagccgtcg agggccttcg cagcctcacc actctgcttc gggctctgcg      5880
agcccagaag gaagccatct cccctccaga tgcggcctca gctgctccac tccgaacaat      5940
cactgctgac actttccgca aactcttccg agtctactcc aatttcctcc ggggaaagct      6000
gaagctgtac acaggggagg cctgcaggac agggaccat catcaccatc accattgat       6059
```

<210> SEQ ID NO 212
<211> LENGTH: 6059
<212> TYPE: DNA
<213> ORGANISM: Artificial
<220> FEATURE:
<223> OTHER INFORMATION: Description of Artificial Sequence: plasmid

<400> SEQUENCE: 212

```
ctagagtcga cccgggcggc cgcttccctt tagtgagggt taatgcttcg agcagacatg        60
ataagataca ttgatgagtt tggacaaacc acaactagaa tgcagtgaaa aaatgcttt       120 atttgtgaaa tttgtgatgc tattgcttta tttgtaacca ttataagctg caataaacaa      180
gttaacaaca acaattgcat tcattttatg tttcaggttc agggggagat gtgggaggtt      240
ttttaaagca agtaaaacct ctacaaatgt ggtaaaatcc gataaggatc gatccgggct      300
ggcgtaatag cgaagaggcc cgcaccgatc gcccttccca acagttgcgc agcctgaatg      360
gcgaatggac gcgccctgta gcggcgcatt aagcgcggcg ggtgtggtgg ttacgcgcag      420
cgtgaccgct acacttgcca gcgccctagc gcccgctcct ttcgctttct tcccttcctt      480
tctcgccacg ttcgccggct ttccccgtca agctctaaat cggggggctcc ctttagggtt      540 ccgatttagt gctttacggc acctcgaccc caaaaaactt gattagggtg atggttcacg      600
tagtgggcca tcgccctgat agacggtttt tcgccctttg acgttggagt ccacgttctt      660
taatagtgga ctcttgttcc aaactggaac aacactcaac cctatctcgg tctattcttt      720
tgatttataa gggattttgc cgatttcggc ctattggtta aaaatgagc tgatttaaca       780 aaaatttaac gcgaatttta acaaaatatt aacgcttaca atttcctgat gcggtatttt      840
ctccttacga tctgtgcgg tatttcacac cgcatacgcg gatctgcgca gcaccatggc       900
ctgaaataac ctctgaaaga ggaacttggt taggtacctt ctgaggcgga aagaaccagc      960
tgtggaatgt gtgtcagtta gggtgtggaa agtccccagg ctccccagca ggcagaagta     1020
tgcaaagcat gcatctcaat tagtcagcaa ccaggtgtgg aaagtcccca ggctccccag     1080
```

```
caggcagaag tatgcaaagc atgcatctca attagtcagc aaccatagtc ccgcccctaa   1140
ctccgcccat cccgcccta actccgccca gttccgccca ttctccgccc catggctgac    1200
taattttttt tatttatgca gaggccgagg ccgcctcggc ctctgagcta ttccagaagt   1260
agtgaggagg cttttttgga ggcctaggct tttgcaaaaa gcttgattct tctgacacaa   1320
cagtctcgaa cttaaggcta gagccaccat gattgaacaa gatggattgc acgcaggttc   1380
tccggccgct tgggtggaga ggctattcgg ctatgactgg gcacaacaga caatcggctg   1440
ctctgatgcc gccgtgttcc ggctgtcagc gcaggggcgc ccggttcttt tgtcaagac   1500 cgacctgtcc ggtgccctga tgaactgca ggacgaggca gcgcggctat cgtggctggc    1560
cacgacgggg gttccttgcg cagctgtgct cgacgttgtc actgaagcgg aagggactg    1620 gctgctattg ggcgaagtgc cggggcagga tctcctgtca tctcaccttg ctcctgccga   1680
gaaagtatcc atcatggctg atgcaatgcg gcggctgcat acgcttgatc cggctacctg   1740
cccattcgac caccaagcga aacatcgcat cgagcgagca cgtactcgga tggaagccgg   1800
tcttgtcgat caggatgatc tggacgaaga gcatcagggg ctcgcgccag ccgaactgtt   1860
cgccaggctc aaggcgcgca tgcccgacgg cgaggatctc gtcgtgaccc atggcgatgc   1920
ctgcttgccg aatatcatgg tggaaaatgg ccgcttttct ggattcatcg actgtggccg   1980
gctgggtgtg gcggaccgct atcaggacat agcgttggct acccgtgata ttgctgaaga   2040
gcttggcggc gaatgggctg accgcttcct cgtgctttac ggtatcgccg ctcccgattc   2100
gcagcgcatc gccttctatc gccttcttga cgagttcttc tgagcgggac tctggggttc   2160
gaaatgaccg accaagcgac gcccaacctg ccatcacgat ggccgcaata aaatatcttt   2220
attttcatta catctgtgtg ttggttttt gtgtgaatcg atagcgataa ggatccgcgt    2280
atggtgcact ctcagtacaa tctgctctga tgccgcatag ttaagccagc ccgacaccc    2340 gccaacaccc gctgacgcgc cctgacgggc ttgtctgctc ccggcatccg cttacagaca   2400
agctgtgacc gtctccggga gctgcatgtg tcagaggttt tcaccgtcat caccgaaacg   2460 cgcgagcga aagggcctcg tgatacgcct atttttatag gttaatgtca tgataataat    2520
ggtttcttag acgtcaggtg cacttttcg gggaaatgtg cgcggaaccc ctatttgttt    2580 attttctaa atacattcaa atatgtatcc gctcatgaga caataaccct gataaatgct    2640
tcaataatat tgaaaaagga agagtatgag tattcaacat ttccgtgtcg cccttattcc   2700
cttttttgcg gcattttgcc ttcctgtttt tgctcaccca gaaacgctgg tgaaagtaaa   2760
agatgctgaa gatcagttgg gtgcacgagt gggttacatc gaactggatc tcaacagcgg   2820
taagatcctt gagagttttc gccccgaaga acgttttcca atgatgagca cttttaaagt   2880
tctgctatgt ggcgcggtat tatcccgtat tgacgccggg caagagcaac tcggtcgccg   2940
catacactat tctcagaatg acttggttga gtactcacca gtcacagaaa agcatcttac   3000
ggatggcatg acagtaagag aattatgcag tgctgccata accatgagtg ataacactgc   3060
ggccaactta cttctgacaa cgatcggagg accgaaggag ctaaccgctt ttttgcacaa   3120
catgggggat catgtaactc gccttgatcg ttgggaaccg gagctgaatg aagccatacc   3180
aaacgacgag cgtgacacca cgatgcctgt agcaatggca acaacgttgc gcaaactatt   3240
aactggcgaa ctacttactc tagcttcccg gcaacaatta atagactgga tggaggcgga   3300
taaagttgca ggaccacttc tgcgctcggc ccttccggct ggctggttta ttgctgataa   3360
atctggagcc ggtgagcgtg ggtctcgcgg tatcattgca gcactggggc cagatggtaa   3420
```

```
gccctcccgt atcgtagtta tctacacgac ggggagtcag gcaactatgg atgaacgaaa   3480
tagacagatc gctgagatag gtgcctcact gattaagcat tggtaactgt cagaccaagt   3540
ttactcatat atactttaga ttgatttaaa acttcatttt taatttaaaa ggatctaggt   3600
gaagatcctt tttgataatc tcatgaccaa atcccttaa cgtgagtttt cgttccactg    3660
agcgtcagac cccgtagaaa agatcaaagg atcttcttga gatcctttttt ttctgcgcgt  3720 aatctgctgc ttgcaaacaa aaaaccacc gctaccagcg gtggtttgtt tgccggatca    3780
agagctacca actcttttt cgaaggtaac tggcttcagc agagcgcaga taccaaatac    3840
tgttcttcta gtgtagccgt agttaggcca ccacttcaag aactctgtag caccgcctac   3900
atacctcgct ctgctaatcc tgttaccagt ggctgctgcc agtggcgata agtcgtgtct   3960
taccgggttg gactcaagac gatagttacc ggataaggcg cagcggtcgg gctgaacggg   4020
gggttcgtgc acacagccca gcttggagcg aacgacctac accgaactga gatacctaca   4080
gcgtgagcta tgagaaagcg ccacgcttcc gaaggagaa aaggcggaca ggtatccggt    4140
aagcggcagg gtcggaacag gagagcgcac gagggagctt ccaggggga acgcctggta    4200 tctttatagt cctgtcgggt ttcgccacct ctgacttgag cgtcgatttt tgtgatgctc   4260
gtcagggggg cggagcctat ggaaaaacgc cagcaacgcg gcctttttac ggttcctggc   4320
cttttgctgg ccttttgctc acatggctcg acagatcttc aatattggcc attagccata   4380
ttattcattg gttatatagc ataaatcaat attggctatt ggccattgca tacgttgtat   4440
ctatatcata atatgtacat ttatattggc tcatgtccaa tatgaccgcc atgttggcat   4500
tgattattga ctagttatta atagtaatca attacggggt cattagttca tagcccatat   4560
atggagttcc gcgttacata acttacggta atggcccgc ctggctgacc gcccaacgac    4620
ccccgcccat tgacgtcaat aatgacgtat gttcccatag taacgccaat agggactttc   4680
cattgacgtc aatgggtgga gtatttacgg taaactgccc acttggcagt acatcaagtg   4740
tatcatatgc caagtccgcc ccctattgac gtcaatgacg gtaaatggcc cgcctggcat   4800
tatgcccagt acatgacctt acgggacttt cctacttggc agtacatcta cgtattagtc   4860
atcgctatta ccatggtgat gcggttttgg cagtacacca atgggcgtgg atagcggttt   4920
gactcacggg gatttccaag tctccaccc attgacgtca atgggagttt gttttggcac   4980
caaaatcaac gggactttcc aaaatgtcgt aacaactgcg atcgcccgcc ccgttgacgc   5040
aaatgggcgg taggcgtgta cggtgggagg tctatataag cagagctcgt ttagtgaacc   5100
gtcagatcac tagaagcttt attgcggtag tttatcacag ttaaattgct aacgcagtca   5160
gtgcttctga cacaacagtc tcgaacttaa gctgcagtga ctctcttaag gtagccttgc   5220
agaagttggt cgtgaggcac tgggcaggta agtatcaagg ttacaagaca ggtttaagga   5280
gaccaataga aactgggctt gtcgagacag agaagactct tgcgtttctg ataggcacct   5340
attggtctta ctgacatcca ctttgccttt ctctccacag gtgtccactc ccagttcaat   5400
tacagctctt aaggctagag tacttaatac gactcactat aggctagcct cgagcgcgga   5460
gatgggggtg cacgaatgtc ctgcctggct gtggcttctc ctgtccctgc tgtcgctccc   5520
tctgggcctc ccagtcctgg gcgccccacc acgcctcatc tgtgacagcc gagtcctgga   5580
gaggtacctt ttgaggcca aggaggccga gaatatcacg acgggctgtg ctgaacactg    5640
cagcttgaat gagaatatca ctgtcccaga caccgacgtt aatttctatg cctggaagag   5700
gatggaggtc gggcagcagg ccgtagaagt ctggcagggc ctggccctgc tgtcggaagc   5760
tgtcctgcgg ggccaggccc tgttggtcaa ctcttcccag ccgtgggagc ccctgcagct   5820
```

```
gcatgtggat aaagccgtcg agggccttcg cagcctcacc actctgcttc gggctctgcg   5880
agcccagaag gaagccatct cccctccaga tgcggcctca gctgctccac tccgaacaat   5940
cactgctgac actttccgca aactcttccg agtctactcc aatttcctcc ggggaaagct   6000
gaagctgtac acaggggagg cctgcaggac aggggaccat catcaccatc accattgat    6059
```